United States Patent [19]

Ryono et al.

[11] Patent Number: 4,885,292

[45] Date of Patent: Dec. 5, 1989

[54] N-HETEROCYCLIC ALCOHOL RENIN INHIBITORS

[75] Inventors: Denis E. Ryono, Princeton; Harold N. Weller, III, Pennington, both of N.J.

[73] Assignee: E. R. Squibb & Sons, Inc., Princeton, N.J.

[21] Appl. No.: 373,633

[22] Filed: Jun. 29, 1989

Related U.S. Application Data

[63] Continuation of Ser. No. 3,446, Jan. 15, 1987, abandoned, which is a continuation-in-part of Ser. No. 825,724, Feb. 3, 1986, abandoned.

[51] Int. Cl.$^4$ ............... A61K 31/55; C07D 413/12
[52] U.S. Cl. .................. 514/211; 514/212;
514/235.8; 514/252; 514/332; 514/333;
514/336; 514/357; 514/365; 514/367; 514/374;
514/375; 514/394; 514/395; 514/397; 514/398;
514/400; 514/406; 514/407; 514/422; 514/424;
514/427; 540/544; 540/553; 540/575; 540/597
[58] Field of Search ............. 548/344, 342, 336, 337,
548/180, 217, 527, 517, 542, 561, 374, 375, 378,
205, 236, 327, 329, 330, 204; 546/256, 265, 283,
284, 335, 336, 337; 514/397, 398, 400, 406, 407,
422, 424, 427, 394, 395, 365, 374, 333, 332, 336,
357, 367, 375, 235.8, 252, 211, 212; 544/139,
370; 540/544, 553, 575, 597, 602, 603

[56] References Cited

U.S. PATENT DOCUMENTS 4,599,198  2/1986  Hoover ........................... 530/333 X
4,698,329  10/1987  Matsueda et al. .................... 514/18

OTHER PUBLICATIONS

Burger, *Medicinal Chem.*, 2nd Ed., Interscience, New York, 1960, pp. 551-564, 572-578, 582-599, and 602-620.

Rosenberg, S. et al., *J. Med. Chem.*, 1987, vol. 30, pp. 1224-1228.

Burger, A. (editor), *Medicinal Chemistry*, 2nd ed., Interscience, New York, 1960, pp. 565-571, 579-581 and 600-601.

*Primary Examiner*—Richard A. Schwartz
*Attorney, Agent, or Firm*—Donald J. Barrack; Stephen B. Davis

[57] ABSTRACT

Compounds of the formula

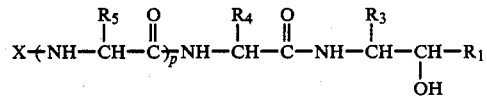

are disclosed wherein $R_1$ is N-heterocyclic moiety. These compounds intervene in the conversion of angiotensin to angiotensin II by inhibiting renin and thus are useful as antihypertensive agents.

42 Claims, No Drawings

N-HETEROCYCLIC ALCOHOL RENIN INHIBITORS

RELATED APPLICATION

This application is a continuation of Ser. No. 003,446 filed Jan. 15, 1987, now abandoned, which was a continuation-in-part of Ser. No. 825,724 filed Feb. 3, 1986, now abandoned.

BACKGROUND OF THE INVENTION

Jones et al. in WO 84/03044 disclose renin inhibiting tetra-, penta-, or hexapeptide analogues of the formula

where X and W are terminal groups; D, E, B and Z, of which any one or, except with reduced analogues, two may be absent, are aromatic, lipophilic or (in the case of E) aromatic, lipophilic, or basic amino acid or amino acid analogue residues, and A is an analogue of a lipophilic or aromatic dipeptide residue wherein the peptide link is replaced by one to four-atom carbon or carbonnitrogen link which as such or in hydrated form is an unhydrolyzable tetrahedral analogue of the transition state of the peptide bond as given above. In particular, A is defined as

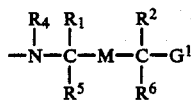

wherein M can be —CH—OH.

Szelke et al. in European Patent Application 104,041 disclose renin inhibitory polypeptides including the partial sequence

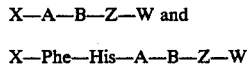

wherein A is

and G is

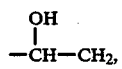

X is hydrogen, protecting group, or an amino acyl residue, B is a lipophilic amino acyl residue, and Z plus W are an amino alcohol residue or Z is aminoacyl and W is hydroxy, ester, amide, etc.

Matsueda et al. in U.S. Pat. No. 4,548,926 disclose renin inhibiting peptides of the formula

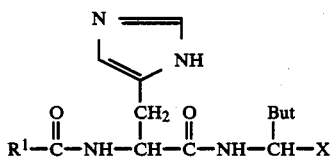

wherein But represents an isobutyl or sec-butyl group and X includes a group of the formula —CH($R^2$)—Y.

Gordon et al. in U.S. Pat. No. 4,514,391 disclose hydroxy substituted peptide compounds of the formula

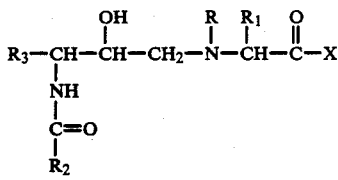

which possess angiotensin converting enzyme or enkephalinase inhibition activity.

SUMMARY OF THE INVENTION

This invention is directed to new heterocyclic alcohol containing renin inhibitors of formula I including pharmaceutically acceptable salts thereof

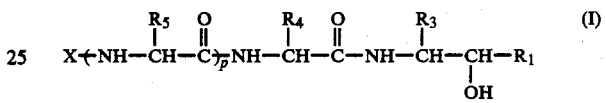

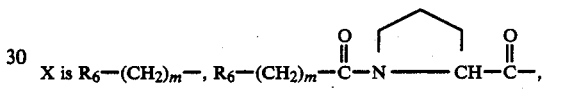

X is 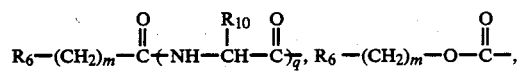

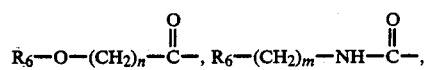

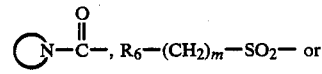

$R_3$, $R_4$, $R_5$ and $R_{10}$ are independently selected from hydrogen, lower alkyl, halo substituted lower alkyl, —$(CH_2)_n$-aryl, —$(CH_2)_n$-heterocyclo, —$(CH_2)_n$—OH, —$(CH_2)_n$—O—lower alkyl, —$(CH_2)_n$—$NH_2$, —$(CH_2)_n$—SH, —$(CH_2)_n$—S—lower alkyl, —$(CH_2)_n$—O—$(CH_2)_g$—OH, —$(CH_2)_n$—O—$(CH_2)_g$—$NH_2$, —$(CH_2)_n$—S—$(CH_2)_g$—OH,

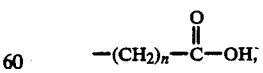

—$(CH_2)_n$—S—$(CH_2)_g$—$NH_2$,

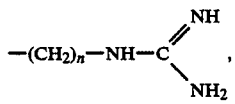

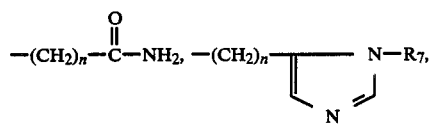 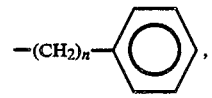

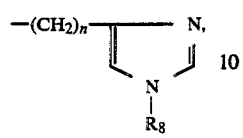

and —(CH$_2$)$_n$-cycloalkyl.

R$_6$ and R$_6'$ are independently selected from lower alkyl, cycloalkyl, aryl and heterocyclo.

p is zero or one.

q is zero or one.

m and m' are independently selected from zero and an integer from 1 to 5.

n is an integer from 1 to 5.

g is an integer from 2 to 5.

R$_7$ is

R$_8$ is 2,4-dinitrophenyl,

—SO$_2$—⟨⟩—CH$_3$, or —CH$_2$—O—CH$_2$—⟨⟩.

R$_1$ is a fully saturated, partially saturated, or unsaturated monocyclic N-heterocyclic ring of 5 or 6 atoms containing at least one N atom or a bicyclic ring in which such N-heterocyclic ring is fused to a benzene ring. The N-heterocyclic ring can also include an O or S atom or up to three additional N atoms. The N-heterocyclic ring is attached to

—CH—
|
OH by way of an available carbon atom. An available N atom in the N-heterocyclic ring can be substituted with an N-protecting group such as

or 2,4-dinitrophenyl, or lower alkyl,

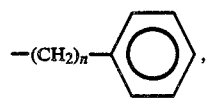

or —(CH$_2$)$_n$-cycloalkyl. Similarly, an available C atom in the monocyclic ring or an avaliable C atom in the benzene portion of the bicyclic ring can be substituted with lower alkyl, —(CH$_2$)$_n$—⟨⟩, or —(CH$_2$)$_n$-cycloalkyl.

Preferred N-heterocyclic rings are

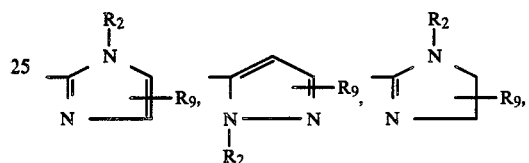

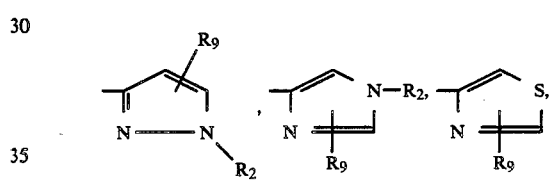

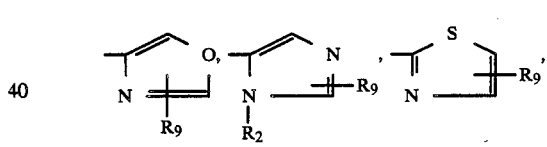

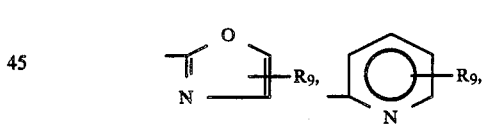

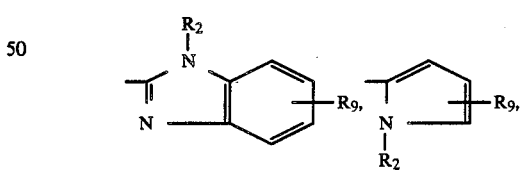

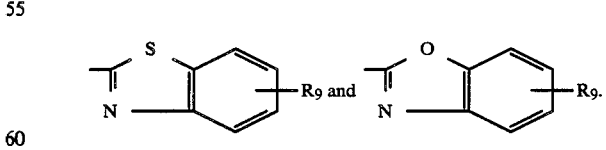

R$_2$ is

2,4-dinitrophenyl, hydrogen, lower alkyl, $$-(CH_2)_n-\phenyl$$

or —$(CH_2)_n$-cycloalkyl.

$R_9$ is hydrogen, lower alkyl, $$-(CH_2)_n-\phenyl,$$

or —$(CH_2)_n$-cycloalkyl.

$$\bigcirc N-$$

represents a heterocyclic ring of the formula $$Y\underset{(CH_2)_b}{\overset{(CH_2)_a}{\diagup}}N-$$

wherein Y is —$CH_2$, O, S, or N-$R_9$, a is an integer from 1 to 4, and b is an integer from 1 to 4 provided that the sum of a plus b is an integer from 2 to 5 and such heterocyclic rings wherein one carbon atom has a lower alkyl substituent.

DETAILED DESCRIPTION OF THE INVENTION

This invention in its broadest aspects relates to the compounds of formula I above, to compositions and the method of using such compounds as antihypertensive agents, and intermediates useful in the preparation of such compounds.

The term lower alkyl used in defining various symbols refers to straight or branched chain radicals having up to seven carbons. Similarly, the terms lower alkoxy and lower alkylthio refer to such lower alkyl groups attached to an oxygen or sulfur. The preferred lower alkyl groups are straight or branched chain of 1 to 5 carbons.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are selected from methyl, methoxy, methylthio, halogen, and hydroxy.

The term heterocyclo refers to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred hetero groups include 2- and 3-thienyl, 2- and 3-furyl, 2-, 3- and 4-pyridyl. The term hetero also includes bicyclic rings wherein the five or six membered ring containing O, S and N atoms as defined above is fused to a benzene ring. The preferred bicyclic ring is benzimidazolyl.

The compounds of formula I wherein $$X \text{ is } R_6-(CH_2)_m-O-\overset{O}{\underset{\|}{C}}-$$

can be prepared by coupling an alcohol of the formula (II)

$$H_2N-\underset{}{CH}-\underset{OH}{\overset{R_3}{\underset{|}{CH}}}-R_1$$

with a peptide of the formula (III)

$$R_6-(CH_2)_m-O-\overset{O}{\underset{\|}{C}}(-NH-\underset{}{\overset{R_5}{\underset{|}{CH}}}-\overset{O}{\underset{\|}{C}})_p NH-\underset{}{\overset{R_4}{\underset{|}{CH}}}-COOH.$$

This reaction is preferably performed in a solvent such as dimethylformamide and in the presence of hydroxybenzotriazole, N-methylmorpholine, and a coupling agent such as dicyclohexylcarbodiimide.

The corresponding compounds of formula I wherein p is zero can be prepared by coupling the alcohol of formula II with the amino acid of the formula (IV)

$$R_6-(CH_2)_m-O-\overset{O}{\underset{\|}{C}}-NH-\underset{}{\overset{R_4}{\underset{|}{CH}}}-COOH$$

to yield the products of the formula (V)

$$R_6(CH_2)_m-O-\overset{O}{\underset{\|}{C}}-NH-\underset{}{\overset{R_4}{\underset{|}{CH}}}-\overset{O}{\underset{\|}{C}}-NH-\underset{OH}{\overset{R_3}{\underset{|}{CH}}}-\underset{}{CH}-R_1.$$

When $R_6$—$(CH_2)_m$— is t-butyl or benzyl, then the product of formula V can be treated so as to remove the t-butoxycarbonyl or benzyloxycarbonyl group such as by the use of anhydrous hydrochloric acid when $R_6$ is t-butyl to yield the amine of the formula (VI)

$$H_2N-\underset{}{\overset{R_4}{\underset{|}{CH}}}-\overset{O}{\underset{\|}{C}}-NH-\underset{OH}{\overset{R_3}{\underset{|}{CH}}}-\underset{}{CH}-R_1.$$

Coupling with the acylated amino acid of the formula (VII)

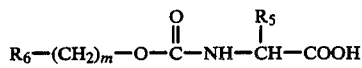

yields the products of formula I wherein p is one.

The compounds of formula I wherein X is other than

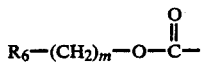

can be prepared by treating the product of formula I wherein X is

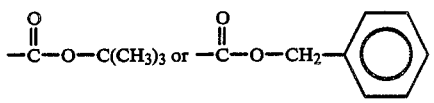

to remove the t-butoxycarbonyl or benzyloxycarbonyl group and yield the intermediates of the formula (VIII)

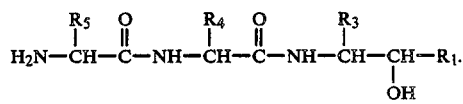

The amine of formula VIII or formula VI is treated with the halide of the formula (IX)

particularly where halo is Br to give the products of formula I wherein X is $R_6-(CH_2)_m-$.

The compounds of formula I wherein X is

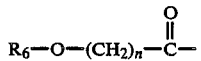

can be prepared by treating the amine of formula VIII or VI with the acid chloride of the formula (X)

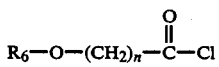

in the presence of triethylamine.

The compounds of formula I wherein X is $R_6-(CH_2)_m-SO_2-$ can be prepared by treating the amine of formula VIII or VI with the substituted sulfonyl chloride of the formula (XI)

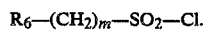

The compounds of formula I wherein X is

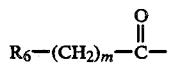

can be prepared by treating the amine of formula VIII or VI with the acid chloride of the formula (XII)

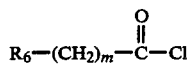

in the presence of triethylamine. Alternatively, these compounds can also be prepared by coupling the carboxylic acid of the formula (XIII)

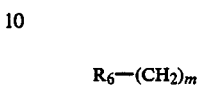

to the amine of formula VI or VIII in the presence of a coupling agent such as dicyclohexylcarbodiimide and 1-hydroxybenzotriazole hydrate.

The compounds of formula I wherein X is

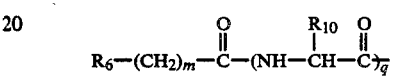

and q is one can be prepared by acylating the amino acid of the formula (XIV)

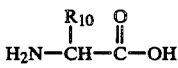

with the acid chloride of formula XII in the presence of base such as sodium hydroxide (i.e. at a pH of about 8) and in a solvent such as tetrahydrofuran and water to give the acylated amino acid of the formula (XV)

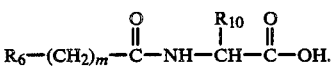

The amino acid of formula XV is then coupled to the amine of formula VI or VIII in the presence of dicyclohexylcarbodiimide and 1-hydroxybenzotriazole hydrate to give the desired compounds of formula I.

The compounds of the formula I wherein X is

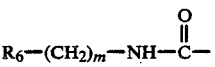

and p is one can be prepared by coupling an amino acid of the formula (XVI)

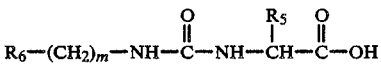

to the amine of formula VI in the presence of a coupling agent such as dicyclohexylcarbodiimide and 1-hydroxybenzotriazole hydrate.

Similarly, the compounds of formula I wherein X is

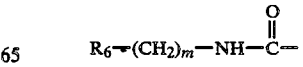

and p is zero can be prepared by coupling an amino acid of the formula (XVII)

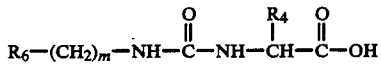

to an alcohol of formula II in the presence of a coupling agent such as dicyclohexylcarbodiimide and 1-hydroxybenzotriazole hydrate.

The compounds of formula I wherein X is

and p is one can be prepared by coupling an amino acid of the formula (XVIII)

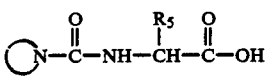

to the amine of formula VI in the presence of a coupling agent such as dicyclohexylcarbodiimide and 1-hydroxybenzotriazole hydrate.

Similarly, the compounds of formula I wherein X is

and p is zero can be prepared by coupling an amino acid of the formula (XIX)

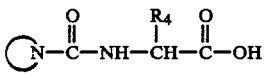

to the alcohol of formula II in the presence of a coupling agent such as dicyclohexylcarbodiimide and 1-hydroxybenzotriazole hydrate.

The amino acid intermediates of formulas XVI, XVII, XVIII, and XIX can be prepared by treating an amine $R_6-(CH_2)_m-NH_2$ with phosgene and N-methyl morpholine followed by reaction with an amino acid methyl ester hydrochloride salt of the formula (XX)

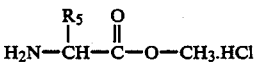

or of the formula (XXI)

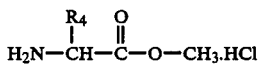

in the presence of N-methyl morpholine. Removal of the methyl ester group by treatment with aqueous sodium hydroxide gives the desired intermediate.

The products of formula I wherein

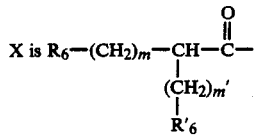

can be prepared by coupling the carboxylic acid of the formula (XXII)

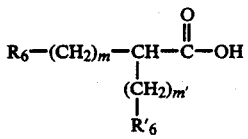

to the amine of formula VI or VIII in the presence of dicyclohexylcarbodiimide and 1-hydroxybenzotriazole hydrate. Alternatively, the acid of formula XXII can be converted to the acid chloride and this acid chloride can then be coupled to the amine of formula VI or VIII in the presence of triethylamine and tetrahydrofuran or water and sodium bicarbonate.

The compounds of formula I wherein X is

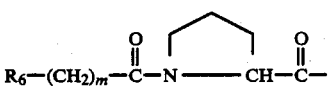

can be prepared by acylating proline with the acid chloride of formula XII in the presence of base such as sodium hydroxide, i.e., a pH of about 8, and a solvent mixture of tetrahydrofuran and water to give (XXIII)

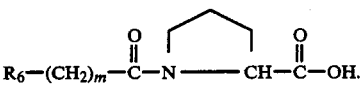

The acylated amino acid of formula XXIII is then coupled to the amine of formula VIII or VI in the presence of a coupling agent such as dicyclohexylcarbodiimide and 1-hydroxybenzotriazole hydrate.

The alcohol of formula II can be prepared by treating the N-heterocyclic starting material of the formula $H-R_1$ with n-butyl lithium to yield the lithium compound of the formula (XXIV)

This lithium N-heterocyclic compound is then reacted with the aldehyde of the formula (XXV)

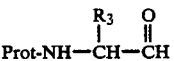

wherein Prot is an amino protecting group such as t-butoxycarbonyl. Removal of the t-butoxycarbonyl group such as by treatment with hydrochloric acid gives the alcohol of formula II.

The aldehyde of formula XXV is prepared by treating the N-protected α-amino acid ester of the formula (XXVI)

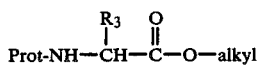

with lithium borohydride to give the alcohol of the formula (XXVII)

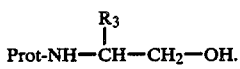

Treatment of the alcohol of formula XXVII with pyridine-sulfur trioxide complex or with periodinane reagent [see Dess et al., J. Org. Chem., Vol. 48, p. 5155–4156 (1983)] gives the desired aldehyde.

In the above reactions, if any of $R_3$, $R_4$, $R_5$ and $R_{10}$ are —$(CH_2)_n$-aryl wherein aryl is phenyl, 1-naphthyl, 2-naphthyl substituted with one or more hydroxy or amino groups, —$(CH_2)_n$-heterocyclo wherein heterocyclo is an imidazolyl, —$(CH_2)_n$—$NH_2$,

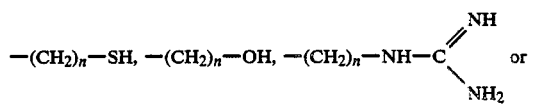

then the hydroxyl, amino, imidazolyl, mercaptan, carboxyl, or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or by other known means following completion of the reaction.

The various peptide intermediates employed in above procedures are known in the literature or can be readily prepared by known methods. See for example, The Peptides, Volume 1, "Major Methods Of Peptide Bond Formation", Academic Press (1979).

Preferred compounds of this invention are those of formula I wherein:

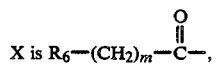

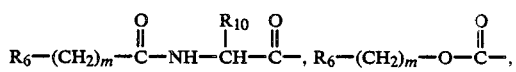

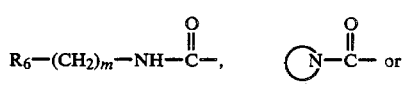

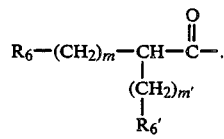

$R_6$ and $R_6'$ are independently selected from straight or branched chain lower alkyl of up to 5 carbons, cycloalkyl of 4 to 6 carbons, phenyl, 1-naphthyl, and 2-naphthyl.

m and m' are independently selected from zero, one and two.

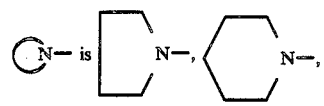

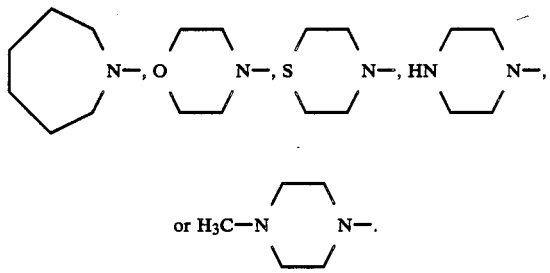

Especially preferred are the compounds wherein X is

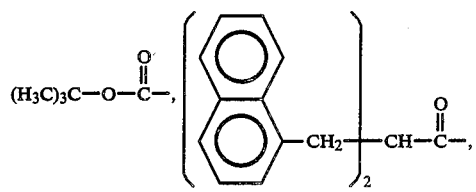

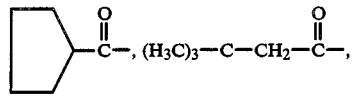

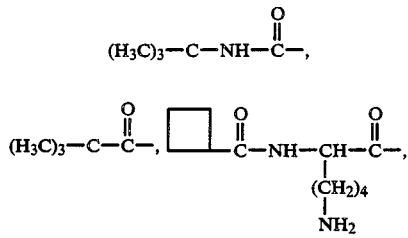

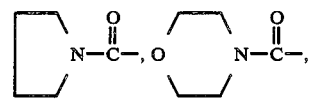

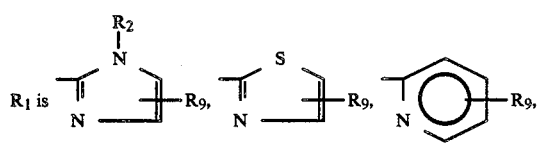

-continued

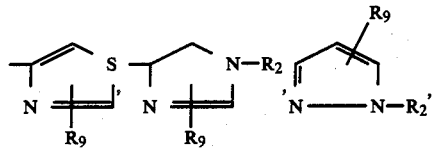

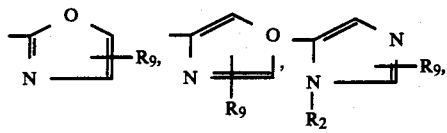

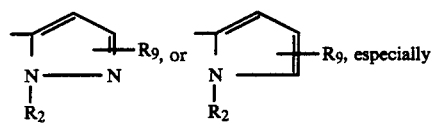

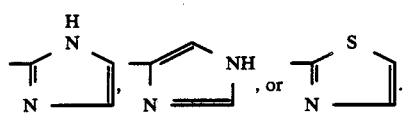

R₂ is

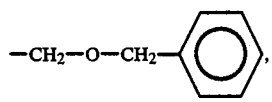

hydrogen, straight or branched chain lower alkyl of up to 5 carbons, or

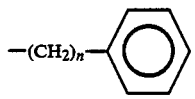

wherein n is an integer from 1 to 3.

R₉ is hydrogen, straight or branched chain lower alkyl of up to 5 carbons, or

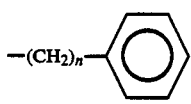

wherein n is an integer from 1 to 3.

R₃ is straight or branched chain lower alkyl of 3 to 5 carbons, —(CH₂)ₙ-cyclopentyl, —(CH₂)ₙ-cyclohexyl, or

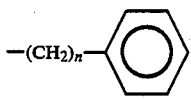

wherein n is an integer from 1 to 3, especially

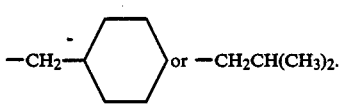

R₄ is hydrogen, straight or branched chain lower alkyl of up to 5 carbons, —(CH₂)₄—NH₂,

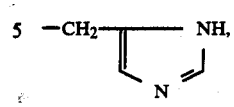

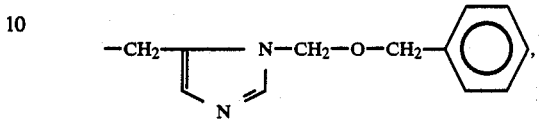

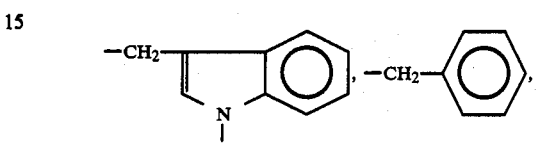

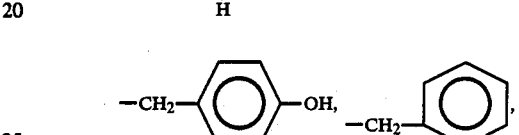

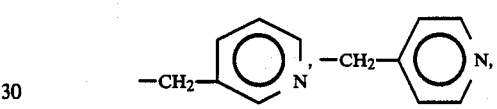

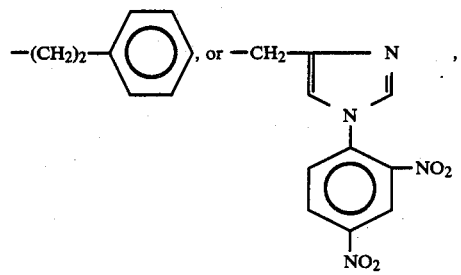

R₅ is straight or branched chain lower alkyl of up to 5 carbons,

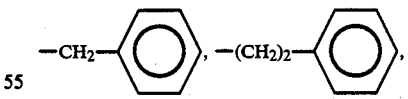

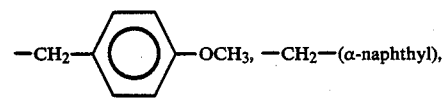

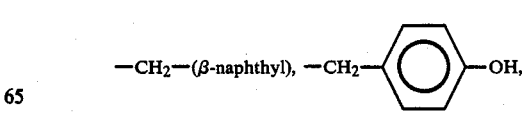

—CH₂—cyclopentyl, —CH₂—cyclohexyl,

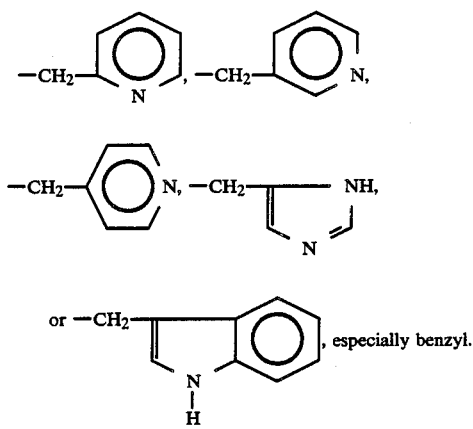

, especially benzyl.

The compounds of formula I form salts with a variety of inorganic and organic acids. The nontoxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

The compounds of formula I contain asymmetric centers when any or all of $R_3$, $R_4$, $R_5$ and $R_{10}$ are other than hydrogen and at the carbon to which the —OH group is attached. Thus, the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are antihypertensive agents. They inhibit the conversion of angiotensinogen to angiotensin I and therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen → (renin) → angiotensin I → (ACE) → angiotensin II sequence by inhibiting renin and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 100 to 1000 mg., preferably about 250 to 500 mg. per kg. of body weight per day is appropriate to reduce blood pressure. The substance is preferably administered orally, but parenteral routes such as the subcutaneous, intramuscular, intraveneous or intraperitoneal routes can also be employed.

The compounds of this invention can also be formulated in combination with a diuretic for the treatment of hypertension.

A combination product comprising a compound of this invention and a diuretic can be administered in an effective amount which comprises a total daily dosage of about 1000 to 6000 mg., preferably about 3000 to 4000 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 100 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. All temperatures are given in degrees centigrade.

EXAMPLE 1

$N^2$-[N-[(1,1-Dimethylethoxy)carbonyl]-L-phenylalanyl]-N-[(S)-1-[hydroxy(1H-imidazol-2-yl)methyl]-3-methylbutyl]-L-histidinamide, acetic acid solvate (a) N-[(1,1-Dimethylethoxy)carbonyl]-L-leucinal Thionyl chloride (50.2 ml., 691 mmole) is added dropwise over a period of 20 minutes to a stirred (ice-cold) suspension of L-leucine (72.05 g., 550 mmole) in absolute ethanol. After the addition is completed, the ice-bath is removed and the reaction mixture is stirred at room temperature for one hour. It is then refluxed for five hours on a steam bath. It is then concentrated in vacuo and diluted with ether. The separated crystals are filtered to give 99.9 g. of L-leucine, ethyl ester, monohydrochloride;

m.p. (130) 135°–137°; $[\alpha]^{22}_D = +14.7°$ (c=2.3, methanol),

A solution of L-leucine, ethyl ester, monohydrochloride (46.85 g., 239.4 mmole) in 75% ethanol (500 ml.) is added to a vigorously stirred solution of sodium borohydride (35 g., 907 mmole) in 75% ethanol (500 ml.) over a period of thirty minutes. After the addition is completed, the reaction mixture is refluxed for 3 hours. Ethanol is removed in vacuo. The aqueous solution is extracted with ethyl acetate. The aqueous solution is again extracted with ethyl acetate after saturating with sodium chloride. The combined ethyl acetate solution after washing with saturated sodium chloride solution is evaporated to give 20.8 g. of crude (S)-2-amino-4-methyl-1-pentanol.

Di-tert-butyl dicarbonate (38.73 g., 177.5 mmole) is added to a stirred (ice-bath) solution of (S)-2-amino-4-methyl-1-pentanol (20.8 g., 177.5 mmole) in tetrahydrofuran (340 ml.). After stirring in an ice-bath for 15 minutes, the reaction mixture is stirred at room temperature for 3 hours. The tetrahydrofuran is removed in vacuo. This crude product (40.53 g.) is combined with 36.25 g. from a previous run and the entire amount is chromatographed over silica gel (800 g.) using the solvent system ethyl acetate:hexane (1:1) to yield 72.6 g. of (S)-2-[[(1,1-dimethylethoxy)carbonyl]amino]-4-methyl-1-pentanol as an oil; $[\alpha]^{22}_D = -26.2°$ (c=1.5, methanol).

Triethylamine (63 ml., 450 mmole), dimethylsulfoxide (63.9 ml., 900 mmole), and pyridinesulfur trioxide complex (71.6 g., 450 mmole) are added to a stirred (room temperature) solution of (S)-2-[[(1,1-dimethylethoxy)carbonyl]amino]-4-methyl-1-pentanol (32.59 g., 150 mmole) in methylene chloride (750 ml.). After stirring the reaction mixture for 15 minutes, it is evaporated in vacuo at room temperature. Ice-water (450 ml.) is added to the residue which is then extracted with ether. The ether extract is successively washed with 10% citric acid, water, saturated sodium bicarbonate, and water. The ether extract on evaporation gives 19.73 g. of N-[(1,1-dimethylethoxy)carbonyl]-L-leucinal as an oil; $[\alpha]^{22}_D = -50°$ (c=4.6, methanol).

(b) α-[(S)-1-Amino-3-methylbutyl]-1-[(phenylmethoxy)methyl]-1H-imidazole-2-methanol, dihydrochloride 2.5 M n-Butyllithium solution in hexane (4.6 ml., 11.5 mmole) is added to a solution of 1-[(phenylmethoxy)methyl]-1H-imidazole (2.06 g., 10.94 mmole; prepared as described by Brown et al., J.Chem.Soc. Perkin Trans. I, 1982, p. 1553) in tetrahydrofuran (35 ml.) at −70° under argon. After 45 minutes at −70°, an orange colored solution results. At this point, a solution of N-[(1,1-dimethylethoxy)carbonyl]-L-leucinal (1.18 g., 5.47 mmole) in tetrahydrofuran (7 ml.) is carefully added over a period of 2-3 minutes. The reaction is kept at −70° for one hour, then at 0° for 15 minutes, and then is quenched by the addition of saturated ammonium chloride (6 ml.). The reaction mixture is diluted with ether and rinsed with several portions of water and brine, and dried over magnesium sulfate. Concentration in vacuo gives 3.13 g. of crude product. Flash chromatography on silica gel (120 g. of Whatman LPS-1) eluting with petroleum ether:acetone (4:1) gives 261 mg. of α-[(S)-1-[[(1,1-dimethylethoxy)-carbonyl]amino]-3-methylbutyl]-1-[(phenylmethoxy)methyl]-1H-imidazole-2-methanol, fast moving isomer; $[\alpha]^{22}_D = +5.8°$ (c=0.5, chloroform), 564 mg. of α-[(S)-1-[[(1,1-dimethylethoxy)carbonyl]amino]-3-methylbutyl]-1-[(phenylmethoxy)methyl]-1H-imidazole-2-methanol, slow moving isomer; $[\alpha]^{22}_D = +12.2°$ (c=0.5, chloroform), and 625 mg. of a mixture fraction for a total yield of 1.45 g. of product; TLC (silica gel; petroleum ether:acetone, 3:1) $R_f$=0.39, 0.13.

Anal. calc'd. for $C_{22}H_{33}N_3O_4$:
C, 65.48; H, 8.24; N, 10.41
Found: C, 65.05; H, 8.20; N, 10.21
(fast moving isomer)
C, 65.26; H, 8.37; N, 10.29
(slow moving isomer)

A (1:1) isomeric mixture of the above fast and slow moving isomers (493 mg., 1.22 mmole) is dissolved in 10 ml. of ethyl acetate and cooled in an ice-water bath under argon. The solution is saturated with dry hydrochloric acid and stirred cold for one hour, and then concentrated in vacuo to give 420 mg. of crude product. Chromatography on a 30×350 mm. HP-20 column gradient eluted from 350 ml. of 9:1 to 1:9, 0.01 N aqueous hydrochloric acid:acetonitrile at 9 ml./2min./fraction yields 402 mg. of α-[(S)-1-amino-3-methylbutyl]-1-[(phenylmethoxy)methyl]-1H-imidazole-2-methanol, dihydrochloride; m.p. 98°-117°; $[\alpha]^{22}_D = -0.3°$ (c=1, methanol). TLC (silica gel; n-butanol: pyridine:acetic acid:water, 4:1:1:1) $R_f$=0.78.

Anal. calc'd for $C_{17}H_{25}N_3O_2 \cdot 2HCL \cdot 1.7 H_2O$:
C, 50.17; H, 7.53; N, 10.33; Cl, 17.42
Found: C, 50.13; H, 7.54; N, 10.29; Cl, 17.58

(c) N-[N-[(1,1-Dimethylethoxy)carbonyl]-L-phenylalanyl]-1′-[(phenylmethoxy)methyl]-L-histidine Thionyl chloride (27.2 ml., 375 mmole) is added in drops to a stirred solution in an icebath of L-histidine (38.75 g., 240 mmole) in methanol (500 ml.). After 15 minutes the ice-bath is removed and the reaction mixture is stirred at room temperature for one hour. After refluxing for 48 hours, it is concentrated in vacuo. The separated crystals are filtered using methanol for washings to 48.93 g. of L-histidine, methyl ester, dihydrochloride. The methanolic solution on dilution with ether affords an additional 10 g. of product;
m.p. 208°-209°; $[\alpha]^{22}_D = +10.1°$ (c=1.8, water).

Triethylamine (28 ml., 200 ml.) and di-tertbutyl dicarbonate (48 g., 220 mmole) are added to a suspension of L-histidine, methyl ester (24.2 g., 100 mmole) in methanol (80 ml.). After 3.5 hours, the mixture is filtered and the methanolic solution is concentrated in vacuo. The residue is taken into chloroform and washed with 10% citric acid. The crude product on crystallization from isopropyl ether affords 23.1 g. of N,1′-bis[(1,1-dimethylethoxy)carbonyl]-L-histidine, methyl, ester; m.p. (62) 88°-95°; $[\alpha]^{22}_D = +25.4°$ (c=1.1, carbon tetrachloride).

Benzylchloromethyl ether (11.6 ml., 83.6 mmole) is added to a solution of N,1′-bis[(1,1-dimethylethoxy)carbonyl]-L-histidine, methyl ester (24.7 g., 66.9 mmole) in dry methylene chloride (156 ml.) and the reaction mixture is stirred at room temperature for 5 hours. After concentrating in vacuo and on dissolution in ethyl acetate 17.85 g. of N-[(1,1-dimethylethoxy)carbonyl]-1′-[(phenylmethoxy)methyl]-L-histidine, methyl ester, monohydrochloride crystallizes out;
m.p. (148°) 152°-153°; $[\alpha]^{22}_D = -19.5°$ (c=1.8, methanol). This methyl ester product is dissolved in hydrogen chloride in acetic acid solution (60 ml., 1.5 N) and kept at room temperature for 15 minutes. It is then evaporated in vacuo and the residue is dissolved in hot isopropanol. After cooling, the separated crystals are filtered to yield 7.08 g. of 1-[(phenylmethoxy)methyl]-L-histidine, methyl ester, dihydrochloride; m.p. (170) 173°-174°.

1-[(Phenylmethoxy)methyl]-L-histidine, methyl ester, dihydrochloride (1.79 g., 4.94 mmole), 1-hydroxybenzotriazole (0.756 g., 4.94 mmole), and N-[(1,1-dimethylethoxy)carbonyl]-L-phenylalanine (1.31 g., 4.94 mmole) are dissolved in dimethylformamide (16 ml.). While stirring the above solution in an ice-bath, dicyclohexylcarbodiimide (1.02 g., 4.94 mmole) and N,N-diisopropylethylamine (1.72 ml., 10 mmole) are added. After 3 hours the ice-bath is removed and the reaction mixture is stirred at room temperature overnight. It is then concentrated to dryness and the residue is triturated with ethyl acetate. The separated urea is filtered off. The ethyl acetate solution is washed with saturated sodium bicarbonate and then it is evaporated. The residue upon crystallization from ethyl acetate gives 1.97 g. of N-[N-[(1,1-dimethylethoxy)carbonyl]-

L-phenylalanyl]-1'-[(phenylmethoxy)methyl]-L-histidine, methyl ester;

m.p. (165) 166°–168°.

N-[N-[(1,1-Dimethylethoxy)carbonyl]-L-phenylalanyl]-1'-[(phenylmethoxy)methyl]-L-histidine, methyl ester (4.5 g., 8.4 mmole) is dissolved in hot methanol (25 ml.). After cooling to room temperature aqueous sodium hydroxide solution (9.24 ml., 1N) is added and the mixture is stirred at room temperature for 3 hours. It is then concentrated in vacuo and water (60 ml.) is added to the residue. After cooling the aqueous solution in an ice-bath, it is acidified to pH 4.5 using aqueous hydrochloric acid. It is then extracted with ethyl acetate to yield 3.95 g. of crystalline N-[N-[(1,1-dimethylethoxy)carbonyl]-L-phenylalanyl]-1'-[(phenylmethoxy)methyl]-L-histidine;

m.p. 193°–194°; $[\alpha]^{22}_D = -4.8°$ (c=1.1, dimethylformamide).

(d) $N^2$-[N-[(1,1-Dimethylethoxy)carbonyl]-L-phenylalanyl]-N-[(S)-1-[hydroxy[1-[(phenylmethoxy)methyl]-1H-imidazol-2-yl]methyl]-3-methylbutyl]-3'-[(phenylmethoxy)methyl]-L-histidinamide N-Methylmorpholine (154 mg., 1.52 mmole) is added to a mixture of N-[N-[(1,1-dimethylethoxy)-carbonyl]-L-phenylalanyl]-1'-[(phenylmethoxy)methyl]-L-histidine (397 mg., 0.759 mmole), α-[(S)-1-amino-3-methylbutyl]-1-[(phenylmethoxy)methyl]-1H-imidazole-2-methanol, dihydrochloride (309 mg., 0.759 mmole), and 1-hydroxybenzotriazole hydrate (116 mg., 0.759 mmole) in dimethylformamide (5 ml.) cooled in an ice-water bath under argon followed by the addition of dicyclohexylcarbodiimide (157 mg., 0.759 mmole). The reaction mixture is kept cold for 2 hours and then refigerated overnight. The reaction mixture is then diluted with ethyl acetate (30 ml.), chilled for 20 minutes, and then filtered. The filtrate is further diluted with ether and the organic solution is rinsed with two portions of water (15 ml.), saturated sodium bicarbonate solution (15 ml.), and brine, dried over magnesium sulfate, and concentrated in vacuo to give 615 mg. of crude product. Two flash chromatographies on silica gel (LPS-1) eluting with chloroform:methanol:ammonia (25:2:0.05) gives 385 mg. of $N^2$-[N-[(1,1-dimethylethoxy)carbonyl]-L-phenylalanyl]-N-[(S)-1-[hydroxy[1-[(phenylmethoxy)methyl]-1H-imidazol-2-yl]methyl]-3-methylbutyl]-3'-[(phenylmethoxy)methyl]-L-histidinamide;

m.p. 69°–84°; $[\alpha]_D = -14.3°$ (c=1, methanol). TLC (silica gel; chloroform:methanol:ammonia, 25:2:0.05) $R_f = 0.2, 0.26$.

Anal. calc'd. for $C_{45}H_{57}N_7O_7 \cdot 0.5 H_2O$:
C, 66.15; H, 7.16; N, 12.00
Found: C, 66.20; H, 7.13; N, 11.73.

(e) $N^2$-[N-[(1,1-Dimethylethoxy)carbonyl]-L-phenylalanyl]-N-[(S)-1-[hydroxy(1H-imidazol-2-yl)methyl]-3-methylbutyl]-L-histidinamide, acetate A solution of the product from part (d) (337 mg., 0.413 mmole) in a mixture of methanol (16 ml.), water (3.1 ml.), and 1N aqueous hydrochloric acid (0.908 ml.) is stirred under an atmosphere of hydrogen (balloon) in the presence of 20% palladium hydroxide on carbon catalyst (80 mg.). After 17 hours, the reaction mixture is filtered, concentrated in vacuo, and flash chromatographed on 36 g. of silica gel (LPS-1) eluting with chloroform:methanol:water:acetic acid (80:20:2.5:1). Pooling of the product containing fractions gives 187 mg. of $N^2$-[N-[(1,1-dimethylethoxy)carbonyl]-L-phenylalanyl]-N-[(S)-1-[hydroxy(1H-imidazol-2-yl)methyl]-3-methylbutyl]-L-histidinamide, acetate;

m.p. 90°–118°; $[\alpha]^{22}_D = -30.8°$ (c=0.5, methanol). TLC (silica gel; chloroform:methanol:water:acetic acid, 90:20:2.5:1) $R_f = 0.14$ and 0.17.

Anal. calc'd. for $C_{29}H_{41}N_7O_5 \cdot 2.4\ C_2H_4O_2 \cdot 2.0\ H_2O$:
C, 54.28; H, 7.36; N, 13.11
Found: C, 54.16; H, 7.01; N. 13.07.

EXAMPLE 2

$N^2$-[N-[(1,1-Dimethylethoxy)carbonyl]-L-phenylalanyl]-N-[(S)-1-[(S)-hydroxy(1H-imidazol-2yl)methyl]-3-methylbutyl]-L-histidinamide, acetic acid solvate (a) $N^2$-[N-[(1,1-Dimethylethoxy)carbonyl]-L-phenylalanyl]-N-[(S)-1-[(S)-hydroxy[1-[(phenylmethoxy)methyl]-1H-imidazol-2-yl]methyl]-3-methylbutyl]-3'-[(phenylmethoxy)methyl]-L-histidinamide A solution of α-[(S)-1-[[(1,1-dimethylethoxy)carbonyl]amino]-3-methylbutyl]-1-[(phenylmethoxy)methyl]-1H-imidazole-2-methanol, fast moving isomer, from Example 1(b), 320 mg., 0.79 mmole) in ethyl acetate (7 ml.) is cooled in an ice-water bath and saturated with gaseous hydrogen chloride. After remaining in the bath for 15 minutes, the bath is removed and the mixture is allowed to stand at ambient temperature in a stopped flask, for 65 minutes. The solution is concentrated in vacuo to give 300 mg. of a solid white powder residue of α-[(S)-1-amino-3-methylbutyl]-1-[(phenylmethoxy)methyl]-1H-imidazole-2(S)- methanol, dihydrochloride;

m.p. 70°–100° .

The above powder (270 mg., 0.66 mmole) is dissolved in dry dimethylformamide (5 ml.). 1-Hydroxybenzotriazole hydrate (100 mg., 0.66 mmole), N-[N-[(1,1-dimethylethoxy)carbonyl]-Liphenylalanyl]-1'-[(phenylmethoxy)methyl]-L-histidine (342 mg., 0.66 mmole) and N-methylmorpholine (127 mg., 1.38 mmole) are added and the mixture is cooled in an ice-water bath and treated with dicyclohexylcarbodiimide (149 mg., 0.66 mmole). The mixture is stirred, in a stoppered flask, in the cold for 15 minutes and then refrigerated for 18 hours. After diluting to a volume of 35 ml. with ethyl acetate, the mixture is filtered to remove insolubles and 35 ml. of ether is added. After washing with water (2×15 ml.), saturated sodium bicarbonate solution (15 ml.) and brine, the mixture is dried over magnesium sulfate and concentrated in vacuo to give 600 mg. of crude product as a viscous oil. This residue is chromatographed on silica gel (LPS-1, 90 g.) eluting with chloroform:methanol: concentrated ammonium hydroxide (30:2:0.05) to give 200 mg. of $N^2$-[N-[(1,1-dimethylethoxy)-carbonyl]-L-phenylalanyl]-N-[(S)-1-[(S)-hydroxy[1-[(phenylmethoxy)methyl]-1H-imidazol-2-yl]-methyl]-3-methylbutyl]-3'-[(phenylmethoxy)methyl]-L-histidinamide as a glassy solid;

m.p. 70°–100° ; $[\alpha]_D = -27.5°$ (10 mg./ml. of methanol). TLC (silica gel; chloroform:methanol: concentrated ammonium hydroxide, 30:2:0.05) $R_f = 0.10$.

Anal. calc'd. for $C_{45}H_{57}N_7O_7 \cdot 0.7H_2O$:
C, 65.86; H, 7.17; N, 11.95
Found: C, 65.86; H, 7.12; N, 11.76.

(b) $N^2$-[N-[(1,1-Dimethylethoxy)carbonyl]-L-phenylalanyl]-N-[(S)-1[(S)-hydroxy(1H-imidazol-2-yl)methyl]-3-methylbutyl]-L-histidinamide To a solution of the product from part (a) (194 mg., 0.236 mmole) dissolved in methanol (8.9 ml.) is added water (1.7 ml.), 1N aqueous hydrochloric acid (0.504 ml.) and 20% palladium hydroxide on carbon catalyst (150 mg.). The mixture is stirred under an atmosphere of hydrogen (balloon) for 18 hours. It is then filtered and concentrated in vacuo to give 153 mg. of crude product. Flash chromatography (LPS-1 silica gel, 25 g.) eluting with chloroform:methanol:water: acetic acid (90:20:2.5:1) followed by lyophillization from 1% aqueous acetic acid of the pooled product containing fractions gives 124 mg. of $N^2$-[N-[(1,1-dimethylethoxy)carbonyl]-L-phenylalanyl]-N-[(S)-1-[(S)-hydroxy(1H-imidazol-2-yl)methyl]-3-methylbutyl]-L-histidinamide, acetic acid solvate;

m.p. 105°–110° ; $[\alpha]_D = -30.1°$ (c=0.5, methanol). TLC (silica gel; chloroform: methanol:water:acetic acid, 90:20:2.5:1) $R_f = 0.11$.

Anal calc'd. for $C_{29}H_{41}N_7O_5 \cdot 1.3\ C_2H_4O_2 \cdot 2.3\ H_2O$:
C, 55.23; H, 7.45; N, 14.27
Found: C, 55.19; H, 7.20; N, 14.29.

EXAMPLE 3

$N^2$-[N-[(1,1-Dimethylethoxy)carbonyl]-L-phenylalanyl]-N-[(S)-1-[(R)-hydroxy(1H-imidazol-2-yl)methyl]-3-methylbutyl]-L-histidinamide, acetic acid solvate (a) $N^2$-[N-[(1,1-Dimethylethoxy)carbonyl]-L-phenylalanyl]-N-[(S)-1-[(R)-hydroxyl[1-[(phenylmethoxy)methyl]-1H-imidazol-2-yl]methyl]-3-methylbutyl]-3'-[(phenylmethoxy)methyl]-L-histidinamide A solution of α-[(S)-1-[[(1,1-dimethylethylethoxy)carbonyl]amino]-3-methylbutyl]-1-[(phenylmethoxy)methyl]-1H-imidazole-2-methanol, slow moving, isomer, from Example 1(b), (404 mg., 1 mmole) in ethyl acetate (15 ml.) is cooled in an ice-water bath to 0° and saturated with gaseous hydrogen chloride. After remaining in the bath for 15 minutes, the bath is removed and the mixture is allowed to stand at ambient temperature for 45 minutes. Removal of the solvents in vacuo gives 396 mg. of solid α-[(S)-1-amino-3-methylbutyl]-1-[(phenylmethoxy)methyl]-1H-imidazole-2(R)-methanol, dihydrochloride.

To a mixture of this amine salt (0.81 mmole), N-[N-[(1,1-dimethylethoxy)carbonyl]-L-phenylalanyl]-1'-[(phenylmethoxy)methyl]-L-histidine (423 mg., 0.81 mmole), and 1-hydroxybenzotriazole hydrate (124 mg., 0.81 mmole) in 6 ml. of dimethylformamide cooled in an ice-water bath under argon is added N-methylmorpholine (164 mg., 1.62 mmole) followed by dicyclohexylcarbodiimide (167 mg., 0.81 mmole). The reaction mixture is refrigerated overnight, then diluted with ethyl acetate and filtered. The organic solution is rinsed with water, saturated sodium bicarbonate solution, and brine, dried over magnesium sulfate, and concentrated in vacuo to give 566 mg. of crude product. Flash chromatography (LPS-1 silica gel, 60 g.) eluting with chloroform:methanol:ammonia (30:2:0.05) gives 270 mg. of $N^2$-[N-[(1,1-dimethylethoxy)carbonyl]-L-phenylalanyl]-N-[(S)-1-[(R)-hydroxy[1[(phenylmethoxy)-methyl]-1H-imidazol-2-yl]methyl]3-methylbutyl]-3'[(phenylmethoxy)methyl]-L-histidinamide;

m.p. 78°–88° ; $[\alpha]_D = -9.2°$ (c=1, methanol). TLC (silica gel; chloroform:methanol: ammonia, 30:2:0.5) $R_f = 0.10$.

Anal. calc'd. for $C_{45}H_{57}N_7O_7$:
C, 66.89; H, 7.11; N, 12.14
Found: C, 66.69; H, 7.18; N, 12.17.

(b) $N^2$-[N-[(1,1-Dimethylethoxy)carbonyl]-L-phenylalanyl]-N-[(S)-1-(R)-hydroxy(1H-imidazol-2-yl)methyl]-3-methylbutyl]-L-histidinamide To a solution of the product from part (a) (255 mg., 0.316 mmole) dissolved in methanol (11.7 ml.) is added water (2.2 ml.), 1N aqueous hydrochloric acid (0.663 ml.) and 20% palladium hydroxide on carbon catalyst (150 mg.). The mixture is stirred under an atmosphere of hydrogen (balloon) for 18 hours. It is then filtered and concentrated in vacuo to give 208 mg. of crude product. Flash chromatography (LPS-1 silica gel, 35 g.) eluting with chloroform:methanol:water: acetic acid (90:20:2.5:1) followed by lyophillization from 1% aqueous acetic acid of the pooled product containing fractions gives 144 mg. of $N^2$-[N-[(1,1-dimethylethoxy)carbonyl]-L-phenylalanyl]-N-[(S)-1-[(R)-hydroxy(1H-imidazol-2-yl)methyl]-3-methylbutyl]-L-histidinamide, acetic acid solvate;

m.p. 194°–196° (dec.); $[\alpha]_D = -8.6°$ (c=0.5, methanol). TLC (silica gel:chloroform: methanol:water:acetic acid, 90:20:2.5:1) $R_f = 0.14$.

Anal. calc'd. for $C_{29}H_{41}N_7O_5 \cdot 1.3\ C_2H_4O_2 \cdot 2.4\ H_2O$:
C, 55.22; H, 7.47; N, 14.36
Found: C, 55.15; H, 7.18; N, 14.31.

EXAMPLE 4

$N^2$-[N-[(1,1-Dimethylethoxy)carbonyl]-L-phenylalanyl]-N-[(S)-1-[(S)-hydroxy(1H-imidazol-2-yl)methyl]-2-phenylethyl]-L-histidinamide, diacetate salt (a) N-[(1,1-Dimethylethoxy)carbonyl]-L-phenylalaninal To a solution of lithium borohydride (940 mg. 43.2 mmole) in dry tetrahydrofuran (90 ml.) cooled in an ice-bath under nitrogen is added a solution containing N-[(1,1-dimethylethoxy)carbonyl]-L-phenylalanine, N-hydroxysuccinimide ester (6.0 g., 16.6 mmole) [prepared according to the procedure of Anderson et al., JACS, Vol. 86, p.1839 (1964)]in tetrahydrofuran (60 ml.). The addition is carried out over a period of 5 minutes. After an additional 20 minutes at 0°, the reaction mixture is poured into 1l. of cold 10% potassium bisulfate. The mixture is extracted with ethyl acetate (4×150 ml) and the combined organic extracts are rinsed with saturated sodium bicarbonate, water, and brine, dried over magnesium sulfate, and concentrated in vacuo to give 3.8 g. of crude product. Flash chromatography (Merck 9385 silica gel, 250 g.) eluting with chloroform:methanol (100:1, 50:1, and finally 25:1) gives 2.4 g. of purified product. Recrystallization from etherhexane gives 1.9 g. of (S)-2-[[(1,1-dimethylethoxy)carbonyl]amino]-2-phenylmethyl-1-ethanol;

m.p. 95°–96° ; $[\alpha]_D = -27.5°$ (c=1, methanol). TLC (silica gel; chloroform:methanol:acetic acid, 25:1:1) $R_f = 0.54$.

Anal. calc'd. for $C_{14}H_{21}NO_3$
C, 66.90; H, 8.42; N, 5.57
Found: C, 67.02; H, 8.49; N, 5.23.

Pyridine sulfur trioxide complex (3.04 g., 19.1 mmole) is added to dry dimethylsulfoxide (7 ml.) under argon and stirred at room temperature for 15 minutes. This mixture is then treated with a mixture of (S)-2-[[(1,1-dimethylethoxy)carbonyl]amino]-2-phenylmethyl-1-ethanol (1.2 g, 4.77 mmole) and diisopropylethylamine (2.47 g., 19.1 mmole) in dry methylene chloride (7 ml.), added rapidly along with the simultaneous application of an ice-water cooling bath. The ice-bath is removed and after 10 minutes the reaction mixture is poured onto a mixture of 50 ml. each of ice-water and ether. The aqueous portion is further extracted with ether (2×50 ml.) and the combined organic extracts are washed with 5% potassium bisulfate, water, saturated sodium bicarbonate, water, and brine, dried over magnesium sulfate, and concentrated in vacuo to give 949 mg. of N-[(1,1-dimethylethoxy)carbonyl]-L-phenylalaninal;

m.p. 71°–80° ; $[\alpha]_D = +37.7°$ (c=1, methylene chloride). TLC (silica gel; petroleum ether:acetone, 3:1) $R_f = 0.45$.

(b) α-[(S)-1-[[(1,1-Dimethylethoxy)carbonyl]amino]-2-phenylethyl]-1(phenylmethoxy)methyl]-1H-imidazole-2-methanol 2.5 M n-Butyllithium solution in hexane (2.8 ml., 6.99 mmole) is added to a solution of 1-[(phenylmethoxy)methyl]-1H-imidazole (1.28 g., 6.82 mmole) in dry tetrahydrofuran (20 ml.) at −70° under argon. After 45 minutes at −70° , a solution of N-[(1,1-dimehylethoxy)carbonyl]-L-phenylalaninal (850 mg., 3.41 mmole) in tetrahydrofuran 4 ml.) is added over a period of several minutes. After 2 hours at −70° , the reaction is warmed to 0° and then quenched by the addition of saturated ammonium chloride (3 ml.). The reaction mixture is then treated with ether (100 ml.) and water (1.5 ml.). The organic extract is rinsed with water (10 ml.) and brine, dried over magnesium sulfate, and concentrated in vacuo to give 2.04 g. of crude product. Flash chromatography (LPS-1 silica gel, 80 g.) eluting with petroleum ether:acetone (3:1 ) gives 234 mg. of α-[(S)-1-[[(1,1-dimethylethoxy)carbonyl]amino]-2-phenylethyl]-1-[(phenylmethoxy)methyl]-1H-imidazole-2-methanol (fast moving isomer), 152 mg. of a mixture fraction, and 294 mg. of a slow moving isomer. TLC (silica gel; petroleum ether:acetone, 2:1) $R_f = 0.13, 0.08$.

(c) $N^2$-[N-[(1,1-Dimethylethoxy)carbonyl]-L-phenylalanyl]-N-[(S)-1-[hydroxy[1-[(phenylmethoxy)methyl]-1H-imidazol-2-yl]methyl]-2-phenylethyl]-3'-[(phenylmethoxy)methyl]-L-histidinamide An approximately (1:1) mixture of the fast and slow moving isomer products from part (b) (512 mg., 1.17 mmole) is dissolved in ethyl acetate (20ml.). The solution is cooled in an ice-water bath and saturated with gaseous hydrogen chloride. The stoppered reaction is kept cold for one hour, and then concentrated in vacuo to 492 mg. of light tan colored α-[(S)-1-amino-2-phenylethyl]-1-[(phenylmethoxy)methyl]-1H-imidazole-2-methanol, dihydrochloride.

This amine salt (1.17 mmole) is heated with 1-hydroxybenzotriazole hydrate (179 mg., 1.17 mmole), N-[N-[(1,1-dimethylethoxy)carbonyl]-L-phenylalanyl]-1'-[(phenylmethoxy)methyl]-L-histidine (611 mg., 1.17 mmole), and dimethylformamide (9 ml.). The above mixture is cooled in an ice-bath under argon and treated with dicyclohexylcarbodiimide (237 mg., 1.17 mmole). The reaction mixture is refrigerated overnight, then diluted with ethyl acetate and filtered. The filtrate is diluted with ether and rinsed with water, saturated sodium bicarbonate, and brine, dried over magnesium sulfate, and concentrated in vacuo to give 882 mg. of crude product. Flash chromatography (LPS-1 silica gel, 120 g.) eluting with chloroform:methanol:ammonia (30:2:0.05) yields 160 mg. of $N^2$-[N-[(1,1-dimethylethoxy)-carbonyl]-L-phenylalanyl]-N-[(S)-1-[hydroxy[1-[(phenylmethoxy)methyl)]-1H-imidazol-2-yl]methyl]-2-phenylethyl]-3'-[(phenylmethoxy)methyl]-L-histidinamide (fast moving isomer), 239 mg. of the slow moving isomer, and about 60 mg. of a mixed fraction. TLC (silica gel; chloroform:methanol: ammonia, 30:2:0.05) $R_f = 0.28, 0.26$. $[\alpha]_D = -25.4°$ (c=1, methanol) for the fast moving isomer and $[\alpha]_D = -29.1°$ (c=1, methanol) for the slow moving isomer.

(d) $N^2$-[N-[(1,1-Dimethylethoxy)carbonyl]-L-phenylalanyl]-N-[(S)-1[(S) hydroxy(1H-imidazol-2-yl)methyl]-2phenylethyl]-L-histidinamine, diacetate salt A mixture of the fast moving isomer from part (c) (157 mg., 0.186 mmole), 20% palladium hydroxide on carbon catalyst (100 mg.), methanol (6.9 ml.), water (1.3 ml.), and 1N aqueous hydrochloric acid (0.391 ml.) is stirred at room temperature under hydrogen (ballon) for 25 hours. The reaction mixture is then filtered and concentrated in vacuo to give 139 mg. of crude product. Flash chromatography (LPS-silica gel, 21 g.) eluting with chloroform:methanol:water: acetic acid (90:20:2.5:1) yields 107 mg. of $N^2$-[N-[(1,1-dimethylethoxy)carbonyl]-L-phenylalanyl]-N-[(S)-1-[(S)-hydroxy(1H-imidazol-2-yl)methyl]-2-phenylethyl]-L-histidinamide, diacetate salt;

m.p. 210°–212° (d); $[\alpha]_D = -21.4°$ (c=0.5, methanol). TLC (Silica gel; chloroform: methanol:water:acetic acid, 90:20:2.5:1) $R_f = 0.09$.

Anal. calc'd. for $C_{32}H_{39}N_7O_5 \cdot 2C_2H_4O_2 \cdot 2\ H_2O$:
C, 57.06; H, 6.78; N, 12.94
Found: C, 57.01; H, 6.50; N, 12.94.

EXAMPLE 5

$N^2$-[N-[(1,1-Dimethylethoxy)carbonyl]-L-phenylalanyl]-N-[(S)-1-[(R)-hydroxy(1H-imidazol-2-yl)methyl]-2-phenylethyl]-L-histidinamide, acetate salt (1:1.5)

A mixture of $N^2$-[N-[(1,1-dimethylethoxy)carbonyl]-L-phenylalanyl]-N-[(S)-1-]hydroxy[1-[(phenylmethoxy)methyl]-1-H imidazol-2-yl]methyl]-2phenylethyl]-3'-[(phenylmethoxy)methyl]-L-histidinamide (slow moving isomer) (236 mg., 0.280 mmole) [prepared in Example 4(c)], 20% palladium hydroxide on carbon catalyst (100 mg.), methanol (10.4 ml.), water (2.0 ml.), and 1N aqueous hydrochloric acid (0.588 ml.) is stirred at room temperature under hydrogen (balloon) for 25 hours. It is then filtered and concentrated in vacuo to give 193 mg. of crude product. Flash chromatography (LPS-1 silica gel, 28 g.) eluting with chloroform:methanol:water: acetic acid (90:20:2.5:1) yields 198 mg. of product. Lyophillization from 1% aqueous acetic acid (polycarbonate filtered) yields 201 mg. of $N^2$-[N-[(1,1-dimethylethoxy)carbonyl]-L-phenylalanyl]-N-[(S)-1-[(R)-hydroxy(1H-imidazol-2-yl)methyl]-2-phenylethyl]-L-histidinamide, acetate salt (1:1.5)

m.p. 196°–217° ; $[\alpha]_D = -30.7°$ (c=0.5, methanol). TLC (silica gel; chloroform: methanol:water:acetic acid, 90:20:2.5:1) $R_f = 0.09$.

Anal. calc'd. for $C_{32}H_{39}N_7O_5 \cdot 1.5\ C_2H_4O_2 \cdot 2.2\ H_2O$:
C, 57.47; H, 6.81; N, 13.41
Found: C, 57.47; H, 6.47; N, 13.40.

EXAMPLE 6

$N^2$-[N-[(1,1-Dimethylethoxy)carbonyl]-L-phenylalanyl]-N-[(1S)-2-cyclohexyl-1-[(S)-hydroxy-1H-imidazol-2-ylmethyl]ethyl]-L-histidinamide, monoacetate salt (a) (S)-2 -[[(1,1-Dimethylethoxy)carbonyl]amino]-2-phenylmethyl-1-ethanol To a solution containing N-[(1,1-dimethylethoxy)carbonyl]-L-phenylalanine (10 g., 37.7 mmole) in dimethylformamide (40 ml.) is added solid sodium bicarbonate (4.75 g., 56.6 mmole) and iodomethan (16 g., 113 mmole). The mixture is heated at 40° under argon for 12 hours, the cooled and the reaction mixture partitioned between water (150 ml.) and ether (250 ml.). The organic layer is rinsed with 2% aqueous sodium bicarbonate (2×100 ml.), 2% aqueous sodium bisulfite (100 ml.), water (2×100 ml.), and brine, dried over magnesium sulfate, and concentrated in vacuo to give 10.5 g. of N-[(1,1-dimethylethoxy)carbonyl]-L-phenylalanine, methyl ester as an oil; $[\alpha]_D = +47.7°$, methylene chloride) TLC (silica gel; petroleum ether:acetone, 6:1)$R_f=0.41$.

Anal. calc'd. for $C_{15}H_{21}NO_4$:
C, 64.49; H, 7.58; N, 5.01
Found: C, 64.56; H, 7.60; N, 5.29.

To a solution containing N-[(1,1-dimethylethoxy)carbonyl]-L-phenylalanine, methyl ester (10 g., 35.8 mmole) dissolved in a mixture of tetrahydrofuran (190 ml.) and absolute ethanol (190 ml.) is added lithium chloride (6.09 g., 143.2 mmole). The resulting homogenous solution is treated with sodium borohydride (b 5.42 g., 143.2 mmole) and the reaction is stirred at room temperature under argon for 24 hours. The reaction mixture is next filtered using ether (about 700 ml.) to rinse the filter cake. The resulting filtrate is rinsed with water (3×200 ml.) and brine (200 ml.), dried over magnesium sulfate, and concentrated in vacuo to give 9 g. of crude product. Recrystallization from ether/hexane gives 7.59 g. of (S)-2-[[(1,1-dimethylethoxy)carbonyl]amino]-2-phenylmethyl-1-ethanol;

m.p. 94°-96°; $[\alpha]_D = -27.2°$ (c=1, methanol). TLC(silica gel; petroleum ether:acetone, 3:1) $R_f=0.39$.

Anal. calc'd. for $C_{14}H_{21}NO_3$:
C, 66.90; H, 8.42; N, 5.57
Found: C, 66.80; H, 8.57; N, 5.38.

(b) [(S)-2-Cyclohexyl-1-hydroxymethyl)ethyl]-carbamic acid, 1,1-dimethylethyl ester A solution of (S)-2-[[(1,1-dimethylethoxy)carbonyl]amino]-2-phenylmethyl-1-ethanol (7 g., 27.8 mmole) in methanol (70 ml.) is hydrogenated at 55 psi on a Parr Shaker using 5% rhodium on alumina (500 mg.) as catalyst. After 17 hours, the reaction mixture is filtered and concentrated in vacuo to yield 7.36 g. of [(S)-2-cyclohexyl-1-(hydroxymethyl)ethyl]carbamic acid, 1,1-dimethylethyl ester as an oil; $[\alpha]_D = -23.3°$ (c=1, methylene chloride). TLC (silica gel; petroleum ether:acetone, 3:1) $R_f=0.5$.

Anal. calc'd. for $C_{14}H_{27}NO_3$:
C, 65.33; H, 10.57; N, 5.44
Found: C, 64.94; H, 10.55; N, 5.23.

(c) (S)-(2-Cyclohexyl-1-formylethyl)carbamic acid, 1,1-dimethylethyl ester

A solution of [(S)-2-cyclohexyl-1-hydroxymethyl)ethyl]carbamic acid, 1,1-dimethylethyl ester (4.6 g., 17.9 mmole) in methylene chloride (40 ml.) is added to a mixture of Dess-Martin periodinane reagent (8 g., 19 mmole) [prepared according to Dess et al., J. Org. Chem., Vol. 48, p. 4155 (1983)] and t-butanol (1.5 g., 19 mmole) in methylene choloride (70 ml.) which had been stirred at room temperature before the addition. A slight exotherm (to 32°) results. After 30 minutes, the reaction mixture is quenched in ether (800 ml.), resulting in the separation of a white solid. A mixture of sodium thiosulfate pentahydrate (31.3 g., 126 mmole) in saturated sodium bicarbonate solution (200 ml.) is added, with stirring. The resulting two-phase mixture is separated and the organic phase is washed with water, saturated sodium bicarbonate (2×100 ml.), water, and brine, dried over magnesium sulfate, and concentrated in vacuo to give 3.8 g. of (S)-(2-cyclohexyl-1-formylethyl)carbamic acid, 1,1-dimethylethyl ester as a colorless oil.

(d) [(1S)-1-(Cyclohexylmethyl)-2-hydroxy-2-[1-[(phenylmethoxy)methyl]-1H-imidazol-2-yl]ethyl]carbamic acid, 1,1-dimethylethyl ester 2.5 M n-Butyllithium solution in hexane (12 ml., 31 mmole) is added to a solution of 1-[(phenylmethoxy)methyl]-1H-imidazole (5.3 g., 28 mmole) in tetrahydrofuran (90 ml.) at −70° under argon. After stirring for 15 minutes, (S)-(2-cyclohexyl-1-formylethyl)carbamic acid, 1,1-dimethylethyl ester (3.6 g., 14 mmole) in tetrahydrofuran (36 ml.) is added dropwise over a period of 5 minutes at a reaction temperature of −65° to −70°. After 2 hours at −70°, the bath is warmed to 0° and saturated ammonium chloride (25 ml.) is added followed by ether (300 ml.) and water (25 ml.). The organic phase is washed with water (2×50 m.) and brine, dried over magnesium sulfate, and concentrated in vacuo. The resulting crude product (8.4 g.) is flash chromatographed (LPS-1silica gel) eluting with acetone:petroleum ether (1:4) to give 580 mg. of [(1S)-1-(cyclohexylmethyl)-2-hydroxy-2-[1-[(phenylmethoxy)methyl]-1H-imidazol-2-yl]ethyl]carbamic acid, 1,1-dimethylelthyl ester (fast moving isomer), 370 mg. of a mixed fraction, and 2 g. of a slow moving isomer. TLC (silica gel; acetone:petroleum ether 1:4) $R_f=0.15, 0.10$.

Fast moving isomer; $[\alpha]_D = -21.5°$ (13 mg./ml., methanol).

Anal. calc'd. for $C_{25}H_{37}N_3O_4$. 0.4 $H_2O$:
C, 66.61; H, 8.45; N, 9.32
Found: C, 66.55; H, 8.39; N, 9.00.

Slower moving isomer; $[\alpha]_D = -9.1°$ (14mg./ml., methanol).

Anal. calc'd. for $C_{25}H_{37}N_3O_4$. 0.22$H_2O$:
C, 67.08; H, 8.43; N, 9.39
Found: C, 67.08; H, 8.35; N, 9.01.

(e) $N^2$[N-[(1,1-Dimethylethoxy)carbonyl]-L-phenylalanyl]-N-[(S)-1-[(S)-hydroxy[1-[(phenylmethoxy)methyl]-1H-imidazol-2-yl]methyl]2-cyclohexylethyl]-3'-[(phenylmethoxy)methyl]-L-histidinamide A solution of the fast moving isomer from part (d) (430 mg., 0.97 mmole) in ethyl acetate (8 ml.) is cooled in an ice-water bath and saturated with gaseous hydrogen chloride. After remaining in the cold for 15 minutes, the mixture is kept in a stoppered flask at ambient temperature for 45 minutes. The mixture is concentrated in vacuo to give 384 mg. of the amine dihydrochloride salt.

This amine salt (306 mg., 0.8 mmole) is dissolved in dry dimethyformamide (6 ml.) and N-[N-[(1,1-dimethylethoxy)carbonyl]-L-phenylalanyl]-1'-[(phenylmethoxy)methyl]-L-histidine (442 mg., 0.8 mmole) is added followed by 1-hydroxybenzotriazole hydrate (122 mg., 0.8 mmole) and N-methylmorpholine (160 mg., 1.6 mmole). After cooling in an ice-water bath, dicyclohexycarbodiimide is added. The mixture is stirred in the cold for 15 minutes and then refrigerated overnight in a stoppered flask. The solids that separate from the solution are recovered by filtration after the mixture is diluted to a volume of 45 ml. with ether. The filtrate is washed with water, saturated sodium bicarbonate solution, and brine, dried over magnesium sulfate, and concentrated in vacuo to give a viscous oil residue (587 ml.). This residue is preabsorbed on silica gel (Baker's, 3 g.) and flash chromatographed (LPS-1 silica gel, 90 g.) eluting with chloroform:methanol:concentrated ammonium hydroxide (30:2:0.05) to give recovery of the product in two fractions (333 mg. of impure and 70 mg. of pure product). The impure fraction is rechromatographed as above to give a recovery of 206 mg. This is combined with the 70 mg. fraction and chromatographed again according to the above procedure to give 255 mg. of N²-[N-[(1,1-dimethylethoxy)-carbonyl]-L-phenylalanyl]-N-[(1S)-1-[(S)-hydroxy-[1-[(phenylmethoxy)methyl]-1H-imidazol-2-yl]methyl]-2-cyclohexylethyl]-3'-[(phenylmethoxy)methyl]-L-histidinamide as a glassy solid;

m.p. 74°-77° (gradual melt); $[\alpha]_D = -24.3°$ (c=1, methanol). TLC (silica gel; chloroform: methanol:conc. ammonium hydroxide, 30:2:0.05) $R_f = 0.17$ Anal. calc'd. for $C_{48}H_{61}N_7O_7 \cdot 1H_2O$: $H_2O$:
C, 66.57; H, 7.33; N, 11.32
Found: C, 66.55; H, 7.26; N, 11.37.

(f) N²-[N-[(1,1-Dimethylethoxy)carbonyl]-L-phenylalanyl]-N-[(1S)-2-cyclohexyl-1-[(S) -hydroxy-1H-imidazol2-ylmethyl]ethyl]-L-histidinamide, monoacetate salt A mixture of the product from part (e) (242 mg., 0.28 mmole) and 20% pallaium hydroxide on carbon catalyst (85 mg.) in methanol (6 ml.) plus water (0.61 ml.) and 1N hydrochloric acid (0.62 ml., 0.62 mmole) is stirred at room temperature in an atmosphere of hydrogen (balloon) for 60 hours. An additional 100 mg. of catalyst and 4 ml. of methanol are added and the mixture is stirred in an atmosphere of hydrogen for 20 hours. After filtrating through Celite, the filtrate is concentrated in vacuo to give 200 mg. of a glassy solid residue. This residue is then flash chromatographed (LPS-1silica gel, 40 g.) eluting with chloroform:methanol:water:acetic acid (90:20:2.5:1) to give 120 mg of a glassy solid that is lyophillized from 3% acetic acid to give 120 mg. of an amorphous white solid. This solid is rechromatographed (LPS-1silica gel, 16 g.) eluting with chloroform:methanol:water:acetic acid (90:20:2.5:1) to give 6.94 mg. of N²-[N-[(1,1-dimethylethoxy)carbonyl]-L-phenylalanyl]-N-[(1S)-2-cyclohexyl-1-[(S)-hydroxy-1H-imidazol-2 -ylmethyl]ethyl]-L-histidinamide, monoacetate salt: m.p. 162° (gradual melt, shrinks at 110° ); $[\alpha]_D = -35.6°$ (5 mg./ml., methanol). TLC (silica gel; n-butanol:pyridine:acetic acid:water, 4:1:1:1) $R_f = 0.61$ .

Anal. calc'd. for $C_{32}H_{45}N_7O_5 \cdot 1 \, C_2H_4O \cdot 2.65 \, H_2O$:
C, 57.07; H, 7.65; N, 13.70
Found: C, 57.05; H, 7.40; N, 13.72.

EXAMPLE 7

N²-[N-[(1,1-Dimethylethoxy)carbonyl]-L-phenylalanyl]-N-[(1S)-2-cyclohexyl-1-[(R)-hydroxy-1H-imidazol-2-ylmethyl]ethyl]-L-histidinamide, monoacetate salt (a) N²-[N-[(1,1-Dimethylethoxy)carbonyl]-L-phenylalanyl]-N-[(1S)-1-[(R)-hydroxy[1-[(phenylmethoxy)methyl]-1H-imidazol-2-yl]methyl]-2-cyclohexylethyl]-3'-[(phenylmethoxy)methyl]-L-histidinamide A solution of [(1S)-1-(cyclohexylmethyl)-2-hydroxy-2-[1-[(phenylmethoxy)methyl]-1H-imidazol-2-yl]ethyl]-carbamic acid, 1,1-dimethylethyl ester (slow moving isomer) (467 mg., 1.05 mmole) [prepared in Example 6 (d)]in ethyl acetate (25 ml.) is cooled in an ice-water bath under argon and saturated with gaseous hydrogen chloride. The stoppered reaction is kept cold for one hour and then concentrated in vacuo to give 467 mg. of the amine dihydrochloride salt.

This amine salt (374 mg., 0.84 mmole) is dissolved in dimethylformamide (6 ml.) along with N-[N-[(1,1-dimethylethoxy)carbonyl]-L-phenylalanyl]-N-1'-[(phenylmethoxy)methyl-]-L-histidine (439 mg., 0.84 mmole) and 1-hydroxybenzotriazole hydrate (128 mg., 0.84 mmole). The mixture is cooled under argon in an ice-water bath and treated with N-methylmorpholine (170 mg., 1.68 mmole) followed by dicyclohexycarbodiimide (173 mg., 0.84 mmole). The stoppered reaction mixture is refrigerated overnight, then filtered and extracted with ethyl acetate. The organic solution is rinsed with water, saturated sodium bicarbonate, water, and brine, dried over magnesium sulfate, and concentrated in vacuo to 730 mg. of crude product. Flash chromatography (LPS-1silica gel, 70 g.) eluting with chloroform:methanol: concentrated ammonia (30:2:0.05) gives 271 mg. of N-hu 2-[N-[(1,1-dimethylethoxy)carbonyl]-L-phenylalanyl]-N-[(1S)-1-[(R)-hydroxy[1-[(phenylmethoxy)methyl]-1H-imidazol-2-yl]methyl]-2-cyclohexylethyl]-3'-[(phenylmethoxy)methyl]-L-histidinamide; $[\alpha]_D = -8.7°$ (c=1, methanol). TLC silica gel; chloroform:methanol:conc. ammonia, 30:2:0.05) $R_f = 0.14$ .

Anal. calc'd. for $C_{48}H_{61}N_7O_7$ :
C, 67.98; H, 7.25; N, 11.56
Found: C, 67.80; H, 7.27; N, 11.44 .

(b) N²-[N-[(1,1-Dimethylethoxy)carbonyl]-L-phenylalanyl]-N-[(1S)-2-cyclohexyl-1-[(R)-hydroxy-1H-imidazol-2-ylmethyl]ethyl]-L-histidinamide monoacetate salt The product from part (a) (265 mg., 0.312 mmole) is dissolved in methanol (11.6 ml.) to which is added water (2.2 ml.) followed by 1N aqueous hydrochloric acid (0.66 ml.) and 20% palladium hydroxide on carbon catalyst (100 mg.). The mixture is stirred under a hydrogen atmosphere (balloon) for 17 hours, then filtered and concentrated in vacuo to give 250 mg. of crude product. Flash chromatography (LPS-1silica gel, 35 g.) eluting with chloroform:methanol:water (tap distilled):acetic acid (90:20:2.5:1) followed by lyophillization of the product containing fractions gives 186 mg. of material. Rechromatography using double distilled water (LPS-1 silica gel, 20 g.) eluting with the 90:20:2.5:1 solvent system gives 95 mg. of N²-[N-[(1,1-dimethylethoxy)carbonyl]-L-phenylalanyl]-N-[(1S)-2-cyclohexy-1-[(R)-hydroxy-1H-imidazol-2-ylmethyl]ethyl]-L-histidinamide, monoacetate salt;

m.p. 193°-197° (d 200°); $[\alpha]_D = -19°$ (c=0.5, methanol) TLC (silica gel; chloroform:methanol:water:acetic acid, 90:20:2.5:1) $R_f = 0.07$.

Anal. calc'd. for $C_{32}H_{45}N_7O_5 \cdot 0.8 \, C_2H_4O \cdot 1.4 \, H_2O$:
C, 59.26; H, 7.55; N, 14.40
Found: C, 59.24; H, 7.49; N, 14.37.

N-[(1S)-2-Cyclohexyl-1-[(R)-hydroxy(1H-imidazol-2-yl)methyl]ethyl]-N²-[N-[(1,1-dimethylethoxy)carbonyl]-L-phenylalanyl]-L-leucinamide, acetate salt (a) N-[N-[(1,1-Dimethylethoxy)carbonyl]-L-phenylalanyl]-L-leucine, methyl ester A solution of diisopropylethylamine (8.7 ml., 50 mmole) in tetrahydrofuran (50 ml.) is added dropwise to a mixture of N-[(1,1-dimethylethoxy) carbonyl]-L-phenylalanine (13.265 g., 50 mmole), L-leucine, methyl ester (9.085 g., 50 mmole) and 1-hydroxybenzotriazole hydrate (7.65 g., 50 mmole) in tetrahydrofuran (100 ml.) at 0°. This is followed by the addition of dicylcohexyl-carbodiimide (10.315 g., 50 mmole). The reaction is stirred at 0°for 2 hours and left stirring overnight at room temperature. The nexy day, the precipitated dicyclohexyl urea is filtered off, the solvents are stirred down and the residue is diluted with ethyl acetate (200 ml.). The organic solution is washed sequentially with saturated aqueous sodium bicarbonate solution (2×100 ml.) and saturated aqueous sodium chloride (2×100 ml.), dried over sodium sulfate, filtered, and concentrated to give crude product. Crystallization from ethyl ether gives 7.05 g. of pure product. Concentration of the mother liquor solutions gives 4.57 g. of crystalline product. An additional 1.35 g. of product is obtained by chromatographic purification of the crude product obtained from the left-over mother liquors (40 g. silica gel, eluting with 4:1 hexane:ethyl acetate). Thus, a total of 12.96 g. of N-[N-[(1,1-dimethylethoxy)carbonyl]-L-leucine, methyl ester is obtained;

m.p. 104°–105°; $[\alpha]_D = -17.5°$ ($c = 1.2$, methanol). TLC (silica gel; hexane: ethyl acetate, 1:1) $R_f = 0.57$.

Anal. calc'd. for $C_{21}H_{32}N_2O_5$:
C, 64.30; H, 8.15; N, 7.14
Found: C, 64.12; H, 8.16; N, 7.02.

(b) N-[(1S)-2-Cyclohexyl-1-[(R)-hydroxy[1-[(phenylmethoxy)methyl]-1H-imidazol-2-yl]methyl]ethyl]-N$^2$-[N-[(1,1-dimethylethoxy)carbonyl]-L-phenylalanyl]-L-leucinamide The methyl ester product from part (a) (1.176 g., 3 mmole) in tetrahydrofuran (12 ml.) is treated with aqueous 1N sodium hydroxide (3.3 ml., 3.3 mmole). After two hours at room temperature, the mixture is refluxed for two hours. The solvents are stirred down and the residue is taken up in water, acidified, and extracted with ethyl acetate. The organic layer is dried over sodium sulfate and concentrated to give a residue which is resubjected to hydrolysis with aqueous 1N sodium hydroxide (1.5 ml., 1.5 mmole) in methanol (12 ml.). After three hours at room temperature, the solvents are stripped down. The residue is taken up in water (100 ml.), extracted with ethyl acetate (2×25 ml.), and the organic layer is discarded. The aqueous layer is carefully acidified (pH 3.9), extracted with ethyl acetate (3×25 ml.), dried over sodium sulfate and concentrated to give 735 mg. of N-[N-(1,1-dimethylethoxy)carbonyl]-L-phenylalanyl]-L-leucine To a mixture of this acid (753 mg., 2.0 mmole), [(1S)-1-(cyclohexylmethyl)-2-hydroxy-2-[1-[(phenylmethoxy)methyl]-1H-imidazol-2-yl]ethyl]-carbamic acid, 1,1-dimethylethyl ester, slow isomer from Example 6(d) (887 mg., 2.0 mmole), and 1-hydroxybenzotriazole hydrate (306 mg., 2.0 mmole) in tetrahydrofuran (8 ml.) at 0° is added diisopropylethylamine (731 μl., 4.2 mmole) followed by dicyclohexylcarbodiimide (416 mg., 2.0 mmole). The reaction mixture is stirred at 0° for about 2 hours and then kept overnight in the cold room (about 5°). The next day, the precipitated dicyclohexyl urea is filtered off and the residue is redissolved in ethyl acetate, washed with saturated aqueous sodium bicarbonate solution (2×30 ml.) and saturated aqueous sodium chloride (2×30 ml.), dried over sodium sulfate, filtered, and concentrated to give 1.339 g. of a crude residue. Repeated flash chromatographies (silica gel, eluting with 9:1:0.1 and 15:1:0.05 chloroform:methanol:acetic acid) gives 1.021 g. of N-[(1S)-2-cyclohexyl-1-[(R)-hydroxy[1-[(phenylmethoxy)methyl]-1H-imidazol-2-yl]methyl]ethyl]-N$^2$-[N-[(1,1-dimethylethoxy)carbonyl]-L-leucinamide. TLC (silica gel; chloroform:methanol:acetic acid, 9:1:0.1) $R_f = 0.5$.

(c) N-[(1S)-2-Cyclohexyl-1-[(R)-hydroxy(1H-imidazol-2-yl)methyl]ethyl]-N$^2$-[N-[(1,1-dimethylethoxy)carbonyl]-L-phenylalanyl]-L-leucinamide, acetate salt 20% palladium hydroxide on carbon catalyst (100 mg.) is weighed in a side arm flask and flushed with hydrogen using a balloon. The L-leucinamide product from part (b) (295 mg., 0.42 mmole) is added via a syringe as a solution in methanol (5 ml.). This is followed by sequential addition of methanol (8.5 ml.), water (3.0 ml.), and aqueous 10% hydrochloric acid (0.037 ml.). The flask is then carefully flushed several times with hydrogen and stirred overnight at room temperature. The contents of the flask are filtered and the filtrate is concentrated. The resulting residue is flash chromatographed (30 g. of silica gel; eluting with 90:10:1:0.1 chloroform:methanol: water:acetic acid) to give 155.3 mg. of N-[(1S)-2-cyclohexyl-1-[(R)-hydroxy(1H-imidazol-2-yl)methyl]ethyl]-N$^2$-[N-[(1,1-dimethylethoxy)carbonyl]-L-phenylalanyl]-L-leucinamide, acetate salt;

m.p. 101°–109° (gradual melting); $[\alpha]_D = -25.7°$ ($c = 1.06$, methanol). TLC (silica gel; chloroform: methanol:water:acetic acid, 90:20:2.5:0.1) $R_f = 0.21$.

Anal. calc'd. for $C_{32}H_{49}N_5O_5 \cdot 0.9\ C_2H_4O_2 \cdot 0.75\ H_2O$:
C, 62.33; H, 8.37; N, 10.75
Found: C, 62.83; H, 8.17; N, 10.75.

EXAMPLE 9

N-[(1S)-1-(Cyclohexylmethyl)-2(R)-hydroxy-2-(1H-imidazol-2-yl)ethyl]-N$^2$-[N-[(1,1-dimethylethoxy)carbonyl]-L-phenylalanyl]glycinamide, acetate salt (a) N-[N-[(1,1-Dimethylethoxy)carbonyl]-L-phenylalanyl]glycine, ethyl ester To a mixture of N-[(1,1-dimethylethoxy)carbonyl]-L-phenylalanine (13.265 g., 50 mmole), glycine, ethyl ester, monohydrochloride (6.98 g., 50 mmole), and 1-hydroxybenzotriazole hydrate (7.65 g., 50 mmole) in tetrahydrofuran (100 ml.) at 0° is added dicyclohexylcarbodiimide (10.315 g., 50 mmole) as a solution in tetrahydrofuran (25 ml.). This is followed by the addition of a solution of diisopropylethylamine (8.7 ml., 50 mmole) in tetrahydrofuran (25 ml.). The reaction is stirred at 0° C. for 2 hours and then stirred overnight at room temperature. The next day, the precipitated dicyclohexyl urea is filtered off and the solvents stripped down. The residue is diluted with ethyl acetate (200 ml.) and the resulting organic solution is washed sequentially with saturated aqueous sodium bicarbonate solution (2×100 ml.) and saturated aqueous sodium chloride (100 ml.), dried over sodium sulfate, filtered, and concentrated. The resulting crude material is crystalized from ethyl ether to give 9.45 g. of pure product. Concentration of the mother liquor solution to half its original volume gives an additional 3.7 g. of N-[N-[(1,1-dimethylethoxy)carbonyl]-L-phenylalany]glycine, ethyl ester;

m.p. 90°–92°; $[\alpha]_D = -9.1°$ ($c = 1.41$, methanol).
Anal. calc'd. for $C_{18}H_{26}N_2O_5$:
C, 61.73; H, 7.42; N, 7.99
Found: C, 61.64; H, 7.46; N, 8.07.

(b) N-[(1S)-1-(Cyclohexylmethyl)-2-hydroxy2-[1-[(phenylmethoxy)methyl]-1H-imidazol-2-yl]ethyl]-N$^2$-[N-[(1,1-dimethylehoxy)carbonyl]-L-phenylalanyl]-glycinamide A solution of the ethyl ester product from part (a) (1.05 g., 3.0 mmole) in tetrahydrofuran (12 ml.) is treated with aqueous 1N sodium hydroxide (3.1 ml., 3.1 mmole). Hydrolysis is found to be complete after 2 hours at room temperature. The solvents are stripped down and the residue is taken up in saturated aqueous sodium bicarbonate solution (15 ml.) and extracted with ether (30 ml.). Some sodium salt precipitates at this stage and is filtered and separated from the biphasic layer. The ethereal layer is discarded. The aqueous layer is carefully acidified (pH 5.0 and finally 2.5) and reextracted with ethyl acetate (3×20 ml.). The precipitated sodium salt is taken up in water, the aqueous solution is acidified (pH 2.5), and extracted with ethyl acetate (3×20 ml.). The combined organic extract is dried over sodium sulfide, filtered, and concentrated to give 599 mg. of N-[N-[(1,1-dimethylethoxy)carbonyl]-L-phenylalanine[glycine.

To a mixture of the above acid (plus an added amount from a small scale run) (644 mg., 2.0 mmole) and [(1S)-1-(cyclohexylmethyl)-2-hydroxy-2-[ 1-(phenylmethoxy)methyl]-1H-imidazol-2-yl]ethyl]carbamic acid, 1,1-dimethylethyl ester, slow isomer from Example 6 (d) (887 mg., 2.0 mmole) in dimethylformamide (8 ml.) at 0° is added 1-hydroxybenzotriazole hydrate (306 mg., 2.0 mmole), diisopropylethylamine (731 µl., 4.2 mmole), and finally dicyclohexylcarbodiimide (420 mg., 2.0 mmole). The reaction mixture is stirred for 2 hours at 0° and then overnight at room temperature. The next day, the precipitated dicyclohexyl urea is filtered off, and the filtrate is concentrated. The residue is taken up in ethyl acetate (75 ml.) and washed sequentially with water (2×25 ml.), saturated aqueous sodium bicarbonate (2×25 ml.), amd saturated aqueous sodium chloride (25 ml.), dried over sodium sulfate, and concentrated to give 838 mg. of crude product. Repeated chromatographic purifications (silica gel, eluting with 19:1 chloroform:methanol) gives 113 mg. of N-[(1S)-1-cyclohexylmethyl-2(R)-hydroxy-2-[1(phenylmethoxy)methyl]-1H-imidazol-2-yl]ethyl]-$N^2$-[N-[(1,1-dimethylethoxy)-carbonyl]-L-phenylalanyl]glycinamide. TLC (silica gel; chloroform:methanol: acetic acid, 9:1:1) $R_f$=0.3.

Anal. calc'd. for $C_{36}H_{49}N_5O_6$:
C, 66.81; H, 7.62; N, 10.81
Found: C, 64.49; H, 7.41; N, 10.02.

(c) N-[(1S)-1-(Cyclohexylmethyl)-2(R)-hydroxy-2-(1H-imidazol-2-yl)ethyl]-$N^2$-[N-[(1,1-dimethylethoxy)-carbonyl]-L-phenylalanyl]glycinamide, acetate salt 20% palladium hydroxide on carbon catalyst (100 mg.) is weighed in a side arm flask and flushed with hydrogen using a balloon. The glycinamide product from part (b) (113 mg., 0.2 mmole) is added as a 2 ml. methanol solution. This is followed by the sequential addition of methanol (6 ml.), water (2 ml.) and 10% aqueous hydrochlowic acid (145 µl.). The reaction mixture is stirred at room temperature for several days. The catalyst is removed by filtration and the filtrate is concentrated to give a crude product which after repeated chromatographic separations (silica gel, eluting with chloroform:methanol:water:acetic acid, 90:20:2.5:1) yields 9.5 mg. of N-[(1S)-1-(cyclohexylmethyl)-2(R)-hydroxy-2-(1H-imidazol-2-yl)ethyl]-$N^2$-[(1,1-dimethylethoxy)carbonyl]-L-phenylalanine]glycinamide, acetate salt;

m.p. 99°-100°; $[\alpha]_D$= −7.0° (c=0.1, methanol). TLC (silica gel; chloroform:methanol:water:acetic acid, 90:20:2.5:1) $R_f$=0.27.

Anal. calc'd. for $C_{28}H_{41}N_5O_5$. 0.7 $C_2H_4O_2$. 1.0 $H_2O$:
C, 60.16; H, 7.86; N, 11.92
Found: C, 60.06; H, 7.64; N, 11.93.

EXAMPLE 10

$N^2$-[N-[(1,1-Dimethylethoxy)carbonyl]-L-phenylalanyl]-N-[(S)-1-[(R)-hydroxy(2-thiazolyl)methyl]-3-methylbutyl]-L-histidinamide, acetate salt (a) (2S)-2-[[(1,1-Dimethylethoxy)carbonyl]amino]-4-methyl-1-(2-thiazolyl)-1-pentanol 2.5 n-Butyllithium in hexane (8 ml.) is added to a solution containing thiazole (1.7 g., 20 mmole) in dry tetrahydrofuran (60 ml.) cooled to −70° under argon. After stirring a short time, the solid material begins to come out of solution. The reaction remains heterogeneous after 35 minutes at −40° to −35°. After cooling the reaction to −50°, a solution containing N-[(1,1-dimethylethoxy)carbonyl]-L-leucinal (2.2g., 10 mmole) in tetrahydrofuran (5 ml.) is added. After 90 minutes the reaction is warmed to −10° and quenched with saturated ammonium chloride (10 ml.). The reaction mixture is extracted into ether and the organic extract is rinsed with water and brine, dired (MgSO4) and concentrated in vacuo to give 1.8 g. of amide product. Two flash chromatographies on first 100 g. and then 150 g. of silica gel (LPS-1) eluting with petroleum ether:acetone (20:1 ) fails to remove a minor impurity from the co-eluting desired diastereimeric product mixture. A total of 1.2 g. of (2S)-2-[[(1,1-dimethylethoxy)carbonyl-]amino]-4-methyl-1-(2-thiazolyl)-1-pentanol is obtained. TLC (silica gel; petroleum ether:acetone, 4:1) $R_f$=0.37. 8 $\alpha]_D$= −38.6° (c=1, chloroform).

(b) [(1,1-Dimethylethoxyecarbonyl]-$N^1$-(2,4 dinitrophenyl)-N-[(S)-1[-(R)-hydroxy(2thiazolyl)methyl]-3methylbutyl]-L-histinamide A solution of the product from part (a) (1.5 g., 5 mmole) dissolved in ethyl acetate (40 ml.) is cooled in an ice water bath under argon. After saturating with dry HCl gas, the removal of the ethyl acetate in vacuo, trituration of the residue gives 1.45 g. of crude bis hydrochloride salt.

This bis hydrochloride salt (860 mg., 3.15 mmole), N-[(1,1-dimethylethoxy)carbonyl]-$N^1$-(2,4 -dinitrophenyl)-L-histidine (1.38 g., 3.15 mmole), and 1-hydroxybenzotriazole hydrate (482 mg., 3.15 mmole) are stirred in tetrahydrofuran (30 ml.) under argon, cooled in an ice water bath, and treated with N-methylmorpholine (637 mg., 6.3 mmole) folowed by dicyclohexyxcarbodiimide (650 mg., 3.15 mmole). The reaction is stirred in the ice bath for an hour, refrigerated overnight, and then filtered. The filtrate is diluted with ethyl acetate. The organic extract is rinsed with water, saturated sodium bicarbonate, and brine, dried (MgSO4), and concentrated in vacuo to give 1.82 g. of crude product. Flash chromatography on silica gel (170., LPS-1) eluting with chloroformd methanol (20:1) yields 0.46 of fast moving isomer (S), 0.57 g. of a mixture of isomers, and 0.27 g. of slow moving isomer (R). Rechromatographing the mixture fraction gives a total of 0.54 g. of (S) isomer and 0.80 g. of [(1,1dimethylethoxy)carbonyl]-$N^1$-(2,4 -dinitrophenyl)-N-[(S)-1-[(R)-hydroxy(2-thiazolyl)methyl]-3-methylbutyl]-L-histidinamide;

m.p. 82°-107°. TLC (silica gel; chloroform:methanol 20:1) $R_f$=0.15. $[\alpha]_D$= −12.7° (c=1, methylene chloride).

(c) $N^2$-N-[N-[(1,1Dimethylethoxy)carbonyl]-L-phenylalanyl]-N-[(S)-1-[(R)-hydroxy(2-thiazolyl)methyl]-3-methylbutyl]-$N^1$-(2,4-dinitrophenyl)-L-histidinamide A solution containing the (R) hydroxy isomer product from part (b) (510 mg., 0.84 mmole) in ethyl acetate (25 ml.) is cooled in an ice water bath and saturated with dry HCl. After stirring for 60 minutes, the solvent is removed in vacuo to yield 436 mg. of $N^1$-(2,4 -dinitrophenyl)-N-[(S)-1-[(R)-hydroxy(2-thiazolyl)methyl]-3-methylbutyl]-L-histidinamide, hydrochloride salt.

This crude hydrochloride salt (436 mg., 0.46 mmole), N-[(1,1-dimethoxyethoxy)carbonyl]-L-phenylalanine (122 mg., 0.46 mmole), and 1-hydroxybenzotriazole hyrdate (70 mg., 0.46 mmole) are stirred in tetrahydrofuran (10 ml.) under argon, cooled to 0° and treated with N-methylmorpholine (118 mg., 1.15 mmole) followed by dicyclohexylcarboiimide (95 mg., 0.46 mmole). The reaction is allowed to warm to room temperature overnight, then filtered and diluted with ethyl acetate and ether. The organic extract is rinsed with water, saturated sodium bicarbonate, and brine, dried ($MgSO_4$), and concentrated in vacuo to give 360 mg. of crude product. Flash chromatography on silica gel (40 g., LPS-1) eluting with chloroform:methanol (20:1 ) yields 250 mg. of $N^2$-[N-[(1,1-dimethylethoxy)carbonyl]-L-phenylalanyl]-N-[(S)-1-[(R)-hydroxy(2-thiazolyl)methyl]-3-methylbutyl]-$N^l$-2,4-dinitrophenyl)-L-histidinamide, m.p. 100°-115° ; $[\alpha]_D = -25.5°$ (c=1, chloroform). TLC (silica gel; chloroform:methanol, 10:1) $R_f$=0.32.

Anal. calc'd. for $C_{35}H_{42}N_8O_9S \cdot 1.5 H_2O$:

C, 54.04; H, 5.83; N, 14.41; S, 4.12

Found: C, 53.99; H, 5.59; N, 13.97; S, 4.18.

(d) $N^2$-[N-[(1,1-Dimethylethoxy)carbonyl]-L-phenylalanyl]-N-[(S) -1-[(R)-hydroxy(2-thiazolyl)methyl]-3-methylbutyl]-L-histidinamide, acetate salt Mercaptoacetic acid (1.15 g., 12.5 mmole) is added to a solution of the product from part (c) (243 mg., 0.324 mmole) in dimthylformamide (3ml.) under argon. After 2 hours at room temperature, the reaction is extracted into a mixture of ethyl acetate (40 ml.) and ether (20 ml.), rinsed with seven 10 ml. portions of 10% aqueous sodium carbonate, three 10 ml. portions of water, and brine. The organic extract is dried ($MgSO_4$) and concentrated in vacuo to 0.26 g. of crude product. Flash chromatography on silica gel (25 g., LPS - 1) eluting with chloroform: methanol:water:acetic acid (90:15:1:0.5) gives 112 mg. of product. This material is dissolved in 0.5% aqueous acetic acid (20 ml.), millipore filtered, and lyophillized to give 99 mg. of $N^2$-[N-[(1,1-dimethylethoxy)carbonyl]-L-phenylalanyl]-N-[(S)-1-[(R)-hydroxy (2-thiazolyl)methyl]-3-methylbutyl]-L-histidinamide, acetate salt m.p. 89°-115° ; $[\alpha]_D = -30.2°$ (c=0.5, methanol). TLC (silica gel; chloroform:methanol:water:acetic acid, 90:15:1:0.5) $R_f$=0.21.

Anal. calc'd. for $C_{29}H_{40}N_6O_5S \cdot 0.5 C_2H_4O_2 \cdot 1 H_2O$:

C, 56.94; H, 7.01; N, 13.28; S, 5.07

Found C, 57.00; H, 6.63; N, 13.28; S, 4.78.

EXAMPLE 11

N-[(S)-2-Cyclohexyl-1-[(R)-hydroxy(1H-imidazol-2-yl)methyl]ethyl]-$N^2$-[N-(pyrrolidinylcarbonyl)-L-phenylalanyl]-L-histidinamide, dihydrochloride (a) N-(1-Pyrrolidinylcarbonyl)-L-phenylalanine, methyl ester N-Methylmorpholine (11 ml., 1000 mmole) and phosgene (101 ml. of 12% solution in benzene, 80 mmole) are added rapidly (dropwise) to a solution of pyrrolidine (3.34 ml., 40 mmole) in methylene chloride (200 ml.) at −30°. under argon. The resulting mixture is stirred for one hour at −30°, then for one hour as the temperature warms to 25°, after which the mixture is concentrated in vacuo at 25°. The residue is dissolved in methylene chloride. N-Methylmorpholine (13.2 ml., 120 mmole) followed by -L-phenylalanine, methyl ester, hydrochloride (8.63 g., 40 mmole) are then added. The mixture is stirred overnight under argon at 25°, after which it is concentrated to dryness. The residue is dissolved in ethyl acetate, washed sequentially with water, 1N hydrochloric acid, and saturated aqueous sodium bicarbonate solution, dried ($MgSO_4$), and concentrated. The residue is chromatographed on silica gel (Merck, 300 g.) eluting with benzene:acetic acid (6:1). Fractions containing the product ($R_f$=0.4) are combined and concentrated. the residue (1,5 g.) is crystallized from ethyl acetate/hexane to give 1.19 g. of N-(1pyrrolidinylcarbonyl)-L-phenylalanine, methyl ester;

m.p. 93°-95° ; $[\alpha]_D = -19.4°$ (c=1, methanol).

(b) N-(1-Pyrrolidinylcarbonyl)-L-phenylalanine

A mixture of the methyl ester product from part (a) (1.187 g., 4.3 mmole), aqueous 1N sodium hydroxide solution (5.15 ml., 5.15 mmole), and methanol (17 ml.) is stirred at 25° for 4 hours, after which it is concentrated in vacuo. 1N Hydrochloric acid and ethyl acetate are added to the residue, and the mixture is extracted with ethyl acetate. The extract is dried ($MgSO_4$) and concentrated to give N-(1-pyrrolidinylcarbonyl)-L-phenylalanine; $[\alpha]_D = 12.8°$ (c=1, methanol).

(c) ($\alpha$R, $\beta$S)-$\beta$-Amino-$\alpha$-[1-[(phenylmethoxy)methyl]-1H-imidazol-2-yl]cyclohexanepropanol A solution of [(1S)-1-(cyclohexylmethyl)-2-hydroxy-2-[1-[(phenylmethoxy)methyl]-1H-imidazol2-yl]ethyl]-carbamic acid, 1,1-dimethylethyl ester (slow moving isomer) (3.92, 8.83 mmole) [prepared as described in Example 6 (d) ]in ethyl acetate (200 ml.) is cooled to 0° and HCl gas is bubbled through the solution for 30 minutes. The mixture is then stirred for 3.5 hours as it warms to room temperature, after which it is concentrated in vacuo to give 3.56 g. of ($\alpha$R, $\beta$S)-$\beta$-amino-$\alpha$-[1-[(phenylmethoxy)methyl]-1H-imidazol-2-yl]cyclohexanepropanol as a white powder.

(d) [(1,1-Dimethylethoxy)carbonyl]-N-[(1S, 2R)-1-(cyclohexylmethyl)-2-hydroxy-2-[1-[(phenylmethoxy)-methyl]-(1H-imidazol-2-yl)]ethyl-$N^3$-[(phenylmethoxy)methyl]L-histidinamide Triethylamine (2.06 ml., 14.7 mmole) and dicyclohexylcarbodiimide (1.52 g., 7.35 mmole) are added to a solution of the product from part (c) (3.06 g., 7.35 mmole), 1-hydroxybenzotriazole hydrate (1.13 g., 7.35 mmole) and N-(1,1-dinethylethoxy)carbonyl]-1-[(phenylmethoxy)methyl]-L-histidine (2.76 g., 7.35 mmole) in tetrahydrofuran (20 ml.). The mixture is stirred for 18 hours at 25°, after which it is filtered. The filtrate is diluted with ethyl acetate, washed with saturated sodium bicarbonate solution, dried ($MgSO_4$), and concentrated. The residue (4.92 g. ) is chromatographed on silica gel (Merck) eluting with ethyl acetate:pyridine:acetic acid:water (80:20:6:11) to give as the major product 3.98 g. of [(1,1-dimethylethoxy)carbonyl]-N-[(1S, 2R)-1-(cyclohexymethyl)-2-hydroxy-2-[1-[(phenylmethoxy)methyl]-1H-imidazol-2-yl]ethyl]-$N^3$-[(phenylmethoxy)methyl]-L-histidanmide; $[\alpha]_D = -6.1°$ (c=1.8, methanol).

(e) N-[(1S,2R)-1-(Cyclohexylmethyl)-2-hydroxy-2-[1-(phenylmethoxy)methyl]-1H-imidazol-2-yl]ethyl]-$N^3$-[(phenylmethoxy)methyl]-L-histidinamide A solution of the product form part (d) (3.88 g., 5.53 mmole) in ethyl acetate (200 ml.) is cooled to 0°. in an ice bath and HCl gas is bubbled through the solution for 30 minutes. The resulting mixture is then stirred for 2.5 hours as it warms to 25°, after which it is concentrated to a small volume. The resulting white precipitate is collected to give 3.33 g. of N-[(1S,2R)-1-(cyclohexylmethyl)-2-[1-[(phenylmethoxy)methyl]-1H-imidazol-2-yl]ethyl]-$N^3$-[(phenylmethoxy)methyl]-L-histidinamide as a white powder;

m.p. 143°-157° ; $[\alpha]_D = +18.4°$ (c=1.0, methanol).

(f) N-[(S)-2-Cyclohexyl-1-[(R)-hydroxy-[1-[(phenylmethoxy)methyl]-1H-imidazol-2-yl]methyl]ethyl]-$N_2$-

[N-(pyrrolidinylcarbonyl)-L-phenylalanyl]-N³-[(phenylmethoxy)methyl]-L-histidinamide Triethylamine (0.84 ml., 6.0 mmole) followed by dicyclohexylcarbodiimide (453 mg., 2.2 mmole) are added to a mixture of N-(1pyrrolidinylcarbonyl)-L-phenylalanine (577 mg., 2.2 mmole), 1-hydroxybenzotriazole hydrate (337 mg., 2.2 mmole), and the L-histidinamide product from part (e) (1.47 g., 2.0 mmole) in tetrahydrofuran (8 ml.). The resulting mixture is stirred overnight as it warms to 25°. It is then filtered and the filtrate is diluted with ethyl acetate, washed with saturated sodium bicarbonate solution, dried (MgSO₄), and concentrated. The residue (1.7 g.) is chromatographed on silica gel eluting with ethyl acetate:pyridine:acetate acid:water (80:20:6:11) to give as the major product 1.46 g. of N-[(S)-2-cyclohexyl-1-[(R)-hydroxy-[1-[(phenylmethoxy)methyl]-1H-imidazol-2-yl]methyl]ethyl]-N²-[N-(pyrrolidinylcarbonyl)-L-phenylalanyl]-N³-[(phenylmethoxy)methyl]-L-histidinamide; $[\alpha]_D = -14.2°$ (c=0.8, methanol).

(g) N-[(S)-2-Cyclohexyl-1-[(R)-hydroxy-(1H-imidazol-2-yl)methyl]ethyl]-N²-[N-(pyrrolidinylcarbonyl)-L-phenylalanyl]-L-histidinamide, dihydrochloride A mixture of the product from part (f) (1.41 g., 1.60 mmole), 1N hydrochloric acid (3.36 ml., 3.36 mmole), and 20% palladium hydroxide on carbon catalyst (300 mg.) in methanol (25 ml.) is stirred under a stream of hydrogen for 24 hours. It is then filtered and concentrated. The residue is lyophillized from water to give 1.0 g. of N-[(S)-2-cyclohexyl-1-[(R)-hydroxy(1H-imidazol-2-yl)methyl]ethyl]-N²-[N-(pyrrolidinylcarbonyl)-L-phenylalanyl]-L-histidinamide, dihydrochloride as a fluffy white powder; m.p. (168) 175°–180°; $[\alpha]_D = -44.8°$ (c=0.9, methanol). TLC (silica gel; ethyl acetate:pyridine:acetic acid:water, 40:20:6:11) $R_f = 0.28$.

Anal. calc'd. for $C_{32}H_{44}N_8O_4 \cdot 2.2HCl \cdot 3.5 H_2O$:
C, 51.38; H, 7.17; N, 14.98; Cl, 10.43
Found: C, 51.18; H, 7.09; N, 14.98; Cl, 10.48.

EXAMPLE 12

N-[(S)-2-Cyclohexyl-1-[(R)-hydroxy(1H-imidazol-2-yl)methyl]ethyl]-N²-[N-[[(1,1-dimethylethyl)amino]carbonyl]-L-phenylalanyl]-L-histidinamide, dihydrochloride (a) N-[(4-Nitrophenoxy)carbonyl]-L-phenylalanine, methyl ester N-Methylmorpholine (2.2 ml., 20 mmole) followed by 4-nitrophenyl chloroformate (2.01 g., 10 mmole) are added to a suspension of L-phenylalanine, methyl ester, hydrochloride (2.15 g., 10 mmole) in methylene chloride (40 ml.) at −30°. The resulting mixture is stirred at −30° for 15 minutes, then for 15 minutes at 25°, after which it is washed sequentially with 1N HCl and saturated aqueous sodium bicarbonate solution, dried, and concentrated. The residue (2.96 g.) is crystallized from acetonitrile to give 1.22 g. of N-[(4-nitrophenoxy)carbonyl]-L-phenylalanine, methyl ester; m.p. 130°–131°; $[\alpha]_D = +88°$ (c=1.5, chloroform). The mother liquor is chromatographed on silica gel (90 g.) eluting with benzene:ethyl acetate (9:1) to give an additional 760 mg. of product.

(b) N-[[(1,1-Dimethylethyl)amino]carbonyl]-L-phenylalanine, methyl ester 1,1-Dimethylethyl amine (0.56 ml., 5.4 mmole) is added to a solution of the product from part (a) (1.48 g., 4.3 mmole) in toluene (21 ml.) at 0°. The resulting mixture is stirred for 24 hours as it warms to 25°, after which is is concentrated in vacuo. The residue is dissolved in ethyl acetate and the solution is washed sequentially with 1 N HCl solution, saturated aqueous sodium bicarbonate solution, and saturated potassium carbonate solution. The organic phase is filtered and the filtrate is washed with aqueous potassium carbonate solution until the washes are colorless. The organic extract is dried (MgSO₄) and concentrated in vacuo. The residue (1.17 g.) is crystallized from ethyl acetate/hexane to give 850 mg. of N-[[(1,1-dimethylethyl)amino]carbonyl]-L-phenylalanine, methyl ester; m.p. 84°–86°; $[\alpha]_D = -24.4°$ (c=0.9, methanol). p (c) N-[[(1,1-Dimethylethyl)amino]carbonyl]-L-phenylalanine A mixturee of the methyl ester product from part (b) (838 mg., 3.0 mmole) and aqueous 1N sodium hydroxide solution (3.3 ml., 3.3 mmole) in methanol (3 ml.) is stirred for 2 hours at 25°, after which it is concentrated in vacuo. The residue is dissolved in water and washed with ethyl acetate. The aqueous layer is made acidic by the addition of 1N HCl solution and extracted with ethyl acetate. The extract is dried (MgSO₄) and concentrated to give 603 mg. of N-[[(1,1-dimethylethyl)amino]carbonyl]-L-phenylalanine. $[\alpha]_D = -39.6°$ (c=0.7, methanol).

(d) N-[(S)-2-Cyclohexyl-1-[(R)-hydroxy[1[(phenylmethoxy)methyl]-1H-imidazol-2-yl]-methyl]ethyl]-N²-[N-[[(1,1-dimethylethyl)amino]carbonyl]-L-phenylalanyl]-N³-[(phenylmethoxy)methyl]-L-histidinamide Triethylamine (0.84 ml., 6.0 mmole) and dicyclohexylcarbodiimide (453 mg., 2.20 mmole) are added to mixture of N-[(1S, 2R)-1-(cyclohexylmethy)-2-hydroxy-2-[1-[(phenylmethoxy)methyl]-1H-imidazol-2-yl]ethyl]-N³-[(phenylmethoxy)methyl]-L-histidinamide (1.47 g., 2.0 mmole) [prepared as set forth in Example 11 (e)], the product from part (c) (582 mg., 2.20 mmole), and 1-hydroxybenzotriazole hydrate (337 mg., 2.20 mmole) in tetrahydrofuran (8 ml.) at 0°. The resulting mixture is stirred overnight as it warms to 25°, after which it is filtered. The filtrate is diluted with ethyl acetate, washed with saturated sodium bicarbinate solution and brine, dried (MgSO₄), and concentrated. The residue is flash chromatographed on silica gel (Merck) eluting with ethyl acetate:pyridine:acetic ecid:water (80:20:6:11) to give as the major product 1.48 g. of N-[(-S)-2-cyclohexyl-1-[(R)-hydroxy[1-[(phenylmethoxy)-methyl]-1H-imidazol-2-yl]methyl]ethyl]-N²-[N-[[(1,1-dimethylethyl)amino]-carbonyl]-L-phenylalanyl]-N³-[(phenylmethoxy)methyl]-L-histidinamide. $[\alpha]_D = -3.5°$ (c=9, methanol).

(e) N-[(S)-2-Cyclohexyl-1-[(R)-hydroxy(1H-imidazol-2-yl)methyl]ethyl]-N²-[N-[[(1,1-dimethylethyl)amino]-carbonyl]-L-phenylalanyl]-L-histidinamide, dihydrochloride A mixture of the product from part (d) (1.43 g., 1.69 mmole) and 20% palladium hydroxide on carbon catalyst (300 mg.) in methanol (25 ml.) is stirred under a stream of hydrogen for 24 hours, after which it is filtered and concentrated. The residue is lyophilized from water to give 1.064 g. of N-[(S)-2-cyclohexyl-1-[(R)-hydroxy(1H-imidazol-2-yl)methyl]ethyl]-N²-[N-[[(1,1-dimethylethyl)amino]-carbonyl]-L-phenylalanyl]-L-histidinamide, dihydrochloride as a white solid; m.p. (175) 178°–185°; $[\alpha]_D = -27.7°$ (c=0.9, methanol). TLC (silica gel; ethyl acetate:pyridine:acetic acid:water, 40:20:6:11) $R_f = 0.27$.

Anal. calc'd. for $C_{32}H_{46}N_8O_4 \cdot 2.5H_2O$: C, 52.77; H, 7.35; N, 15.38; Cl, 10.22

Found: C, 52.56; H, 7.36; N, 15.24; Cl, 10.37.

EXAMPLE 13

N-[(S)-2-Cyclohexyl-1-[(R)-hydroxy(1H-imidazol-2-yl)methyl]ethyl]-N$^2$-[N-(cyclopentylcarbonyl)-L-phenylalanyl]-L-histidinamide, dihydrochloride (a) N$^2$-(L-Phenylalanyl)-N-[(1S,2R)-2-cyclohexyl-1-[hydroxy[1-[(phenylmethoxy)methyl]-1H-imidazol-2-yl]-methyl]ethyl]-N$^3$-[(phenylmethoxy)methyl]-L-histidinamide, trihydrochloride salt A solution of N$^2$-[N-[(1,1-dimethylethoxy)-carbonyl]-L-phenylalanyl]-N-[(S)-1-[(R)-hydroxy-[1-(phenylmethoxy)methyl]-1H-imidazol-2-yl]-methyl]-2-cyclohexylethyl]-3'-[(phenylmethoxy)-methyl]-L-histidinamide (7.63 g., 9.0 mmole) [prepared as set forth in Example 7(a)] in ethyl acetate (325 ml.) is cooled in an ice-water bath under argon and then saturated with HCl gas. The mixture is stoppered and stirred cold for 30 minutes, then the bath is removed and the mixture is allowed to warm to 25° over 60 minutes. Removal of the solvents in vacuo followed by drying of the colorless solid product in vacuo gives 7.64 g. of crude N$^2$-(L-phenylalanyl)-N-[(1S,2R)-2-cyclohexyl-1-[hydroxy[1-[(phenylmethoxy)-methyl]-1H-imidazol-2-yl]methyl]ethyl]-N$^3$-[(phenyl-methoxy)methyl]-L-histidinamide as a trihydrochloride salt.

(b) N-[(S)-2-Cyclohexyl-1-[(R)-hydroxy[1-[(phenylmethoxy)methyl]-1H-imidazol-2-yl]methyl]ethyl]-N$^2$-[N-(cyclopentylcarbonyl)-L-phenylalanyl]-N$^3$-[(phenylmethoxy)methyl]-L-histidinamide Triethylamine (0.63 ml., 4.5 mmole) and dicyclohexylcarbodiimide (340 mg., 1.65 mmole) are added to a solution of the trihydrochloride salt product from part (a) (1.34 g., 1.5 mmole), 1-hydroxybenzotriazole hydrate (252 mg., 1.65 mmole), and cyclopentanecarboxylic acid (0.18 ml., 1.65 mmole). The resulting mixture is stirred for 18 hours at 25° after which it is filtered. The filtrate is diluted with ethyl acetate, washed with saturated sodium bicarbonate solution, dried (MgSO$_4$), and concentrated. The residue (1.25 g.) is chromatographed on silica gel (Merck) eluting with ethyl acetate:pyridine:acetic acid:water (80:20:6:11) to give as the major product 800 mg. of N-[(S)-2-cyclohexyl-1-[(R)-hydroxy[1-[(phenylmethoxy)methyl]-1H-imidazol-2-yl]methyl]ethyl]-N$^2$-[N-(cyclopentylcarbonyl)-L-phenylalanyl]-N$^3$-[(phenylmethoxy)methyl]-L-histidinamide $[\alpha]_D = -8.1°$ (c=1.04, methanol).

(c) N-[(S)-2-Cyclohexyl-1-[(R)-hydroxy(1H-imidazol-2-yl)methyl]ethyl]-N$^2$-[N-(cyclopentylcarbonyl)-L-phenylalanyl]-L-histidinamide, dihydrochloride A mixture of the product from part (b) (740 mg., 0.87 mmole), 20% palladium hydroxide on carbon catalyst (150 mg.), and 1.0 N hydrochloric acid (1.83 ml., 1.83 mmole) in methanol (30 ml.) is hydrogenated under a slow stream of hydrogen for 18 hours. The mixture is then filtered and concentrated to dryness. The residue is dissolved in water and lyophilized to give N-[(S)-2-cyclohexyl-1-[(R)-hydroxy(1H-imidazol-2-yl)methyl]ethyl]-N$^2$-[N-(cyclopentylcarbonyl)-L-phenylalanyl]-L-histidinamide, dihydrochloride; m.p. (155) 174°-177°. $[\alpha]_D = -28.2°$ (C=0.97, methanol). TLC (silica gel; ethyl acetate:pyridine:acetic acid:water, 40:20:6:11) R$_f$=0.25.

Anal. calc'd. for $C_{33}H_{45}N_7O_4 \cdot 2.15\ HCl \cdot 3.36\ H_2O$: C, 53.37; H, 7.31; N, 13.20; Cl, 10.26

Found: C, 53.37; H, 7.30; N, 13.31; Cl, 10.31.

EXAMPLE 14

N-[(S)-2-Cyclohexyl-1-[(R)-hydroxy(1H-imidazol-2-yl)methyl]ethyl]-N$^2$-[N-(3,3-dimethyl-1-oxobutyl)-L-phenylalanyl]-L-histidinamide, dihydrochloride (a) N-[(S)-2-Cyclohexyl-1-[(R)-hydroxy[1-[(phenylmethoxy)methyl]-1H-imidazol-2-yl]methyl]ethyl]-N$^2$-[(phenylmethoxy)methyl]-L-histidinamide Triethylamine (0.63 ml., 4.5 mmole) followed by dicyclohexylcarbodiimide (340 mg., 1.65 mmole) are added to a solution of N$^2$-(L-phenylalanyl)-N-[(1S,2R)-2-cyclohexyl-1-[hydroxy[1-[(phenylmethoxy)methyl]-1H-imidazol-2-yl]methyl]ethyl]-N$^3$-[(phenylmethoxy)-methyl]-L-histidinamide, hydrochloride salt (1.34 g., 1.5 mmole) [prepared as described in Example 13(e)], 1-hydroxybenzotriazole hydrate (252 mg., 1.65 mmole) and 3,3-dimethylbutanoic acid (0.21 ml., 1.65 mmole) in tetrahydrofuran (5 ml.) at 0°. The resulting mixture is stirred for 18 hours as it warms to 25°, after which it is filtered. The filtrate is diluted with ethyl acetate, washed with saturated aqueous sodium bicarbonate solution, dried (MgSO$_4$), and concentrated. The residue (1.23 g.) is purified by flash chromatography on silica gel (Merck, 150 g.) eluting with ethyl acetate:pyridine:acetic acid: water (80:20:6:11) to give as the major product 730 mg. of N-[(S)-2-cyclohexyl-1-[(R)-hydroxy[1-[(phenylmethoxy)methyl]-1H-imidazol-2-yl]methyl]-ethyl]-N$^2$-[N-(3,3-dimethyl-1-oxobutyl)-L-phenylalanyl]-N$^3$-[(phenylmethoxy)methyl]-L-histidinamide; $[\alpha]_D = -11.5°$ (c=1, methanol).

(b) N-[(S)-2-Cyclohexyl-1-[(R)-hydroxy(1H-imidazol-2-yl)methyl]ethyl]-N$^2$-[N-(3,3-dimethyl-1-oxobutyl)-L-phenylalanyl]-L-histidinamide, dihydrochloride A mixture of the product from part (a) (660 mg., 0.8 mmole), 20% palladium hydroxide on carbon catalyst (150 mg.) and 1.0 N hydrochloric acid (1.7 ml., 1.7 mmole) in methanol (20 ml.) is hydrogenated under a slow stream of hydrogen for 24 hours. The mixture is then filtered and concentrated to dryness. The residue (540 mg.) is dissolved in water and activated charcoal (50 mg.) is added. the resulting mixture is filtered and lyophillized to give N-[(S)-2-cyclohexyl-1-[(R)-hydroxy(1H-imidazol-2-yl)methyl]ethyl]-N$^2$-[N-(3,3-dimethyl-1-oxobutyl)-L-phenylalanyl]-L-histidinamide, dihydrochloride;

m.p. 158°-184°; $[\alpha]_D = -32.4°$ (c=0.79, methanol). TLC (silica gel; ethyl acetate:pyridine:acetic acid:water, 40:20:6:11) R$_f$=0.27.

Anal. calc'd. for $C_{33}H_{47}N_7O_4 \cdot 2.15\ HCl \cdot 2.5\ H_2O$: C, 54.35; H, 7.49; N, 13.45; Cl, 10.45

Found: C, 54.16; H, 7.45; N, 13.59; Cl, 10.42.

EXAMPLE 15

(1S,2R)-N-[1-(Cyclohexylmethyl)-2-hydroxy-2-(1H-imidazol-2-yl)ethyl]-N$^2$-[N-(4-morpholinylcarbonyl)-L-phenylalanyl]-L-histidinamide, trifluoroacetate salt (a) N-(4-Morpholinylcarbonyl)-L-phenylalanine, methyl ester Morpholine (1.1 ml., 12.5 ml.) is added to a solution of N-[(4-nitrophenoxy)carbonyl]-L-phenylalanine, methyl ester (3.44 g., 10 mmole). The resulting mixture is stirred for 2 hours at 25°, then at 100° for 5 hours, after which it is concentrated in vacuo. The residue is dissolved in ethyl acetate and the solution is washed with saturated potassium carbonate solution until the washes are colorless. The organic extract is dried (MgSO$_4$) and concentrated in vacuo. The residue is crystallized from ethyl acetate/hexane to give 2.3 g. of N-(4-morpholinylcarbonyl)-L-phenylalanine, methyl ester;
m.p. 88°–91°; [α]$_D$ = –30.8° (c=0.6, methanol).

(b) N-(4-Morpholinylcarbonyl)-L-phenylalanine

A mixture of the methyl ester product from part (a) (2.3 g., 7.8 mmole) and aqueous 1N sodium hydroxide solution (8.6 ml., 8.6 mmole) in methanol (12 ml.) is stirred for 5 hours at 25°, after which it is concentrated in vacuo. The residue is dissolved in water and washed with ethyl acetate. The extract is dried (MgSO$_4$) and concentrated to give 2.2 g. of N-(4-morpholinylcarbonyl)-L-phenylalanine; [α]$_D$ = –23.8° (c=2, methanol).

(c) (1S,2R)-N-[1-(Cyclohexylmethyl)-2-hydroxy-2-[1-[(phenylmethoxy)methyl]-(1H-imidazol-2-yl)ethyl]-N$^2$-[N-(4-morpholinylcarbonyl)-L-phenylalanyl]-N$^3$-[(phenylmethoxy)methyl]-L-histidinamide Triethylamine (0.84 ml., 6.0 mmole) and dicyclohexylcarbodiimide (435 mg., 2.20 mmole) are added to a mixture of N-[(1S,2R)-1-(cyclohexymethyl)-2-hydroxy-2-[1-[(phenylmethoxy)-methyl]-1H-imidazol-2-yl]ethyl]-N$^3$-[(phenylmethoxy)methyl]-L-histidinamide (1.49 g., 2.0 mmole) [prepared as set forth in Example 11(e)], the product from part (b) (612 mg., 2.20 mmole), and 1-hydroxybenzotriazole hydrate (337 mg., 2.20 mmole) in tetrahydrofuran (8 ml.) at 0°. The resulting mixture is stirred for 18 hours as it warms to 25°, after which it is filtered. The filtrate is diluted with ethyl acetate, washed with saturated sodium bicarbonate solution and brine, dried (MgSO$_4$), and concentrated. The residue is flash chromatographed on silica gel (Merck) eluting with ethyl acetate:pyridine:acetic acid:water (100:20:6:11) to give as the major product 1.42 g. of (1S,2R)-N-[1-(cyclohexylmethyl)-2-hydroxy-2-[1-[(phenylmethoxy)methyl]-(1H-imidazol-2-yl)ethyl]-N$^2$-[N-(4-morpholinylcarbonyl)-L-phenylalanyl]-N$^3$-[(phenylmethoxy)methyl]-L-histidinamide; [α]$_D$ = –15.3° (c=0.9, methanol).

(d) (1S,2R)-N-[1-(Cyclohexylmethyl)-2-hydroxy-2-(1H-imidazol-2-yl)ethyl]-N$^2$-[N-(4-morpholinylcarbonyl)-L-phenylalanyl]-L-histidinamide, trifluoroacetate salt A mixture of the product from part (c) (1.4 g., 1.6 mmole), 1.0 N hydrochloric acid (3.55 ml., 3.55 mmole), and 20% palladium hydroxide on carbon catalyst (300 mg.) in methanol (25 ml.) is stirred under a stream of hydrogen for 18 hours, after which it is filtered and concentrated. The residue (1.7 g.) is purified by preparative HPLC (YMC S15 ODS column 20×500 mm., 25 ml/min of 56% aqueous methanol containing 1% trifluoroacetic acid, UV absorbance monitored at 215 nm.). Fractions containing the major product (retention time 22 minutes) are combined and concentrated. The residue is lyophilized from water to give 850 mg. of (1S,2R)-N-[1-(cyclohexylmethyl)-2-hydroxy-2-(1H-imidazol-2-yl)ethyl]-N$^2$-[N-(4-morpholinylcarbonyl)-L-phenylalanyl]-L-histidinamide, trifluoroacetate salt as a white solid; m.p. (76) 89°–112°; [α]$_D$ = –38.1° (c=0.935, methanol). TLC (silica gel; ethyl acetate:pyridine:acetic acid:water, 40:20:6:11) R$_f$=0.19.

Anal. calc'd. for C$_{32}$H$_{44}$N$_8$O$_5$.2.2 C$_2$HF$_3$O$_2$.1.5 H$_2$O: C, 48.65; H, 5.52; N, 12.47; F, 13.95

Found: C, 48.69; H, 5.60; N, 12.49; F, 14.09.

EXAMPLE 16

(1S,2R)-N$^2$-[N-[(4-Methyl-1-piperazinyl)carbonyl]-L-phenylalanyl]-N-[1-(cyclohexylmethyl)-2-hydroxy-2-(1H-imidazol-2-yl)ethyl]-L-histidinamide, trihydrochloride (a) N-[(4-Methyl-1-piperazinyl)carbonyl]-L-phenylalanine, methyl ester A solution of N-[(4-nitrophenoxy)carbonyl]-L-phenylalanine, methyl ester (3.44 g., 10 mmole) in toluene (40 ml.) is heated to reflux and 1-methyl piperazine (1.4 ml., 12.5 mmole) is added to the warm solution. The mixture is stirred for 3 hours as it cools to 25°, after which it is concentrated in vacuo. The residue is dissolved in ethyl acetate and washed with aqueous potassium carbonate solution. The residue (3.85 g.) is crystalized from ethyl acetate to give 2.33 g. of N-[(4-methyl-1-piperazinyl)carbonyl]-L-phenylalanine, methyl ester as an off white solid; m.p. 137°–138°; [α]$_D$ = –35.9° (c=1, methanol).

(b) N-[(4-Methyl-1-piperazinyl)carbonyl]-L-phenylalanine

A solution of the methyl ester product from part (a) (2.29 g., 7.5 mmole) in methanol (12 ml.) and 1.0 N sodium hydroxide solution (8.25 ml., 8.25 mmole) is stirred for 3 hours at 25°, after which the methanol is removed in vacuo. The residue is acidified by the addition of excess 1.0 N HCl solution and is applied to a cationic exchange column (100 ml bed of AG 50 W-X2). The column is eluted with water until the eluant is no longer acidic and then is eluted with 2% aqueous pyridine. Product containing fractions are pooled and concentrated. The residue (1.0 g.) is crystallized by trituration with refluxing ethyl acetate to give 860 mg. of N-[(4-methyl-1-piperazinyl)carbonyl]-L-phenylalanine as a crystalline solid;
m.p. 130°–132°.

(c) (1S,2R)-N$^2$-[N-[(4-Methyl-1-piperazinyl)carbonyl]-L-phenylalanyl]-N-[1-(cyclohexylmethyl)-2-hydroxy-2-[1-[(phenylmethoxy)methyl]-1H-imidazol-2-yl]ethyl]-N$^3$-[(phenylmethoxy)methyl]-L-histidinamide Triethylamine (0.92 ml., 6.6 mmole) and dicyclohexylcarbodiimide (453 mg., 2.2 mmole) are added to a solution of N-[(1S,2R)-1-(cyclohexylmethyl)-2-hydroxy-2-[1-[(phenylmethoxy)methyl]-1H-imidazol-2-yl]ethyl]-N$^3$-[(phenylmethoxy)methyl]-L-histidinamide (1.5 g., 2.0 mmole) [prepared as described in Example 11(e)], 1-hydroxybenzotriazole hydrate (337 mg., 2.2 mmole), and the product from part (b) (690 mg., 2.2 mmole) in dimethylformamide (8 ml.) at 0°. The mixture is stirred for 18 hours at 25°, after which it is filtered. Ethyl acetate is added to the filtrate and the mixture is washed with saturated aqueous sodium bicarbonate solution and brine, dried (MgSO$_4$), and concentrated. The residue is flash chromatographed on silica gel (150 g., Merck) eluting with chloroform:methanol: ammonium hydroxide (100:12.5:0.25) to give as the major product 600 mg. of (1S,2R)-N$^2$-[N-[(4-methyl-1-pipera zinyl)carbonyl]-L-phenylalanyl]-N-[1-(cyclohexylmethyl)-2-hydroxy-2-[1-[(phenylmethoxy)methyl]-1H-imidazol-2-yl]ethyl]-N$^3$-[(phenylmethoxy)methyl]-L-histidinamide; [α]$_D$ = –21.5° (c=1, methanol).

(d) (1S,2R)-N$^2$-[N-[(4-Methyl-1-piperazinyl)carbonyl]-L-phenylalanyl]-N-[1-(cyclohexylmethyl)-2-hydroxy-2-(1H-imidazol-2-yl)ethyl]-L-histidinamide, trihydrochloride A mixture of the product from part (c) (563 mg., 0.64 mmole), 20% palladium hydroxide on carbon catalyst (125 mg.), 1.0N HCl solution (2.12 ml., 2.12 mmole) and methanol (20 ml.) is hydrogenated under a slow stream of hydrogen for 20 hours, after which it is filtered and concentrated. The residue is dissolved in water, charcoal filtered, and lyophillized to give 442 mg. of (1S,2R)-N²-[N-[(4-methyl-1-piperazinyl)carbonyl]-L-phenylalanyl]-N-[1-(cyclohexylmethyl)-2-hydroxy-2-(1H-imidazol-2-yl)ethyl]-L-histidinamide, trihydrochloride;

m.p. 178°-202°; $[\alpha]_D = -54.4°$ (c=0.97, methanol). TLC (silica gel; chloroform: methanol:ammonium hydroxide, 100:25:1) $R_f=0.39$.

Anal calc'd. for $C_{33}H_{47}N_9O_4 \cdot 3.3$ HCl·4.0 $H_2O$: C, 47.96; H, 7.11; N, 15.26; Cl, 14.16

Found: C, 47.96; H, 7.06; N, 15.32; Cl, 14.10.

EXAMPLE 17

(1S,2R)-N-[1-(Cyclohexylmethyl)-2-hydroxy-2-(2-thiazolyl)ethyl]-N²-[N-[(1,1-dimethylethoxy)carbonyl]-L-phenylalanyl]-L-histidinamide, 0.5 acetate salt (a) (S)-α-[[(1,1-Dimethylethoxy)carbonyl]amino]cyclohexanepropanoic acid Platinum oxide catalyst (5 g.) is added to a solution of N-[(1,1-dimethylethoxy)carbonyl]-L-phenylalanine (120 g., 0.452 mole) in absolute ethanol (1 l.). The mixture is placed on a Parr reduction apparatus at 50 lbs. pressure. The absorption of hydrogen is rapid and the hydrogen reservoir needs continued refilling. The reduction proceeds overnight and after 20 hours is completed. The mixture is filtered through Celite and concentrated in vacuo to give 124.4 g. of (S)-α-[[(1,1-dimethylethoxy)carbonyl]amino]cyclohexanepropanoic acid as a glassy solid colorless residue; $[\alpha]_D = -9.5°$ (c=1, methanol). TLC (silica gel; toluene:acetic acid, 4:1) $R_f=0.62$.

(b) (S)-α-[[(1,1-Dimethylethoxy)carbonyl]amino]-N-methoxy-N-methylcyclohexanepropanamide The product from part (a) (22.6 g., 83.3 mmole) is dissolved in tetrahydrofuran (250 ml.) under a blanket of argon at 26°. Carbonyldiimidazole solid (16.0 g., 98.7 mmole) is added in portions over one minute. Moderate gas evolution begins shortly after the addition is completed. The mixture remains colorless throughout. The mixture is stirred for 30 minutes at 25° during which time it remains clear and colorless. O,N-Dimethylhydroxylamine hydrochloride (11.5 g., 118 mmole) is then added in a single portion followed immediately by triethylamine (17.5 ml., 125 mmole) in a single portion. Following the triethylamine addition a white precipitate forms. The mixture is stirred for 3 hours at 25°, after which it is poured into 1N HCl (400 ml.) and extracted with ether (3×200 ml.). The colorless extracts are combined and washed with saturated sodium bicarbonate solution (2×200 ml.), dried (MgSO₄), and concentrated to give 24.2 g. of (S)-α-[[(1,1-dimethylethoxy)carbonyl]amino]-N-methoxy-N-methylcyclohexanepropanamide; $[\alpha]_D = -11.1°$ (c=7, methanol).

(c) (S)-[1-(Cyclohexylmethyl)-2-oxo-2-(2-thiazolyl)ethyl]carbamic acid, 1,1-dimethylethyl ester A 2.6 M solution of n-butyllithium (19.5 ml., 4.78 mmole) is added a solution of thiazole (4.07 g., 4.78 mmole) in tetrahydrofuran (80 ml.) at −60° under argon. The reaction is stirred at −60° for 30 minutes. The product from part (b) (7.5 g., 2.4 mmole) in tetrahydrofuran (15 ml.) is added dropwise at −60° and the reaction mixture is stirred until the temperature reaches −20° (about 40 minutes). The reaction is quenched with saturated ammonium chloride (40 ml.) and the product is extracted with ether (4×200 ml.). The organic layer is washed with brine, dried (MgSO₄), filtered and concentrated to yield 7.2 g. of crude product. This material is purified by filtration through a 60 g. pad of Merck silica using a hexane:ethyl acetate (8:2) solvent system. The filtrate is concentrated in vacuo to yield 6.0 g. of crystalline (S)-[1-(cyclohexylmethyl)-2-oxo-2-(2-thiazolyl)ethyl]carbamic acid, 1,1-dimethylethyl ester; m.p. 64°-69°. TLC (silica gel; hexane: ethyl acetate, 8:2) $R_f=0.45$.

Anal. calc'd. for $C_{17}H_{26}N_2SO_3 \cdot 0.1$ hexane C, 60.93; H, 7.90; N, 8.08; S, 9.24

Found: C, 61.17; H, 8.13; N, 7.95; S, 8.97.

(d) (1S,2R)-[1-(Cyclohexylmethyl)-2-hydroxy-2-(2-thiazolyl)ethyl]carbamic acid, 1,1-dimethylethyl ester The product from part (c) (2.73 g., 8.07 mmole) is dissolved in absolute ethanol (50 ml.) and cooled to 5°. Sodium borohydride (0.6 g., 16.14 mmole) is added portionwise and the reaction mixture is stirred for one hour, diluted with ether (200 ml.), and quenched with 1N HCl to pH 1. The organic layer is separated, washed twice with water and brine, dried (MgSO₄), and concentrated in vacuo. The two isomers are separated by flash chromatography on silica gel (Merck, 300 g.) eluting with ethyl acetate:hexane (3:8). The slower moving isomer is identified as the S,S configuration and the faster moving isomer is identified as (1S,2R)-[1-(cyclohexylmethyl)-2-hydroxy-2-(2-thiazolyl)ethyl]carbamic acid, 1,1-dimethylethyl ester; $[\alpha]_D = -30.72°$ (c=0.55, methanol). TLC (silica gel; ethyl acetate:hexane; 1:1) $R_f=0.70$.

(e) (αR,βS)-β-Amino-α-(2-thiazolyl)cyclohexanepropanol, dihydrochloride

The product from part (d) (0.8 g., 2.3 mmole) is dissolved in ethyl acetate (20 ml.) and HCl is bubbled into the solution for 10 minutes, after which it is stirred at room temperature for 4 hours. The reaction mixture is concentrated to give (αR,βS)-β-amino-α-(2-thiazolyl)cyclohexanepropanol, dihydrochloride as a white solid.

(f) N-[N-[(1,1-Dimethylethoxy)carbonyl]-L-phenylalanyl]-1'-(2,4-dinitrophenyl)-L-histidine 2,4-Dinitrofluorobenzene (4.62 ml., 36.74 mmole) is added to a solution of N-[N-[(1,1-dimethylethoxy)carbonyl]-L-phenylalanyl]-L-histidine (12.4 g., 30.8 mmole) in aqueous sodium bicarbonate (1M,82 ml.) and methanol (103 ml.). After stirring the solution for 2.5 hours, an additional amount of 2,4-dinitrofluorobenzene (0.6 ml., 4.77 mmole) is added. At the end of a total of 4 hours of reaction time, the mixture is acidified with aqueous hydrochloric acid (1N, 51.3 ml.) to a pH of 3.9 and then diluted with water (500 ml.). The separated solid is filtered and washed with water. This solid (16.6 g.) is then crystallized from hot ethyl acetate. Dicyclohexylamine (1.9 ml.) is added and the crystallized salt is filtered and the free acid is regenerated by acidification to give 1.008 g. of N-[N-[(1,1-dimethylethoxy)carbonyl]-L-phenylalanyl]-1'-(2,4-dinitrophenyl)-L-histidine;

m.p. 180°-182°; $[\alpha]_D = +5.2$ (c=1.4, acetic acid).

(g) (1S,2R)-N-[1-(Cyclohexylmethyl)-2-hydroxy2-(2-thiazolyl)ethyl]-N²-[N-[(1,1-dimethylethoxy)carbonyl]-L-phenylalanyl]-1'-(2,4-dinitrophenyl)-L-histidinamide N-Methylmorpholine (0.23 ml., 2.1 mmole) is added to a solution of the crude dihydrochloride salt product from part (e) (0.53 g., 1.5 mmole), N-[N-[(1,1-dimethylethoxy)carbonyl]-L-phenylalanyl]-1'-(2,4-dinitrophenyl)-L-histidine (0.85 g., 1.5 mmole), and 1-hydroxybenzotriazole hydrate (0.2 g., 1.5 mmole) at 0° under argon. Dicyclohexylcarbodiimide (0.31 g., 1.5 mmole) is finally added and the reaction is kept at 0° overnight, diluted with ethyl acetate (300 ml.), and filtered. The filtrate is washed with water, saturated sodium bicarbonate solution, and brine, dried (MgSO$_4$), filtered and concentrated in vacuo to yield 1.4 g. of crude product. Chromatography on silica gel (Merck, 200 g.) eluting with methanol:chloroform (5:100) gives 0.8 g. of (1S,2R)-N-[1-(cyclohexylmethyl)-2-hydroxy-2-(2-thiazolyl)ethyl]-N$^2$-[N-[(1,1-dimethylethoxy)carbonyl]-L-phenylalanyl]-1'-(2,4-dinitrophenyl)-L-histidinamide; [α]$_D$= −15.69° (c=0.51, methanol). TLC (silica gel; methanol:chloroform, 5:85) R$_f$=0.25.

(h) (1S,2R)-N-]1-(Cyclohexylmethyl)-2-hydroxy-2-(2-thiazolyl)ethyl]-N$^2$-[N-[(1,1-dimethylethoxy)carbonyl]-L-phenylalanyl]-L-histidinamide, 0.5 acetate salt The product from part (g) (0.8 g., 1.0 mmole) is treated with thioacetic acid (2.8 ml.) in dimethylformamide (4 ml.) at room temperature. After 2 hours, the reaction mixture is concentrated in vacuo, diluted with ethyl acetate (200 ml.) and ether (100 ml.), washed with saturated sodium bicarbonate solution (twice) and brine (twice), dried (MgSO$_4$), and concentrated in vacuo to give 0.8 g. of crude product. This material is chromatographed on silica gel (Merck, 200 g.) eluting with methanol:chloroform (5:100) to remove the (S,S) isomer contaminant. The solvent system is changed to chloroform:methanol:water:acetic acid (90:10:1:0.5) to elute the desired (S,R) isomer. The solution is concentrated in vacuo, dissolved in 2% aqueous acetic acid, filtered (millipore), and lyophillized to give 0.15 g. of (1S,2R)-N-[1-cyclohexylmethyl)-2-hydroxy-2-(2-thiazolyl)ethyl]-N$^2$-[N-[(1,1-dimethylethoxy)carbonyl]-L-phenylalanyl]-L-histidinamide, 0.5 acetate salt as a light yellow powder;

m.p. 110°-115°; [α]$_D$= −32.75 (c=0.4, methanol). TLC (silica gel; methanol:chloroform, 1:9) R$_f$=0.29.

Anal. calc'd. for C$_{32}$H$_{44}$N$_6$O$_5$S.0.5 C$_2$H$_4$O$_2$.H$_2$O: C, 58.90; H, 7.19; N, 12.49; S, 4.76
Found: C, 58.69; H, 6.94; N, 12.38; S, 4.92.

EXAMPLE 18

N-[(S)-1-[Hydroxy(1H-imidazol-4-yl)methyl]-3-methylbutyl]-N$^2$-[N-[(1,1-dimethylethoxy)carbonyl]-L-phenylalanyl]-L-histidinamide, 0.3 acetate salt (a) 1-[(Phenylmethoxy)methyl]-2-(phenylthio)-1H-imidazole A solution of n-butyllithium (3.8 ml., 2.6 N in hexane) is added dropwise to a solution of 1-[(phenylmethoxy)methyl]-1H-imidazole (1.88 g., 10 mmole) in tetrahydrofuran (35 ml.) at −60° under argon. After stirring for 2 hours, this solution is added dropwise to a solution of diphenyldisulfide (1.88 g., 10 mmole) at −60° and stirred at −50° to −60° for 2 hours. Saturated ammonium chloride (20 ml.) is added dropwise at room temperature and the crude product is extracted with ether (2×200 ml.), washed with brine, dried (MgSO$_4$) and concentrated in vacuo. Flash chromatography on silica gel (120 g., LPS-1) eluting with hexane: ethyl acetate (7:3) yields 2.2 g. of 1-[(phenylmethoxy)methyl]-2-phenylthio-1H-imidazole. TLC (silica gel; hexane:ethyl acetate, 7:3) R$_f$=0.21.

(b) [(1,1-Dimethylethoxy)carbonyl]-N-methoxy-N-methyl-L-leucinamide

N-[(1,1-Dimethylethoxy)carbonyl]-L-leucine hydrate (10 g., 40 mmole) is dissolved in excess toluene and concentrated to dryness. The residue is dissolved in tetrahydrofuran (100 ml.) and carbonyldiimidazole (7.8 g., 48 mmole) is added in a single portion. The mixture is stirred at room temperature for 30 minutes. O,N-Dimethylhydroxylamine hydrochloride (4.3 g., 44 mmole) and triethylamine (6.2 ml., 44 mmole) are then added. The resulting mixture is stirred at room temperature for 3 hours, after which it is poured into excess 1N hydrochloric acid. The mixture is extracted three times with ethyl acetate and the extracts are washed once with 1N hydrochloric acid and twice with saturated sodium bicarbonate solution, dried (MgSO$_4$), and concentrated to give 9.3 g. of [(1,1-dimethylethoxy)carbonyl]-N-methoxy-N-methyl-L-leucinamide as a colorless oil; [α]$_D$= −25.2° (c=1.6, methanol).

(c) (S)-[3-Methyl-1-[[3-[(phenylmethoxy)methyl]-2-(phenylthio)-3H-imidazol-4-yl]carbonyl]butyl]carbamic acid, 1,1-dimethylethyl ester Lithium diisopropylamide is prepared in situ by the dropwise addition of n-butyllithium (3.2 ml., 2.6 N in hexane) to a solution of diisopropylamine (1.2 ml., 8.4 mmole) in tetrahydrofuran (24 ml.) under argon at −60° for 15 minutes. The product from part (a) (2.36 g., 8 mmole) in tetrahydrofuran (20 ml.) is added dropwise at −50° and stirred at −78° for 10 minutes. The product from part (b) (1.08 g., 3.9 mmole) is added in tetrahydrofuran (6 ml.) at −60° and stirred until the reaction reaches 0° (40 minutes). The reaction is then quenched by the addition of saturated ammonium chloride (10 ml.) and diluted with ether (400 ml.). The organic layer is separated, washed with saturated ammonium chloride and brine, dried (MgSO$_4$), filtered, and concentrated in vacuo. The crude product is purified by flash chromatography on silica gel (480 g., LPS-1) eluting with hexane:ethyl acetate (8:2) to yield 1.03 g. of (S)-[3-methyl-1-[[3-[(phenylmethoxy)methyl]-2-(phenylthio)-3H-imidazol-4-yl]carbonyl]butyl]carbamic acid, 1,1-dimethylethyl ester as a yellow solid; m.p. 86°-89°. TLC (silica gel; hexane:ethyl acetate, 1:1) R$_f$=0.73.

Anal. calc'd. for C$_{28}$H$_{35}$N$_3$O$_4$S: C, 65.99; H, 6.92; N, 8.24; S, 6.29
Found: C, 66.19; H, 7.13; N, 8.30; S, 6.45.

(d) (S)-[3-Methyl-1-[[3-[(phenylmethoxy)methyl]-3H-imidazol-4-yl]carbonyl]butyl]carbamic acid, 1,1-dimethylethyl ester The product from part (c) (0.61 g., 1.02 mmole) is dissolved in methanol (10 ml.) and hydrogenated at atmospheric pressure overnight using 20% palladium hydroxide on carbon (0.5 g.) as catalyst. The reaction mixture is filtered (Celite), recharged with 0.5 g. of catalyst, and hydrogenated an additional 12 hours. It is then filtered (Celite) and chromatographed on silica gel (60 g., LPS-1) eluting with ethyl acetate: hexane (2:3). The product containing fractions are concentrated in vacuo to give 0.38 g. of (S)-[3-methyl-1-[[3-[(phenylmethoxy)methyl]-3H-imidazol-4-yl]carbonyl]butyl]carbamic acid, 1,1-dimethylethyl ester. TLC (silica gel; ethyl acetate:hexane, 1:1) R$_f$=0.45.

(e) (S)-[3-Methyl-1-[[3-[(phenylmethoxy)methyl]-3H-imidazol-4-yl]hydroxymethyl]butyl]carbamic acid, 1,1-dimethylethyl ester A 1M solution of lithium triethylborohydride (1.6 ml., 1.6 mmole) in tetrahydrofuran is added dropwise, at 0° under argon, to a solution of the product from part (d) (0.16 g., 0.4 mmole) in tetrahydrofuran (4 ml.). After 30 minutes, 0.5M hydrochloric acid (2 ml.) is added dropwise at 0°, the mixture is diluted with ether (200 ml.) and then washed with water and brine, dried (MgSO$_4$), filtered, and concentrated in vacuo to give 0.21 g. of crude product. This material is stirred overnight in 50 ml. of methanol:chloroform (1:1) with 3 g. of Merck silica, filtered, and concentrated in vacuo. The crude product is chromatographed through silica gel (LPS-1, 100 g.) using a 5% methanol:chloroform solvent system. The product containing fractions are combined and evaporated to give 0.16 g. of (S)-[3-methyl-1-[[3-[(phenylmethoxy)methyl]-3H-imidazol-4-yl]hydroxymethyl]butyl]carbamic acid, 1,1-dimethylethyl ester as a viscous oil. TLC (silica gel; methanol:chloroform, 1:20) $R_f$=0.22.

Anal. calc'd. for $C_{22}H_{23}N_3O_4 \cdot H_2O$ C, 62.70; H, 8.04; N, 9.99

Found: C, 62.70; H, 8.49; N, 9.97.

(f) α-[(S)-1-Amino-3-methylbutyl]-3-[(phenylmethoxy)methyl]-3H-imidazole-4-methanol A solution of the product from part (e) (0.11 g., 0.26 mmole) in dichloromethane (2 ml.) and trifluoroacetic acid (2 ml.) is stirred at 10° for 30 minutes and at room temperature for 10 minutes. The reaction mixture is evaporated in vacuo and then concentrated from acetonitrile (three times) to give α-[(S)-1-amino-3-methylbutyl]-3-[(phenylmethoxy)methyl]-3H-imidazole-4-methanol which contains 2.5M of trifluoroacetic acid.

Anal. calc'd. for $C_{28}H_{35}N_3O_4S$: C, 44.90; H, 4.71; N, 7.14

Found: C, 44.50; H, 4.80; N, 7.04.

(g) N-[(S)-1-[Hydroxy[3-[(phenylmethoxy)methyl]-3H-imidazol-4-yl]methyl]-3-methylbutyl]-$N^2$-[N-[(1,1-dimethylethoxy)carbonyl]-L-phenylalanyl]-$N^3$-[(phenylmethoxy)methyl]-L-histidinamide Diisopropylethylamine (0.11 ml., 0.52 mmole) is added to 3 ml. tetrahydrofuran solution of the crude 2.5M trifluoroacetic acid salt product from part (f) (0.26 mmole), at 0° undr argon, followed by the addition of N-[N-[(1,1-dimethylethoxy)-carbonyl]-L-phenylalanyl]-1'-[(phenylmethoxy)methyl]-L-histidine (135.9 mg., 0.26 mmole), 1-hydroxybenzotriazole hydrate (135.2 mg., 0.26 mmole) and finally dicyclohexylcarbodiimide (53.7 mg., 0.26 mmole). After one hour, dimethylaminopyridine (15 mg., 0.12 mmole) is added. The reaction mixture is stirred overnight at room temperature, concentrated in vacuo, dissolved in ethyl acetate (150 ml.), and filtered. The filtrate is washed with half saturated sodium bicarbonate solution and brine, dried (MgSO$_4$), filtered, and concentrated in vacuo to give 0.17 g. of crude product. Two flash chromatographies, one on silica gel (Merck, 80 g.) and the other on silica gel (LPS-1, 80 g.) employing the solvent system chloroform:methanol:ammonia hydroxide (100:10:0.2) yields 60 mg. of N-[(S)-1-[hydroxy[3-[(phenylmethoxy)methyl]-3H-imidazol-4-yl]methyl]-3-methylbutyl]-$N^2$-[N-[(1,1-dimethylethoxy)carbonyl]-L-phenylalanyl]-$N^3$-[(phenylmethoxy)methyl]-L-histidinamide (3:7 isomer ratio).

(h) N-[(S)-1-[Hydroxy(1H-imidazol-4-yl)methyl]-3-methylbutyl]-$N^2$-[N-[(1,1-dimethylethoxy)carbonyl]-L-phenylalanyl]-L-histidinamide, 0.3 acetate salt The product from part (g) (60 mg., 0.74 mmole) is dissolved in methanol (4 ml.), water (0.5 ml.), and 1N hydrochloric acid (0.15 ml.) and hydrogenated overnight using 20% palladium hydroxide on carbon catalyst (40 mg.). The reaction mixture is filtered through Celite, concentrated in vacuo, and chromatographed on silica (Merck, 30 g.) eluting with chloroform: methanol:water:acetic acid (90:20:2.5:1). The product containing fractions are combined and evaporated to yield 27.5 mg. of product. A portion of this sample is dissolved in ethyl acetate and stirred with water. The organic phase is concentrated to yield 12.1 mg. of N-[(S)-1-[hydroxy-(1H-imidazol-4-yl)methyl]-3-methylbutyl]-$N^2$-[N-[(1,1-dimethylethoxy)carbonyl]-L-phenylalanyl]-L-histidinamide, 0.3 acetate salt having an isomer ratio of about 1:4;

m.p. 113°-128°. TLC (silica gel; chloroform: methanol:water:acetic acid, 90:20:2.5:1) $R_f$=0.19.

Anal. calc'd. for $C_{29}H_{41}N_7O_5 \cdot 0.3\ C_2H_4O_2$: C, 60.70; H, 7.26; N, 16.74

Found: C, 60.80; H, 7.67; N, 16.68.

EXAMPLE 19

(1S,2R)-$N^2$-[N-[$N^2$-(Cyclobutylcarbonyl)-L-lysyl]-L-phenylalanyl]-N-[1-(cyclohexylmethyl)-2-hydroxy-2-(1H-imidazol-2-yl)ethyl]-L-histidinamide, 3,3-hydrochloride (a) (1S,2R)-$N^2$-[N-[$N^2$-(Cyclobutylcarbonyl)-$N^6$-[(p henylmethoxy)carbonyl]-L-lysyl]-L-phenylalanyl]-N-[1-(cyclohexylmethyl)-2-hydroxy-2-[1-[(phenylmethoxy)methyl]-1H-imidazol-2-yl]ethyl]-$N^3$-[(phenylmethoxy)methyl]-L-histidinamide N-Methylmorpholine (586 mg., 5.79 mmole) and dicyclohexylcarbodiimide (398 mg., 1.93 mmole) are added to a mixture of N-[(cyclobutyl)carbonyl]-$N^6$-[(phenylmethoxy)carbonyl]-L-lysine (700 mg., 1.93 mmole), $N^2$-(L-phenylalanyl)-N-[(1S,2R)-2-cyclohexyl-1-[hydroxy[1-[(phenylmethoxy)methyl]-1H-imidazol-2-yl]methyl]ethyl]-$N^3$-[(phenylmethoxy)methyl]-L-histidinamide, trihydrochloride salt (1.72 g., 1.93 mmole) [prepared as described in Example 13(a)], and 1-hydroxybenzotriazole hydrate (325 mg., 2.12 mmole) in tetrahydrofuran (20 ml.) at 0° under argon. The reaction is kept stoppered in a refrigerator for 3 days, then filtered, diluted with ethyl acetate, rinsed with three 15 ml. portions of water, 15 ml. of saturated sodium bicarbonate solution, and brine, dried (MgSO$_4$) and concentrated in vacuo to yield 2.12 g. of crude product. Recrystallization from methanol/ethyl acetate gives 1.2 g. of (1S,2R)-$N^2$-[N-[$N^2$-(cyclobutylcarbonyl)-$N^6$-[(p henylmethoxy)carbonyl]-L-lysyl]-L-phenylalanyl]-N-[1-(cyclohexylmethyl)-2-hydroxy-2-[1-[(phenylmethoxy)methyl]-1H-imidazol-2-yl]ethyl]-$N^3$-[(phenylmethoxy)methyl]-L-histidinamide;

m.p. 146°-162° (dec.); $[\alpha]_D$= −14.5° (c=0.5, methanol).

(b) (1S,2R)-$N^2$-[N-[$N^2$-(Cyclobutylcarbonyl)-L-lysyl]-L-phenylalanyl]-N-[1-(cyclohexylmethyl)-2-hydroxy-2-(1H-imidazol-2-yl)ethyl]-L-histidinamide, 3,3-hydrochloride A solution containing the product from part (a) (1.05 g., 0.952 mmole), hydrazine hydrate (476 mg., 9.52 mmole), and 20% palladium hydroxide on carbon catalyst (300 mg.) in methanol (50 ml.) is stirred under hydrogen for 24 hours. The reaction mixture is then filtered, concentrated to remove the methanol, and redissolved in water (25 ml.) containing 1N aqueous hydrochloric acid (2.63 ml.). Lyophillization gives 756 mg. of (1S,2R)-$N^2$-[N-[$N^2$-(cyclobutylcarbonyl)-L-lysyl]-L-phenylalanyl]-N-[1-(cyclohexylmethyl)-2hydroxy-2-(1H-imidazol-2-yl)ethyl]-L-histidinamide, 3.3 hydrochloride; m.p. 174°-187°; $[\alpha]_D$= −30.0° (c=0.5, methanol). TLC (silica gel; n-butanol: pyridine:acetic acid:-water, 4:1:1:1) $R_f$=0.48.

Anal. calc'd. for $C_{38}H_{55}N_9O_5 \cdot 3.3$ HCl$\cdot 3.3$ H$_2$O: C, 50.84; H, 7.29; N, 14.04; Cl, 13.03

Found: C, 50.84; H, 7.43; N, 14,20; Cl, 12.96.

EXAMPLE 20

(1S,2R)-N-[1-(Cyclohexylmethyl)-2-hydroxy-2-(1H-imidazol-2-yl)ethyl]-$N^2$-[1-oxo-3-phenyl-2-(phenylmethyl)propyl]-L-histidinamide, 2,2-trifluoroacetate salt (a) 2,2-Bis(phenylmethyl)propanedioic acid, diethyl ester Diethyl benzylalonate (8.6 ml., 50 mmole) is added dropwise over 5 minutes to a suspension of sodium hydride (2.0 g., 50 mmole, of 60% dispersion in mineral oil) in tetrahydrofuran (100 ml.). Gas evolution is observed. When the addition is completed, the mixture is heated at reflux for 10 minutes and is then cooled to 25°. A solution of benzyl bromide (6.5 ml., 55 mmole) in tetrahydrofuran (10 ml.) is added dropwise over 10 minutes, after which the mixture is stirred for 20 hours at 25° under argon. 1N Hydrochloric acid (100 ml., 100 mmole) is then added and the mixture is extracted with ethyl acetate. The extract is washed with saturated aqueous sodium bicarbonate solution, dried ($MgSO_4$), and concentrated in vacuo. The residue (17.8 g.) is chromatographed on silica gel (Merck) eluting with hexane:ethyl acetate (5:1) to give 2,2-bis(phenylmethyl)propanedioic acid, diethyl ester.

(b) α-(Phenylmethyl)benzenepropanoic aci

A solution of the diethyl ester product from part (a) (14.4 g., 42.5 mmole) in ethanol (100 ml.) and 1.0 N aqueous sodium hydroxide solution (95 ml., 95 mmole) is heated at reflux for 48 hours. The ethanol is removed in vacuo and the remaining aqueous mixture is acidified by the addition of 1N hydrochloric acid. The mixture is saturated with sodium chloride and extracted with ethyl acetate. The extract is dried ($MgSO_4$) and concentrated in vacuo to give 9.6 g. of the dicarboxylic acid which crystallizes on standing.

A solution of the above material (9.6 g.) in dioxane (100 ml.) containing concentrated hydrochloric acid (1 ml.) is heated at reflux for 24 hours, after which it is concentrated to dryness. The residue is crystallized from ethyl acetate:hexane to give 7.02 g. of α-(phenylmethyl)benzenepropanoic acid;

m.p. 86°–87°.

(c) (1S,2R)-N-[1-(Cyclohexylmethyl)-2-hydroxy-2-[1-[(phenylmethoxy)methyl]-1H-imidazol-2yl]ethyl]-$N^2$-[1-oxo-3-phenyl-2-(phenylmethyl)propyl]-$N^3$-[1-(phenylmethoxy)methyl]-L-histidinamide Triethylamine (0.53 ml., 3.8 mmole) and dicyclohexylcarbodiimide (283 mg., 1.4 mmole) are added to a solution of N-[(1S,2R)-1-(cyclohexylmethyl)-2-hydroxy-2-[1-[(phenylmethoxy)methyl]-1H-imidazol-2-yl]ethyl]-$N^3$-[(phenylmethoxy)methyl]-L-histidinamide (920 mg., 1.25 mmole) [prepared as described in Example 11(e)], 1-hydroxybenzotriazole hydrate (210 mg., 1.34 mmole), and the product from part (b) (330 mg., 1.4 mmole) in tetrahydrofuran (5 ml.) at 0°. The resulting mixture is stirred for 18 hours at 25°, after which it is filtered. The filtrate is diluted with ethyl acetate, washed with saturated sodium bicarbonate solution and brine, dried, and concentrated. The residue is chromatographed on silica gel (Merck) eluting with ethyl acetate: pyridine:acetic acid:water (100:20:6:11) to give 900 mg. of (1S,2R)-N-[1-(cyclohexylmethyl)-2-hydroxy-2-[1-[(phenylmethoxy)methyl]-1H-imidazol-2-yl]ethyl]-$N^2$-[1-oxo-3-phenyl-2-(phenylmethyl)propyl]-$N^3$-[(phenylmethoxy)-methyl]-L-histidinamide as the major product; $[α]_D = -5.3°$ (c=1, methanol).

(d) (1S,2R)-N-[1-(Cyclohexylmethyl)-2-hydroxy-2-(1H-imidazol-2-yl)ethyl]-$N^2$-[1-oxo-3-phenyl-2-(phenylmethyl)propyl]-L-histidinamide,2.2 trifluoroacetate salt A mixture of the product from part (c) (900 mg., 1.1 mmole), 20% palladium hydroxide on carbon catalyst (200 mg.), and 1.0 N hydrochloric acid (2.4 ml., 2.4 mmole) in methanol (20 ml.) is hydrogenated under a slow stream of hydrogen for 19 hours. The mixture is then filtered and concentrated to dryness. The residue is dissolved in water, activated carbon is added, and the mixture is then millipore filtered and lyophillized to give 590 mg. of a pinkish solid. This solid is further purified by preparative HPLC (YMC S 15 ODS column, 20×500 mm., 67% aqueous methanol containing 1% trifluoroacetic acid, 25 ml/min., UV 220 nm. monitoring). Fractions containing the major component (retention time 32 minutes) are combined and concentrated. The residue is dissolved in water and lyophilized to give 465 mg. of (1S,2R)-N-[1-(cyclohexylmethyl)-2-hydroxy-2-(1H-imidazol-2-yl)ethyl]-$N^2$-[1-oxo-3-phenyl-2-(phenylmethyl)propyl]-L-histidinamide, 2.2 trifluoroacetate salt as a fluffy white solid; m.p. (70) 78°–108°; $[α]_D = -28.0°$ (c=0.70, methanol). TLC (silica gel, ethyl acetate:pyridine:acetic acid:water, 40:20:6:11) $R_f$=0.36.

Anal. calc'd. for $C_{34}H_{42}N_6O_3 \cdot 2.2\ C_2HF_3O_2 \cdot 0.8\ H_2O$: C, 54.39; H, 5.44; N, 9.91; F, 14.79
Found: C, 54.34; H, 5.55; N, 10.00; F, 14.73.

EXAMPLE 21

(1S,2R)-N-[1-(Cyclohexylmethyl)-2-hydroxy-2-(1H-imidazol-2-yl)ethyl]-$N^2$-[1-oxo-3-(1-naphthalenyl)-2-(1-naphthalenylmethyl)propyl]-L-histidinamide, dihydrochloride (a) 2,2-Bis(1-naphthalenylmethyl)propanedioic acid, diethyl ester Diethylmalonate (15.2 ml., 100 mmole) is added to a suspension of sodium hydride (200 mmole) in tetrahydrofuran (400 ml.). The addition is accompanied by gas evolution. When the addition is completed, the mixture is warmed to reflux temperature to yield a homogeneous solution. 1-Chloromethyl naphthalene (35.4 g., 200 mmole) is added to the refluxing solution over one hour. The mixture is then stirred at reflux for 17 hours, after which it is quenched by the addition of excess 1N hydrochloric acid. The mixture is extracted with ether and the extract is washed with saturated sodium bicarbonate solution, dried ($MgSO_4$), and concentrated to a yellow oil. The residue is dissolved in hot petroleum ether and the colorless solution is decanted from a brown insoluble gum. The solution is concentrated and the residue is crystallized twice from methanol to give 13 g. of 2,2-bis(1-naphthalenylmethyl)propanedioic acid, diethyl ester as colorless crystals; m. p. 79°–81°.

(b) α-(1-Naphthalenylmethyl)-1-naphthalenylpropanoic acid

A mixture of the diethyl ester from part (a) (11.0 g., 25 mmole) and 1.0 N sodium hydroxide solution (50 ml., 50 mmole) in ethanol (50 ml.) is stirred at 25° for 3 days. Sodium hydroxide solid (2 g.) is then added and the mixture is stirred for an additional 6 hours at 25°, after which it is concentrated in vacuo. The residue is diluted with water, resulting in a dense white precipitate. The precipitate is collected and washed with hexane. The filtrate is then washed with hexane and the combined hexane washes are extracted with sodium hydroxide solution. The sodium hydroxide extracts and the solid precipitates are combined and acidified by the addition of concentrated hydrochloric acid. The mixture is then extracted with ethyl acetate and the extract is dried and concentrated. The residue (7.2 g.) is dissolved in dioxane (250 ml.). Concentrated hydrochloric acid (1.0 ml.) is added and the mixture is stirred at 90° for 19 hours, after which it is concentrated in vacuo. The residue is triturated with methanol to give 4.6 g. of α-(1-naphthalenylmethyl)-1-naphthalenylpropanoic acid as a white powder; m.p. 168°–170°.

(c) N-[(1S,2R)-1-(Cyclohexylmethyl)-2-hydroxy-2-(1H-imidazol-2-yl)ethyl]-L-histidinamide A mixture of [(1,1-dimethylethoxy)carbonyl]-N-[(1S,2R)-1-(cyclohexylmethyl)-2-hydroxy-2-[1-[(phenylmethoxy)methyl]-1H-imidazol-2-yl]ethyl]-N³-[(phenylmethoxy)methyl]-L-histidinamide (1.46 g., 2.0 mmole) [prepared as set forth in Example 11 (d)], 20% palladium hydroxide on carbon catalyst (350 mg.), and 1.0 N hydrochloric acid (4 ml., 4 mmole) in methanol (15 ml.) is hydrogenated under a slow stream of hydrogen for 20 hours at 25°, after which it is filtered and concentrated to dryness. The residue (1.1 g.) is dissolved in acetic acid (30 ml.) and dry HCl gas is bubbled through the solution for 30 minutes at 25°. The mixture is then stirred at 25° for 2 hours, after which is is concentrated in vacuo. The residue is triturated with acetonitrile to give 833 mg. of a white solid. The solid is dissolved in excess 1N hydrochloric acid and concentrated to dryness. The process is repeated three times to give N-[(1S,2R)-1-(cyclohexylmethyl)-2-hydroxy-2-(1H-imidazol-2-yl)ethyl]-L-histidinamide as a white solid.

(d) (1S,2R)-N-[1-(Cyclohexylmethyl)-2-hydroxy-2-(1H-imidazol-2-yl)ethyl]-N²-[1-oxo-3-(1-naphthalenyl)-2-(1-naphthalenylmethyl)propyl]-L-histidinamide, dihydrochloride Triethylamine (0.68 ml., 4.9 mmole) and dicyclohexylcarbodiimide (309 mg., 1.5 mmole) are added to a mixture of the product from part (c) (750 mg., 1.5 mmole), 1-hydroxybenzotriazole hydrate (230 mg., 1.5 mmole) and the product from part (b) (511 mg., 1.5 mmole) in dimethylformamide (7 ml.) at 0°. The resulting mixture is stirred for 18 hours at 25° after which it is concentrated to dryness. Methanol (9 ml.) and 1.0 N hydrochloric acid (6 ml.) are added to the residue. The mixture is filtered and the filtrate is concentrated to dryness. The residue is flash chromatographed on silica gel (Merck) eluting with ethyl acetate:pyridine:acetic acid:water (50:20:6:11) to give a major product ($R_f=0.25$) that is homogeneous but dark brown in color. This material is dissolved in 1.0 N hydrochloric acid and reconcentrated. The resulting hydrochloride salt (430 mg.) is purified by chromatography on HP-20 eluting with a gradient from 0.01 N hydrochloric acid to methanol. Colorless fractions containing the major product are combined and partially concentrated to remove the methanol. The aqueous residue is lyophillized to give a fluffy electrostatic white solid that is dissolved in water and relyophillized to give 220 mg. of (1S,2R)-N-[1-(cyclohexylmethyl)-2hydroxy-2-(1H-imidazol-2-yl)ethyl]-N²-[1-oxo-3-(1-naphthalenyl)-2-(1-naphthalenylmethyl)propyl]-L-histidinamide, dihydrochloride; m.p. 163°–183°; $[\alpha]_D = -56.1°$ (c=0.59, methanol). TLC (silica gel; ethyl acetate:pyridine:acetic acid:water, 50:20:6:11) $R_f=0.25$.

Anal. calc'd. for $C_{42}H_{46}N_6O_3 \cdot 2.2$ HCl $\cdot 2.05$ $H_2O$: C, 63.06; H, 6.59; N, 10.51; Cl, 9.75

Found: C, 63.03; H, 6.76; N, 10.61; Cl, 9.78.

EXAMPLES 22–46

Following the procedures of Examples 1 to 21, additional compounds within the scope of this invention can be prepared having the forula

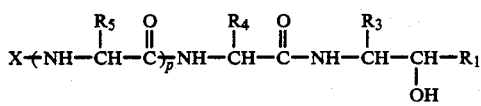

wherein the substituents are as defined below.

| Example | $X+NH-\overset{R_5}{\underset{|}{CH}}-\overset{O}{\underset{\|}{C}})_p$ | R₄ | R₃ | R₁ |
|---|---|---|---|---|
| 22 | (H₃C)₃-C-C(=O)-O-CH₂-NH-C(=O)-CH(CH₂-C₆H₅)- | -CH₂-(imidazole-NH) | -CH₂-C₆H₅ | N-methyl imidazole |
| 23 | C₆H₅-CH₂-O-C(=O)-NH-C(=O)-CH(CH₂-C₆H₅)- | -CH₂-(imidazole-NH) | -CH₂-cyclohexyl | imidazole (NH) with CH₃ |
| 24 | (naphthyl-CH(CH₂-))₂ C=O | -CH₂-(imidazole-NH) | -CH₂CH(CH₃)₂ | pyrazole-NH |
| 25 | (H₃C)₃-C-C(=O)-O-CH₂-NH-C(=O)-CH(CH₂-pyridyl)- | -CH₂-C₆H₄-NH- (indole) | -CH₂CH(CH₃)₂ | imidazole NH |
| 26 | (H₃C)₃-C-C(=O)-O-CH₂-NH-C(=O)-CH(CH₂-C₆H₅)- | -CH₂-(imidazole-NH) | -CH₂CH(CH₃)₂ | oxazole |

-continued

| Example | $X(NH-CH-C)_{\overline{p}}^{R_5\ O}$ | R₄ | R₃ | R₁ |
|---|---|---|---|---|
| 27 | (H₃C)₃-C-O-C-NH-CH-C- with CH₂-imidazole side chain | -CH₂-phenyl | -CH(CH₃)₂ | thiazole |
| 28 | (H₃C)₃-C-O-C-NH-CH-C- with CH₂-CH₂-indole(NH) side chain | -CH₂-imidazole(NH) | -CH₂CH(CH₃)₂ | oxazole |
| 29 | (H₃C)₃-C-O-C-NH-CH-C- with (CH₂)₂-phenyl side chain | -CH₂-imidazole(NH) | -CH₂CH(CH₃)₂ | pyridine |
| 30 | (H₃C)₃-C-O-C-NH-CH-C- with CH₂-phenyl side chain | -CH₂-pyridine | -CH₂CH(CH₃)₂ | NH-benzimidazole |
| 31 | [O=C-CH(CH₂-naphthyl)-]₂ | -CH₂-imidazole(NH) | -CH₂-cyclohexyl | S-benzothiazole |

-continued

| Example | X(NH—CH(R₅)—C(O))ₚ | R₄ | R₃ | R₁ |
|---|---|---|---|---|
| 32 | (H₃CO)₃—C—O—C(O)—NH—CH(CH₂-naphthyl)—C(O)— | —CH₂—C(=CH—NH)—N= (imidazole) | —CH₂CH(CH₃)₂ | 2-oxazoline fused benzene (benzoxazole-CH=) |
| 33 | Ph-CH₂-NH-C(O)-CH(CH₂Ph)-NH-C(O)- | —CH₂—C(=CH—NH)—N= | —CH₂CH(CH₃)₂ | pyrrole-NH |
| 34 | (H₃C)₂HCH₂C—C(O)—NH—CH(CH₂Ph)—C(O)— | —CH₂—C(=CH—NH)—N= | —CH₂CH(CH₃)₂ | N-methyl imidazole-CH₂CH(CH₃)₂ |
| 35 | Ph—SO₂—NH—CH(CH₂Ph)—C(O)— | —CH₂—C(=CH—NH)—N= | —CH₂CH(CH₃)₂ | thiazole-CH₂-cyclohexyl |

-continued

| Example | $X(NH-CH(R_5)-C(O))_p$ | $R_4$ | $R_3$ | $R_1$ |
|---|---|---|---|---|
| 36 | (H₃C)₂HCH₂C−SO₂−NH−CH(CH₂-Ph)−C(O)− | −CH₂−(indol-3-yl) | −CH₂CH(CH₃)₂ | −(CH₂)₂CH(CH₃)₂ attached to imidazole (via CH=N−, NH) |
| 37 | (H₃C)₂HCH₂C−SO₂−NH−CH(CH₂-Ph)−C(O)− | −CH₂−(imidazol-4-yl) | −CH₂CH(CH₃)₂ | −(CH₂)₃−Ph attached to pyrazole (NH) |
| 38 | (H₃C)₃C−O−C(O)− | −CH₂−Ph | −CH₂−(imidazol-4-yl) | −CH₂−(2-methylpyridin-3-yl) |
| 39 | Ph−CH₂−SO₂− | −CH₂−(imidazol-4-yl) | −CH₂CH(CH₃)₂ | −CH₂−Ph attached to imidazole |
| 40 | (H₃C)₂HCH₂C−SO₂− | −CH₂−(imidazol-4-yl) | −CH₂CH(CH₃)₂ | −(CH₂)₂−cyclopentyl attached to imidazole |
| 41 | (H₃C)₂HCH₂C−NH−C(O)− | −CH₂−(imidazol-4-yl) | −CH₂CH(CH₃)₂ | −C(C₂H₅)= attached to imidazole (NH) |

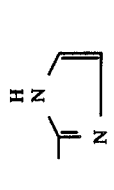

EXAMPLE 47

1000 tablets each containing the following ingredients:

| | |
|---|---|
| $N^2$—[N—[(1,1-Dimethylethoxy)-carbonyl]-L—phenylalanyl]-N—[(1S)—2-cyclohexyl-1-[(R)-hydroxy-1H—imidazol-2-ylmethyl]ethyl]-L—histidinamide, monoacetate salt | 250 mg. |
| Cornstarch | 100 mg. |
| Gelatin | 20 mg. |
| Avicel (microcrystalline cellulose) | 50 mg. |
| Magnesium stearate | 5 mg. |
| | 425 mg. | are prepared from sufficient bulk quantities by mixing the active monoacetate salt compound and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 250 mg. of active ingredient.

In a similar manner, tablets containing 250 mg. of the product of any of Examples 1 to 6 and 8 to 46 can be prepared.

A similar procedure can be employed to form tablets containing 500 mg. of active ingredient.

EXAMPLE 48

An injectable solution is prepared as follows:

| | |
|---|---|
| $N^2$—[N—[(1,1-Dimethylethoxy)-carbonyl]-L—phenylalanyl]-N—[(S)—1-[(R)-hydroxy(1H—imidozol-2-yl)methyl]-3-methylbutyl]-L—histidinamide, acetate salt | 1000 g. |
| Methyl paraben | 5 g. |
| Propyl paraben | 1 g. |
| Sodium chloride | 5 g. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 200 mg. of active ingredient per ml. of solution for injection.

In a similar manner, an injectable solution containing 200 mg. of active ingredient per ml. of solution can be prepared for the product of any of Examples 1, 2, and 4 to 46.

EXAMPLE 49

1000 tablets each containing the following ingredients:

| | |
|---|---|
| $N^2$—[N—[(1,1-Dimetylethoxy)-carbonyl]-L—phenylalanyl]-N—[(1S)—2-cyclohexyl-1-[(R)-hydroxy-1H—imidazol-2-methyl]ethyl]-L—histidinamide, monoacetate salt | 500 mg. |
| Avicel | 300 mg. |
| Hydrochlorothiazide | 14.5 mg. |
| Lactose | 113 mg. |
| Cornstarch | 15.5 mg. |
| Stearic acid | 7 mg. |
| | 950 mg. | are prepared from sufficient bulk quantities by slugging the $N^2$-[N-[(1,1-dimethylethoxy)-carbonyl]-L-phenylalanyl)]-N-[(1S)-2-cyclohexyl-1-[(R)-hydroxy-1H-imidazol-2-ylmethyl]ethyl]-L-histidinamide, monoacetate salt, Avicel, and a portion of the stearic acid. The slugs are ground and passed through a #2 screen, then mixed with the hydrochlorothiazide, lactose, cornstarch, and remainder of the stearic acid. The mixture is compressed into 950 mg. capsule shaped tablets in a tablet press. The tablets are scored for dividing in half.

In a similar manner, tablets can be prepared containing 500 mg. of the product of any of Examples 1 to 6 and 8 to 46.

What is claimed is:

1. A compound of the formula $$X \text{—}(NH\text{—}CH\text{—}\underset{\underset{R_5}{|}}{\overset{\overset{O}{\|}}{C}})_p NH\text{—}CH\text{—}\underset{R_4}{\overset{O}{\|}}{C}\text{—}NH\text{—}CH\text{—}\underset{R_3}{|}CH\text{—}R_1$$
$$\qquad\qquad\qquad\qquad\qquad\qquad\qquad\qquad |$$
$$\qquad\qquad\qquad\qquad\qquad\qquad\qquad\qquad OH$$

or a pharmaceutically acceptable salt thereof wherein:

X is 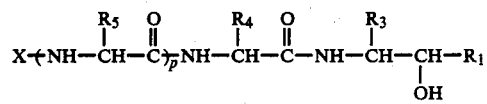,

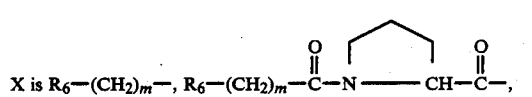,

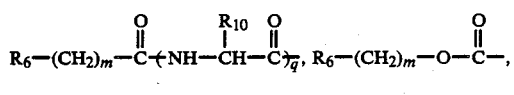,

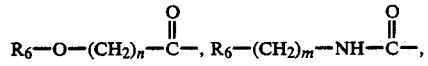,

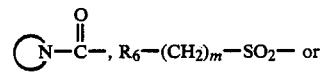 or

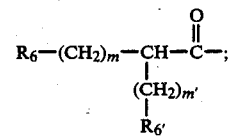;

$R_3$, $R_4$, $R_5$ and $R_{10}$ are independently selected from the group consisting of hydrogen, lower alkyl, halo substituted lower alkyl, —$(CH_2)_n$—aryl, —$(CH_2)_n$—OH, —$(CH_2)_n$—O—lower alkyl, —$(CH_2)_n$—$NH_2$, —$(CH_2)_n$—SH, —$(CH_2)_n$—S—lower alkyl, —$(CH_2)_n$—O—$(CH_2)_g$—OH, —$(CH_2)_n$—O—$(CH_2)_g$—$NH_2$, —$(CH_2)_n$—S—$(CH_2)_g$—OH, —$(CH_2)_n$—$\overset{\overset{O}{\|}}{C}$—OH, —$(CH_2)_n$—S—$(CH_2)_g$—$NH_2$,

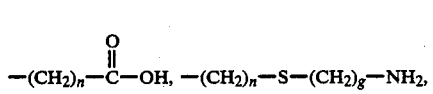, 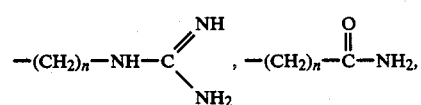,

-continued

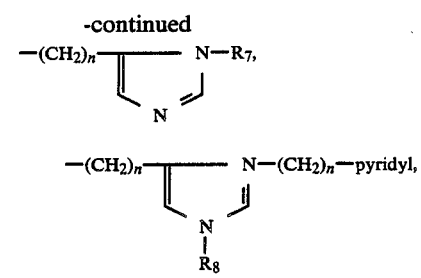

and —(CH$_2$)$_n$—cycloalkyl;

R$_6$ and R$_6'$ are independently selected from the group consisting of lower alkyl, cycloalkyl, and aryl;

p is zero or one;

q is zero or one;

m and m' are independently selected from the group consisting of zero and an integer from 1 to 5;

n is an integer from 1 to 5;

g is an integer from 2 to 5;

R$_7$ is

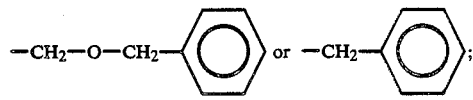

R$_8$ is 2,4-dinitrophenyl,

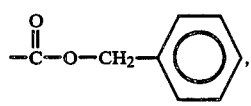

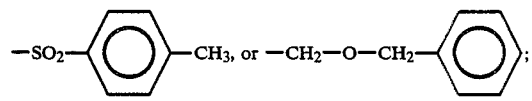

R$_1$ is 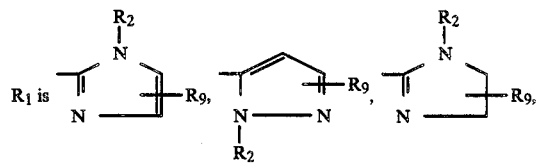

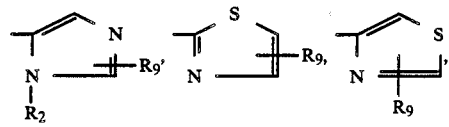

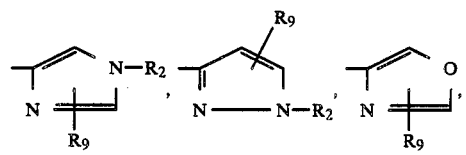

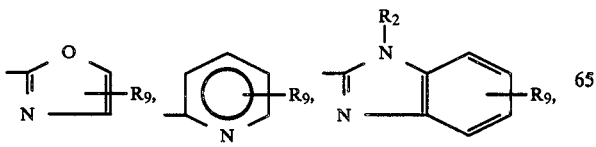

-continued

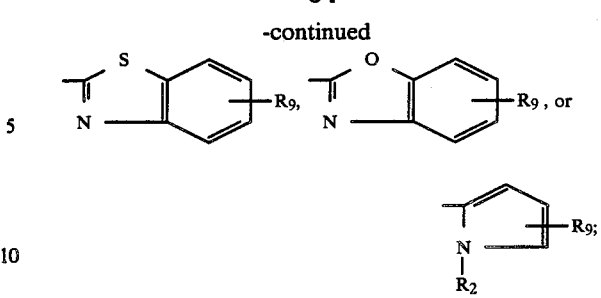

R$_2$ is 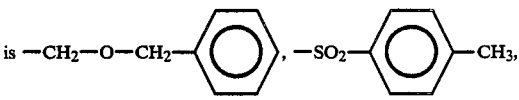

2,4-dinitrophenyl, hydrogen, lower alkyl,

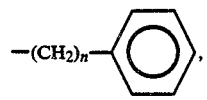

or —(CH$_2$)$_n$—cycloalkyl;

R$_9$ is hydrogen, lower alkyl,

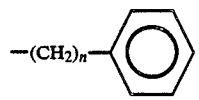

or -(CH$_2$)$_n$—cycloalkyl;

N- represents a heterocyclic ring of the formula

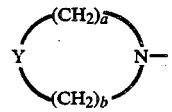

wherein Y is —CH$_2$, O, S, or N-R$_9$, a is an integer from 1 to 4, and b is an integer from 1 to 4 provided that the sum of a plus b is an integer from 2 to 5 and such heterocyclic rings wherein one carbon atom has a lower alkyl substituent;

the term aryl refers to phenyl, 1-naphthyl, 2-naphthyl, mono substututed phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substitutents are methyl, methoxy methylthio, halogen or hydroxy;

the term lower alkyl unless otherwise defined refers to straight or branched chain radicals having up to seven carbon atoms;

the term cycloalkyl refers to saturated rings of 4 to 7 carbon atoms;

the term halo refers to Cl, Br, and F; and the term halo substituted lower alkyl refers to such lower alkyl groups in which one or more hydrogens have been replaced by chloro, bromo or fluoro groups.

2. A compound of the formula

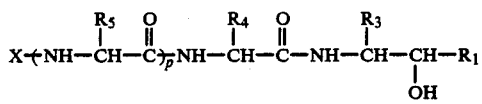

or a pharmaceutically acceptable salt thereof wherein:

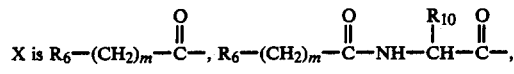

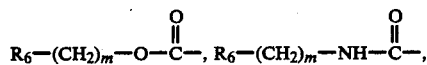

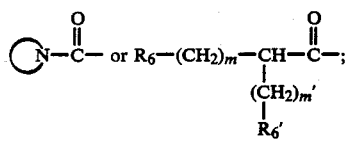

$R_1$ is

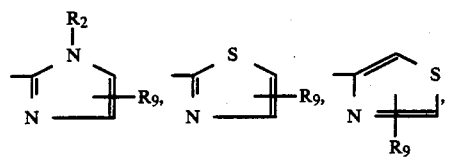

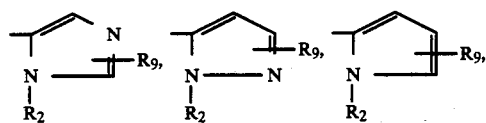

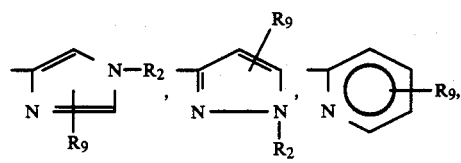

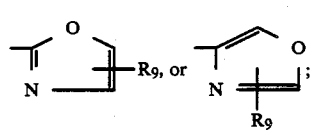

$R_2$ is —$CH_2$—O—$CH_2$— 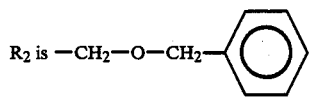

hydrogen, straight or branched chain lower alkyl or up to 5 carbons, or

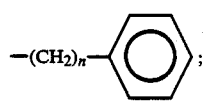

$R_9$ is hydrogen, straight or branched chain lower alkyl of up to 5 carbons, or

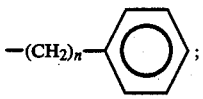

$R_3$ is lower alkyl of 3 to 5 carbons, —$(CH_2)_n$—cyclopentyl, —$(Ch_2)_n$-cyclohexyl or

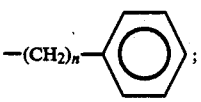

n is an integer from 1 to 3;
$R_4$ is hydrogen, straight or branched chain lower alkyl of up to 5 carbons, —$(CH_2)_4$—$NH_2$,

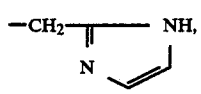

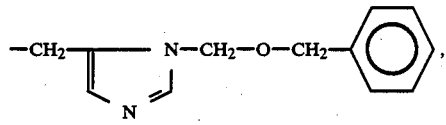

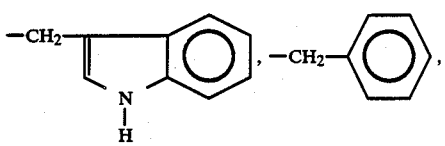

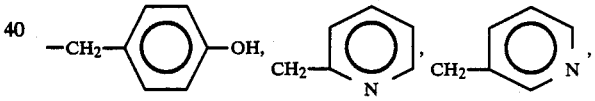

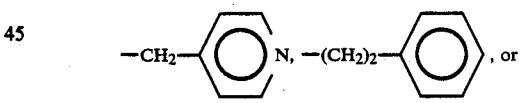

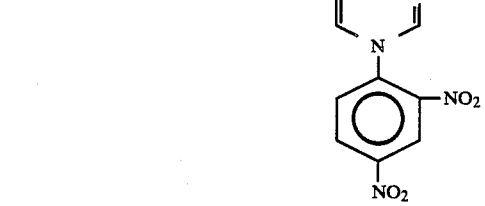

$R_5$ is straight or branched lower alkyl of up to 5 carbons,

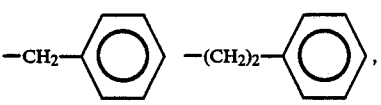

—$CH_2$—(α-naphthyl), —$CH_2$—(β-naphthyl),

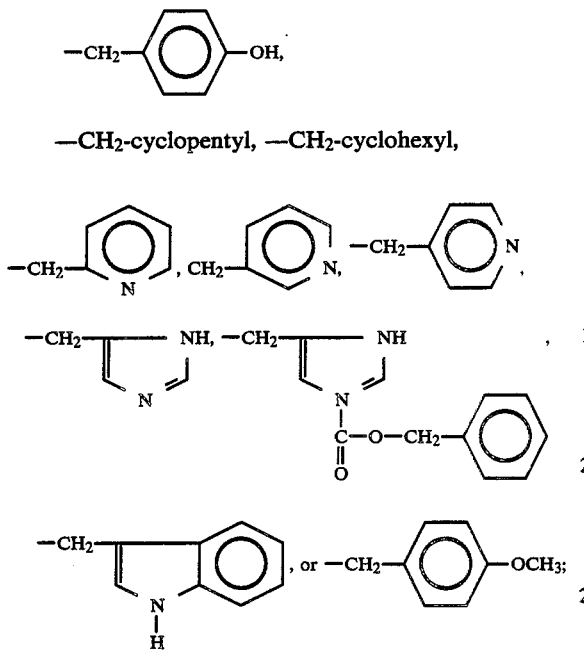

R$_{10}$ is —(CH$_2$)$_4$—NH$_2$;

R$_6$ and R$_6'$ are independently selected from the group consisting of straight or branched chain lower alkyl of up to 5 carbons, cycloalkyl of 4 to 6 carbons, phenyl, 1-naphthyl, and 2-naphthyl;

m and m' are independently selected from the group consisting of zero, one, and two;

p is zero or one; and

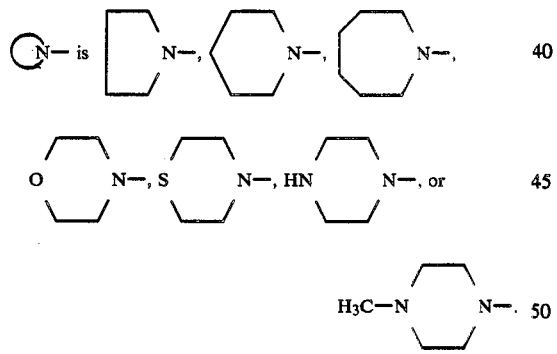

3. A compound of claim 2 wherein

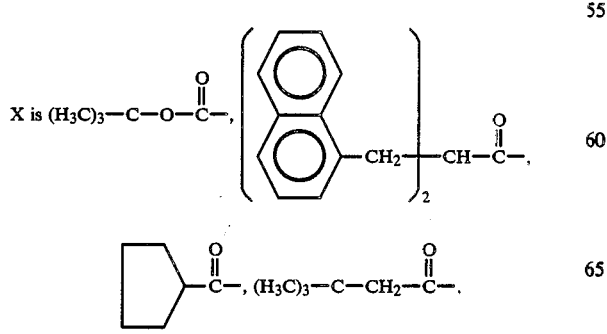

-continued

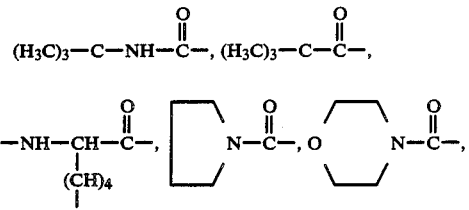

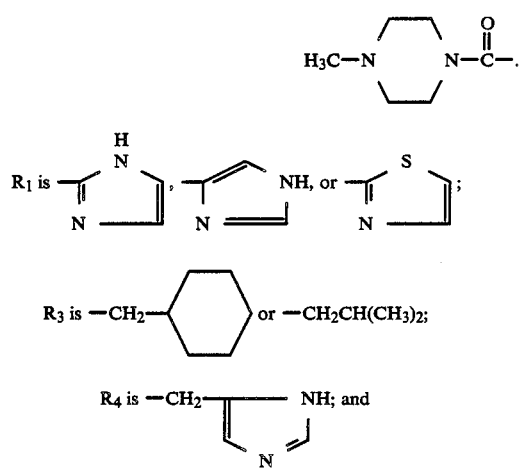

R$_5$ is benzyl.

4. The compound of claim 3 wherein:

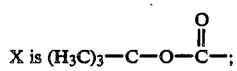

p is one;

R$_3$ is —CH$_2$CH(CH$_3$)$_2$; and

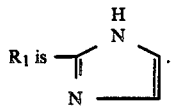

5. The compound of claim 4, N$^2$-[N-[(1,1-dimethylethoxy)carbonyl]-L-phenylalanyl]-N-[(S)-1-[(R)-hydroxy(1H-imidazol-2-yl)methyl]-3-methylbutyl]-L-histidinamide, acetic acid solvate.

6. The compound of claim 3 wherein:

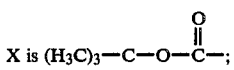

p is one;

R$_3$ is —CH$_2$-cyclohexyl; and

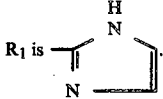

7. The compound of claim 6, N$^2$-[N-[(1,1-dimethylethoxy)carbonyl]-L-phenylalanyl]-N-[(1S)-2-cyclohexyl-1-[(R)-hydroxy-1H-imidazol-2-ylmethyl]-ethyl]-L-histidinamide, monoacetate salt.

8. The compound of claim 3 wherein:

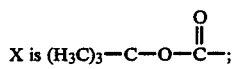

p is one;

R₃ is —CH₂CH(CH₃)₂; and

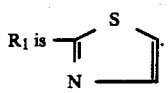

9. The compound of claim 8, N²-[N-[(1,1-dimethylethoxy)carbonyl]-L-phenylalanyl]-N-[(S)-1-[(R)-hydroxy(2-thiazolyl)methyl]-3-methylbutyl]-L-histidinamide, acetate salt.

10. The compound of claim 3 wherein

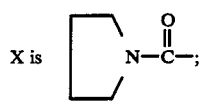

p is one;

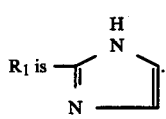

R₁ is

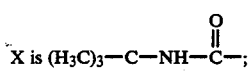

11. The compound of claim 10, N-[(S)-2-cyclohexyl-1-[(R)-hydroxy(1H-imidazol-2-yl)methyl]-ethyl]-N²-[N-(pyrrolidinylcarbonyl)-L-phenylalanyl]-L-histidinamide, dihydrochloride.

12. The compound of claim 3 wherein

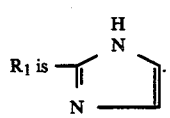

p is one;

R₃ is —CH₂—⟨cyclohexyl⟩; and

R₁ is

13. The compound of claim 12, N-[(S)-2-cyclohexyl-1-[(R)-hydroxy(1H-imidazol-2-yl)-methyl]ethyl]-N²-[[(1,1-dimethylethyl)amino]-carbonyl]-L-phenylalanyl]-L-histidinamide, dihydrochloride.

14. The compound of claim 3 wherein:

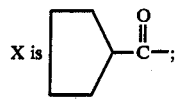

p is one;

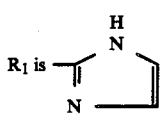

R₁ is

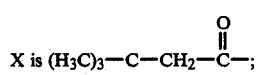

15. The compound of claim 14, N-[(S)-2-cyclohexyl-1-[(R)-hydroxy(1H-imidazol-2-yl)methyl]-ethyl]-N²-[N-(cyclopentylcarbonyl)-L-phenylalanyl]-L-histidinamide, dihydrochloride.

16. The compound of claim 3 wherein:

X is (H₃C)₃—C—CH₂—C(=O)—;

p is one;

R₃ is —CH₂—⟨cyclohexyl⟩; and

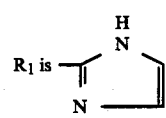

17. The compound of claim 16, N-[(S)-2-cyclohexyl-1-[(R)-hydroxy(1H-imidazol-2-yl)-methyl]ethyl]-N²-[N-(3,3-dimethyl-1-oxobutyl)-L-phenylalanyl]-L-histidinamide, dihydrochloride.

18. The compound of claim 3 wherein:

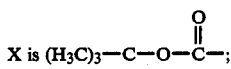

p is one;

R₃ is —CH₂—⟨cyclohexyl⟩; and

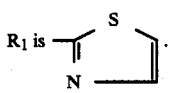

19. The compound of claim 18, (1S,2R)-N-[1-(cyclohexylmethyl)-2-hydroxy-2-(2-thiazolyl)ethyl]-N²-[N-[(1,1-dimethylethoxy)carbonyl]-L-phenylalanyl]-L-histidinamide, 0.5 acetate salt.

20. The compound of claim 3 wherein:

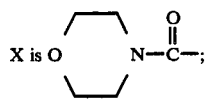

p is one;

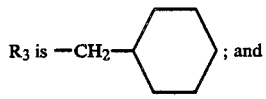

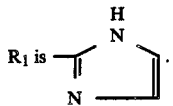

21. The compound of claim 20, (1S,2R)-N-[1-(cyclohexylmethyl)-2-hydroxy-2-(1H-imidazol-2-yl)-ethyl]-$N^2$-[N-(4-morpholinylcarbonyl)-L-phenylalanyl]-L-histidinamide, 2.2 trifluoroacetate salt.

22. The compound of claim 3 wherein:

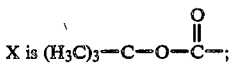

p is one;

 and

23. The compound of claim 3 wherein:

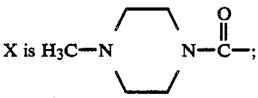

p is one;

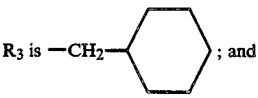

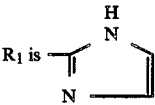

24. The compound of claim 23, (1S,2R)-$N^2$-[N-[(4-methyl-1-piperazinyl)carbonyl]-L-phenyl-alanyl]-N-[1-Ccyclohexylmethyl)-2-hydroxy-2-(1H-imidazol-2-yl)ethyl]-L-histidinamide, trihydrochloride.

25. The compound of claim 3 wherein

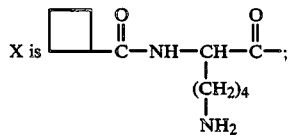

p is one;

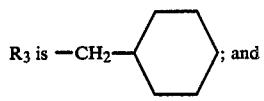

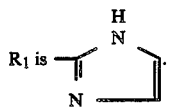

26. The compound of claim 25, (1S,2R)-$N^2$-[N-[$N^2$-(cyclobutylcarbonyl)-L-lysyl]-L-phenylalanyl]-N-[1-Ccyclohexylmethyl)-2-hydroxy-2-(1H-imidazol-2-yl)ethhyl]-L-histidinamide, 3.3 hydrochloride.

27. The compound of claim 3 wherein:

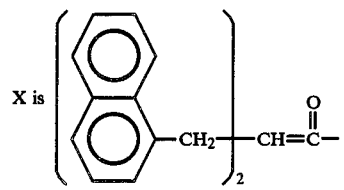

p is zero;

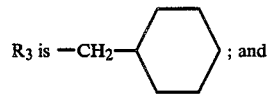

28. The compound of claim 27, (1S,2R)-N-[1-(cyclohexylmethyl)-2-hydroxy-2-(1H-imidazol-2-yl)ethyl]-$N^2$-[1-oxo-3-(1-naphthalenyl)-2-(1-naphthalenylmethyl)propyl]-L-histidinamide, dihydrochloride.

29. The compound of claim 2 wherein:

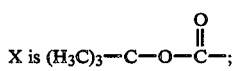

p is one;

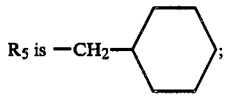

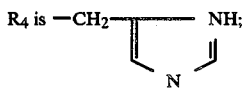

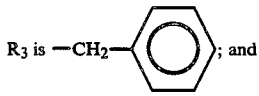

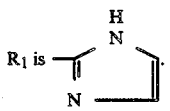

30. The compound of claim 2 wherein:

X is (H₃C)₃—C—O—C(=O)—;

p is one;

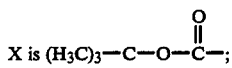
R₅ is —CH₂—(phenyl);

R₄ is —CH₂CH(CH₃)₂;

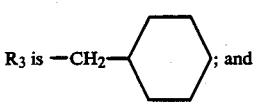
R₃ is —CH₂—(cyclohexyl); and

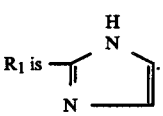
R₁ is imidazolyl.

31. The compound of claim 2 wherein:

X is (H₃C)₃—C—O—C(=O)—;

p is one;

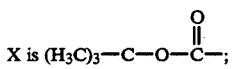
R₅ is —CH₂—(phenyl);

R₄ is hydrogen;

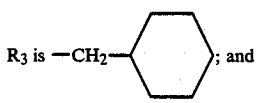
R₃ is —CH₂—(cyclohexyl); and

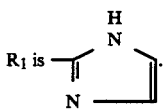
R₁ is imidazolyl.

32. The compound of claim 2 wherein:

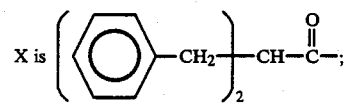
X is [(phenyl)—CH₂—]₂CH—C(=O)—;

p is zero;

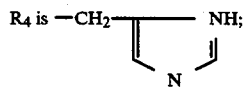
R₄ is —CH₂—(imidazole NH);

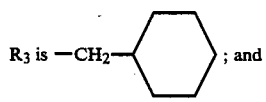
R₃ is —CH₂—(cyclohexyl); and

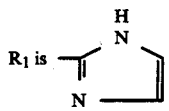
R₁ is imidazolyl.

33. The compound of claim 2 wherein

X is (H₃C)₃—C—C(=O)—;

p is one;

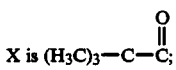
R₅ is —CH₂—(phenyl);

R₄ is —(CH₂)₄—NH₂;

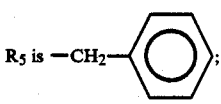
R₃ is —CH₂—(cyclohexyl); and

R₁ is imidazolyl.

34. A composition for treating hypertension in a mammalian species comprising a pharmaceutically acceptable carrier and an anti-hypertensively effective amount of a compound of claim 1.

35. A method of treating hypertension in a mammalian species which comprises administering an anti-hypertensively effective amount of the composition of claim 34.

36. A compound of the formula $$H_2N-CH(R_4)-C(=O)-NH-CH(R_3)-CH(OH)-R_1$$

or a salt thereof wherein

R₃ and R₄ are independently selected from the group consisting of hydrogen, lower alkyl, halo substituted lower alkyl, —(CH₂)ₙ—aryl, —(CH₂)ₙ—OH, —(CH₂)ₙ—O—lower alkyl, —(CH₂)ₙ—NH₂, —(CH₂)ₙ—SH, —(CH₂)ₙ—S—lower alkyl, —(CH₂)ₙ—O—(CH₂)ᵍ—OH, —(CH₂)ₙ—O—(CH₂)ᵍ—NH₂, —(CH₂)ₙ—S—(CH₂)ᵍ—OH

—(CH₂)ₙ—C(=O)—OH,

—(CH₂)ₙ—S—(CH₂)ᵍ—NH₂,

—(CH₂)ₙ—NH—C(=NH)(NH₂),

—(CH₂)ₙ—pyridyl,

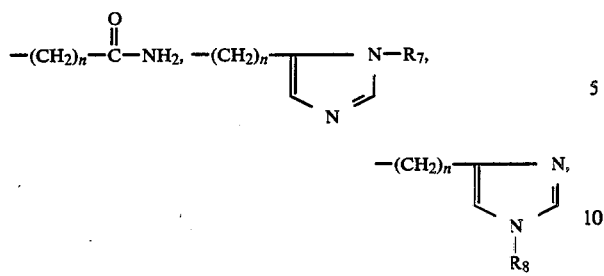

and —(CH₂)ₙ—cycloalkyl;
n is an integer from 1 to 5;
g is an integer from 2 to 5;

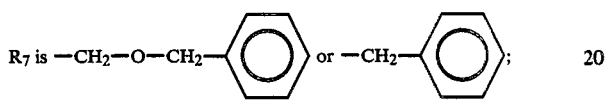

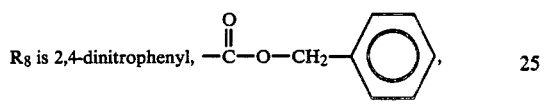

R₈ is 2,4-dinitrophenyl,

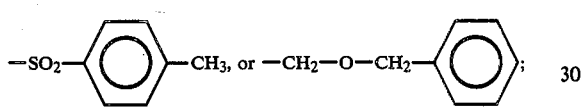

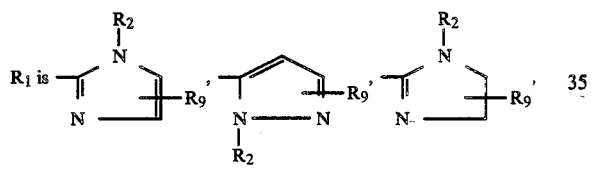

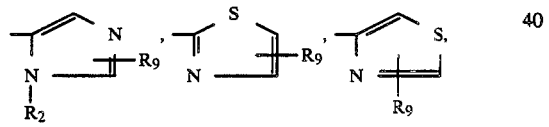

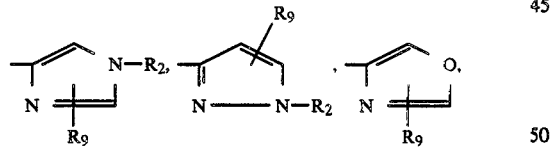

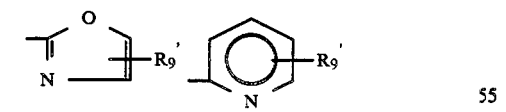

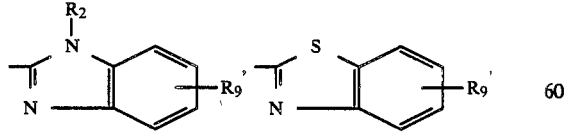

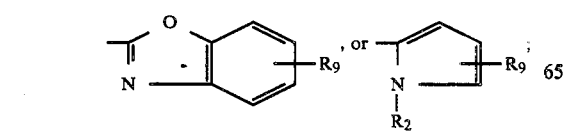

R₂ is

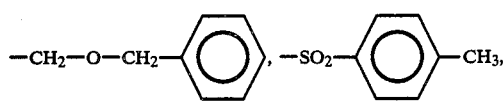

2,4-dinitrophenyl, hydrogen, lower alkyl,

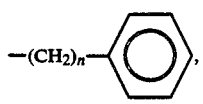

or —(CH₂)ₙ—cycloalkyl;
R₉ is hydrogen, lower alkyl,

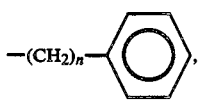

or —(CH₂)ₙ—cycloalkyl;
the term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)₂ wherein alkyl is of 1 to 4 carbons, di or tri substituted phenyl, 1-naphthyl or 2-naphthyl wherein said substituents are methyl, methoxy, methylthio, halogen or hydroxy;

37. A compound of the formula
Claim 36 or a salt thereof wherein

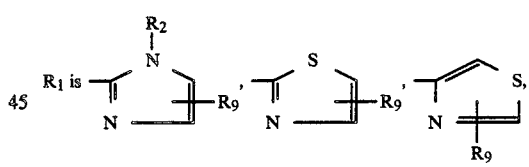

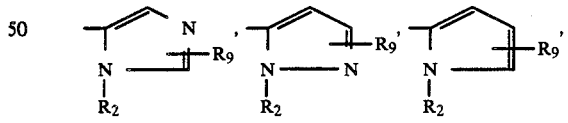

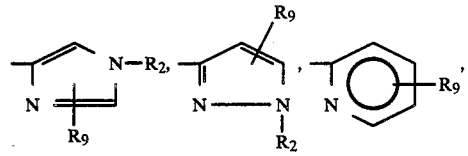

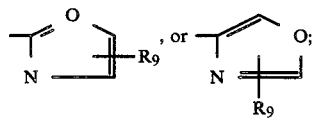

R₂ is

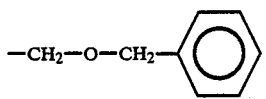

hydrogen, straight or branched chain lower alkyl of up to 5 carbons, or

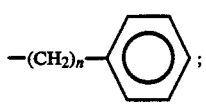

$R_9$ is hydrogen, straight or branched chain lower alkyl of up to 5 carbons, or

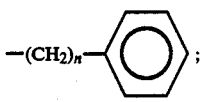

$R_3$ is lower alkyl of 3 to 5 carbons, $-(CH_2)_n-$cyclopentyl, $-(CH_2)_n-$cyclohexyl or

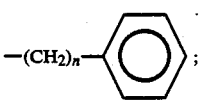

n is an integer from 1 to 3; and
$R_4$ is hydrogen, straight or branched chain lower alkyl of up to 5 carbons, $-(CH_2)_4-NH_2$,

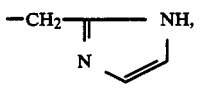

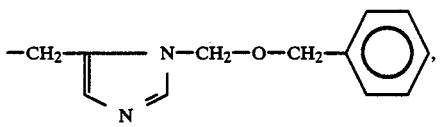

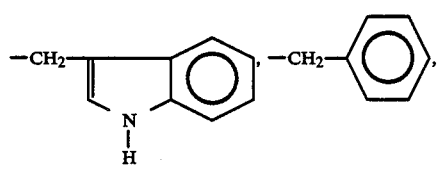

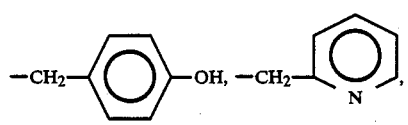

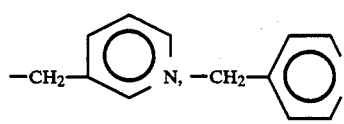

38. The compound of claim 37 wherein

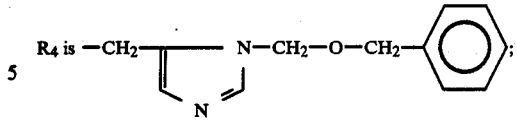

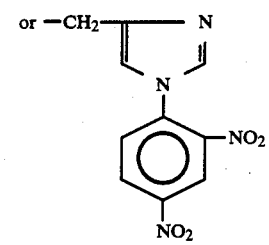

$R_1$ is

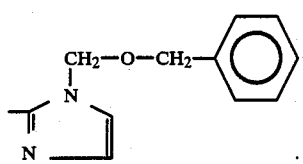

39. The compound of claim 37 wherein

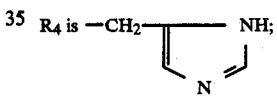

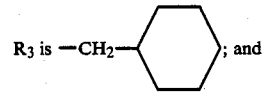

$R_1$ is

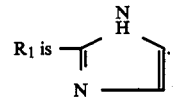

40. A compound of the formula

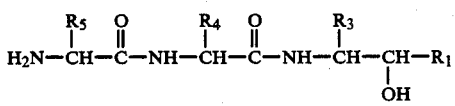

or a salt thereof wherein
$R_3$, $R_4$, and $R_5$ are independently selected from the group consisting of hydrogen, lower alkyl, halo substituted lower alkyl, $-(CH_2)_n-$aryl, $-(CH_2)_n-OH$, $-(CH_2)_n-O-$lower alkyl, $-(CH_2)_n-NH_2$, $-(CH_2)_n-SH$, $-(CH_2)_n-S-$lower alkyl, $-(CH_2)_n-O-(CH_2)_g-OH$, $-(CH_2)_n-O-(CH_2)_g-NH_2$, $-(CH_2)_n-S-(CH_2)_g-OH$,

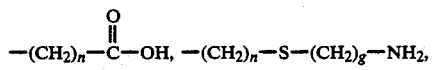

-continued

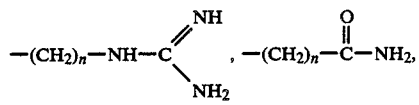, 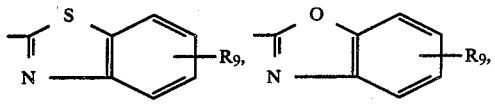

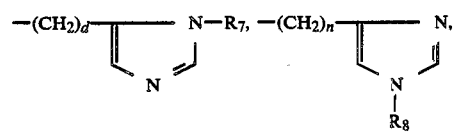, 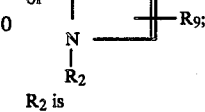

—(CH₂)ₙ—pyridyl, and —(CH₂)ₙ—cycloalkyl;
n is an integer from 1 to 5;
g is an integer from 2 to 5;

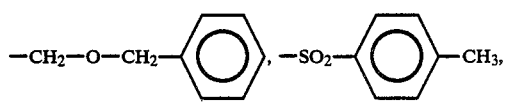

R₂ is

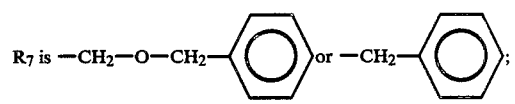

2,4-dinitrophenyl, hydrogen, lower alkyl,

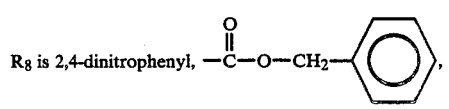

or —(CH₂)ₙ—cycloalkyl;
R₉ is hgydrogen, lowre alkyl,

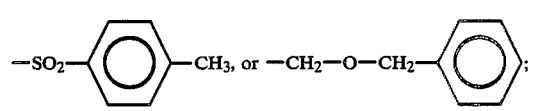

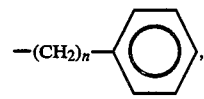

R₁ is 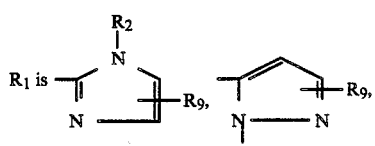

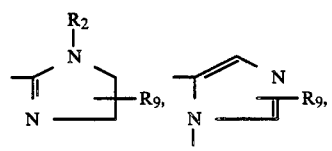

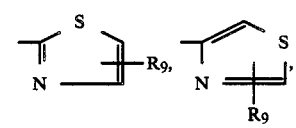

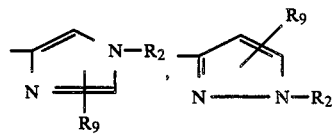

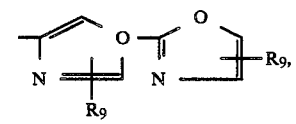

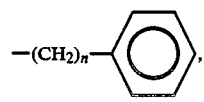

or —(CH₂)ₙ—cycloalkyl;
the term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)₂ wherein alkyl is of 1 to 4 carbons, di or tri substituted phenyl, 1-naphthyl or 2-naphthyl wherein said substitutents are methyl, methoxy, methylthio, halogen or hydroxy;
the term lower alkyl unless otherwise defined refers to straight or branched chain radicals having up to seven carbon atoms;
the term cycloalkyl refers to saturated rings of 4 to 7 carbon atoms;
the term halo refers to Cl, Br, and F; and
the term halo substituted lower alkyl refers to such lower alkyl groups in which one or more hydrogens have been replaced by chloro, bromo or fluoro groups.

41. A compound of claim 40 or a salt thereof wherein

R₁ is

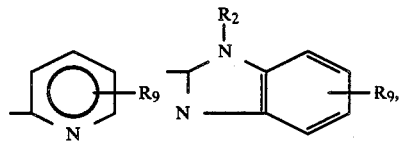

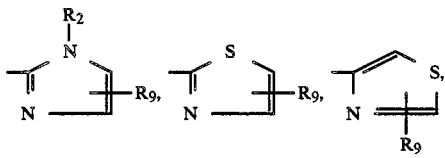

-continued

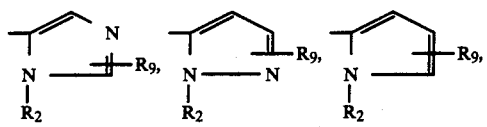

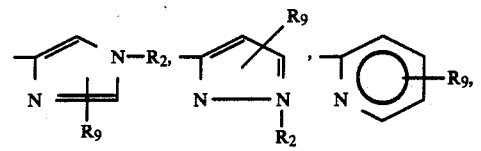

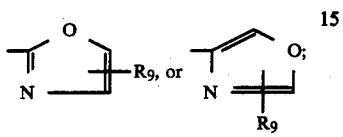

$R_2$ is

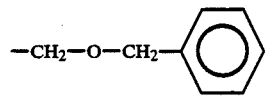

hydrogen, straight or branched chain lower alkyl of up to 5 carbons, or

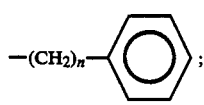

$R_9$ is hydrogen, straight or branched chain lower alkyl of up to 5 carbons, or

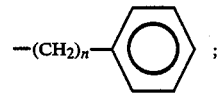

$R_3$ is lower alkyl of 3 to 5 carbons, —(CH$_2$)$_n$cyclopentyl, —(CH$_2$)$_n$—cyclohexyl or

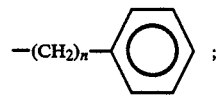

n is an integer from 1 to 3;
$R_4$ is hydrogen, straight or branched chain lower alkyl of up to 5 carbons —(CH$_2$)$_n$—NH$_2$,

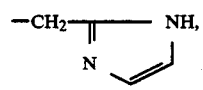

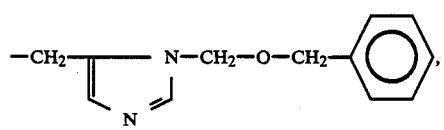

-continued

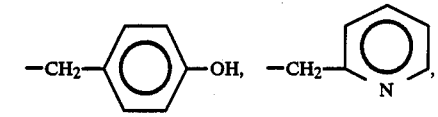

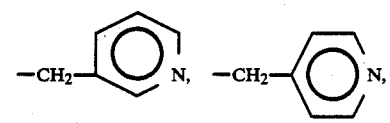

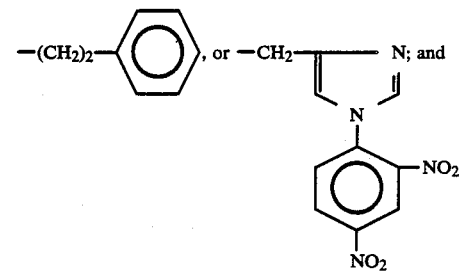

$R_5$ is straight or branched lower alkyl of up to 5 carbons,

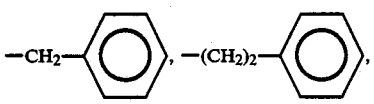

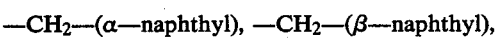

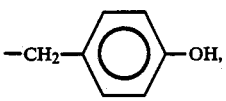

—CH$_2$—cyclopentyl, —CH$_2$—cyclohexyl,

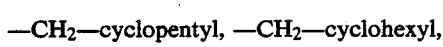

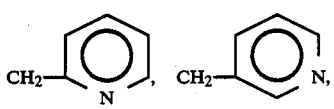

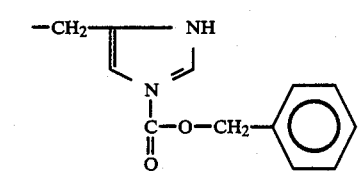

-continued
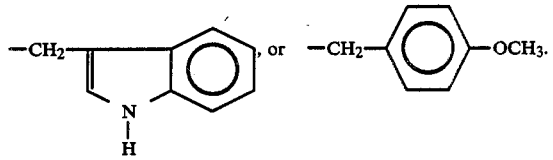
42. The compound of claim 41 wherein
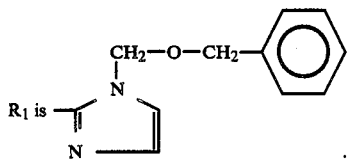
* * * * *